United States Patent [19]
Wels et al.

[11] Patent Number: 5,939,531
[45] Date of Patent: *Aug. 17, 1999

[54] RECOMBINANT ANTIBODIES SPECIFIC FOR A GROWTH FACTOR RECEPTOR

[75] Inventors: Winfried Stephan Wels; Nancy E. Hynes, both of Basel, Switzerland; Ina-Maria Harwerth, Grenzach-Wyhlen, Germany; Bernd Groner, Basel, Switzerland; Norman Hardman, Riehen, Switzerland; Markus Zwickl, Basel, Switzerland

[73] Assignee: Novartis Corp., Basel, Switzerland

[*] Notice: This patent is subject to a terminal disclaimer.

[21] Appl. No.: 08/465,473

[22] Filed: Jun. 5, 1995

Related U.S. Application Data

[63] Continuation of application No. 08/235,838, Apr. 29, 1994, Pat. No. 5,571,894, which is a continuation of application No. 07/828,832, Jan. 31, 1992, abandoned, which is a continuation-in-part of application No. 07/731,190, Jul. 15, 1991, abandoned.

[51] Int. Cl.$^6$ .......................... C07K 16/30; C07K 16/46
[52] U.S. Cl. ........................... 530/387.3; 530/388.22; 530/387.7; 530/388.8; 435/69.7
[58] Field of Search .......................... 424/135.1, 143.1, 424/183.1; 435/240.27, 172.2, 69.7; 530/388.22, 387.3, 388.1, 387.7, 388.8

[56] References Cited

U.S. PATENT DOCUMENTS

| | | | |
|---|---|---|---|
| 4,545,985 | 10/1985 | Pastan et al. | 424/85 |
| 4,816,567 | 3/1989 | Cabilly et al. | 530/387 |
| 4,851,341 | 7/1989 | Hopp et al. | 435/68 |
| 4,892,827 | 1/1990 | Pastan et al. | 435/193 |
| 4,946,778 | 8/1990 | Ladner et al. | 435/69.6 |
| 5,091,513 | 2/1992 | Huston et al. | 530/387 |
| 5,571,894 | 11/1996 | Wels et al. | 530/387.3 |

FOREIGN PATENT DOCUMENTS

| | | |
|---|---|---|
| 0171496 | 2/1986 | European Pat. Off. . |
| 0368684 | 11/1989 | European Pat. Off. . |
| WO89/05816 | 6/1989 | WIPO . |
| WO89/06692 | 7/1989 | WIPO . |
| WO89/09825 | 10/1989 | WIPO . |
| 89/10412 | 11/1989 | WIPO . |
| WO89/10971 | 11/1989 | WIPO . |
| WO89/11533 | 11/1989 | WIPO . |
| WO90/12592 | 11/1990 | WIPO . |
| WO90/14357 | 11/1990 | WIPO . |
| WO91/09965 | 7/1991 | WIPO . |

OTHER PUBLICATIONS

Prickett et al., A calcium–dependent antibody for identification and purification of recombinant proteins, BioTechniques, 7(6): 580–589, 1989.

O'Sullivan, Enzyme innumoassay, in Practical Immunoassay, W.R. Butt, Ed., Marcel Dekker, Inc.: New York, NY, pp. 37–69, 1984.

Goding, Monoclonal Antibodies:Principles and Practice, Harcourt Brace Jovanovich:London, UK, pp. 19–240, 1987.

Bird, R.E. et al., "Single–Chain Antigen–Binding Proteins", *Science*, 242:43–426 (1988).

Chaudhary, V.K. et al., "A Recombinant Immunotoxin Consisting of Two Antibody Variable Domains Fused to *Pseudomonas* Exotoxin", *Nature*, 339:394–397 (1989).

Chaudhary, V.K. et al., "A Rapid Method of Cloning Functional Variable–Region Antibody Genes in *Escherichia coli* as Single–Chain Immunotoxins", *PNAS.*, 87:1066–1070 (1990).

Groner, B. et al., Abstract, "Growth Factor Receptor Specific Single Chain Antibody Chimeras Provide Novel Tools for Immunodiagnostics and Targeted Breast Cancer Therapy", *European Workshop Genetic Alterations in Human Solid Tumors*, p. 10, Montpellier, France, (May 9–11th, 1991).

Groner, B. et al., Abstract, "Single Chain Antibody Chimeras Specific for the C–ERBB–2 Receptor Protein Provide Novel Tools for Immunodiagnostics and Targeted Breast Cancer Therapy", *Fourth International Congress on Hormones and Cancer*, p. 102, Amsterdam, The Netherlands (Sep. 15–19, 1991).

Harwerth, M. et al., Abstract, "Isolation and Charactrization of Monoclonal Antibodies Specific for the C–erbB–2 Protein", *Annual Report of the Friedrich Miescher Institut*, Basel, Switzerland, p. 58 (1989/90).

Hudziak, R.M. et al., "p185$^{HER2}$ Monoclonal Antibody Has Antiproliferative Effects in Vitro and Sensitizes Human Breast Tumor Cells to Tumor Necrosis Factor", *Molecular and Cellular Biology*, 9(3):1165–1172 (1989).

Huston, J.S. et al., "Protein Engineering of Antibody Binding Sites: Recovery of Specific Activity in an Anti–digoxin Single–chain Fv Analogue Produced in *Escherichia coli*", *PNAS*, 85:5879–5883 (1988).

Hynes, N.E. et al., "Epidermal Growth Factor Receptor, but Not c–erbB–2, Activation Prevents Lactogenic Hormone Induction of the β–Casein Gene in Mouse Mammary Epithelial Cells", *Molecular and Cellular Biology*, 10(8):4027–4034 (1990).

(List continued on next page.)

*Primary Examiner*—Lila Feisee
*Assistant Examiner*—Claire M. Kaufman
*Attorney, Agent, or Firm*—Hesna J. Pfeiffer

[57] ABSTRACT

The invention concerns recombinant antibodies directed to the extracellular domain of the human growth factor receptor c-erbB-2 comprising a light chain variable domain and a heavy chain variable domain of a monoclonal antibody, monoclonal antibodies directed to c-erbB-2 themselves, a method of manufacture of said recombinant antibodies and said monoclonal antibodies, hybridoma cells secreting said monoclonal antibodies, a method of manufacture of said hybridoma cells, DNA coding for the heavy chain variable domain, for the light chain variable domain and for the recombinant antibody, a method of manufacture of said DNA, hybrid vectors suitable for expression of said DNA, host cells transformed with said DNA, and the use of said recombinant antibodies and said monoclonal antibodies in the diagnosis and treatment of tumors.

6 Claims, No Drawings

OTHER PUBLICATIONS

Hynes, N.E. et al., Abstract, "Single Chain Antibody Chimeras Specific for the c–erbB–2 Receptor Protein Provide Novel Tools for Immunodiagnostics and Targeted Breast Cancer Therapy", *The Second Meeting on the Molecular Basis of Human Cancer*, Frederick, MD., USA, p. 102 (Jun., 1991).

Hynes, N.E. et al., Abstract PS 7.4, "The c–erbB–2 Protein As a Traget for Directing Cytotoxic Agents to Tumor Cells", *11th Biennial Meeting of the European Association for Cancer Research*, Genoa, Italy, p. 59 (Nov. 3–6, 1991).

Kreitman, R.J. et al., "The Recombinant Immunotoxin Anti–Tac(Fv)–*Pseudomonas* Exotoxin 40 is Cytotoxic Toward Peripheral Blood Malignant Cells from Patients with Adult T–cell Leukemia", *PNAS*, 87(21):8291–8295 (1990).

McKenzie, S.J. et al., "Generation and Characterization of Monoclonal Antibodies Specific for the Human *neu* Oncogene Product p. 185", *Oncogene*, 4:543–548 (1989).

Skerra, A. et al., "Assembly fo a Functional Immunoglobulin Fv Fragment in *Escherichia coli*", *Science*, 240:1038–1041 (1988).

Wels, W. et al., Abstract, "Construction of Recombinant Single–chain Antibodies Specific for the c–erbB–2 Protein", *Annual Report of the Friedrich Miescher Institute*, Basel, Switzerland, p. 58 (1989/90).

Brinkmann et al., B3(Fv)–PE38KDEL, a single–chain immunotoxin that causes complete regression of a human carcinoma in mice, Proc. Natl. Acad. Sci., USA, 88:8616–8620, Oct. 1991.

RECOMBINANT ANTIBODIES SPECIFIC FOR A GROWTH FACTOR RECEPTOR

This is a continuation application of Ser. No. 08/235,838, filed Apr. 29, 1994, now U.S. Pat. No. 5,571,894 which is a continuation of Ser. No. 07/828,832, filed Jan. 31, 1992, now abandoned, which is a continuation-in-part of Ser. No. 07/731,190, filed Jul. 15, 1991, now abandoned.

BACKGROUND OF THE INVENTION

Growth factors and their receptors are involved in the regulation of cell proliferation, and they also seem to play a role in tumor growth. The c-erbB-2 growth factor receptor protein, a protein of the membrane receptor protein tyrosine kinase family (A. Ullrich & J. Schlessinger, Cell 61: 203–212, 1990), is found in human breast tumors and human ovarian carcinomas. Amplification of the c-erbB-2 gene and over-expression of the protein appears to correlate with poor prognosis for tumor patients. Thus the c-erbB-2 protein has potential, both as a diagnostic marker and as a target for cancer therapy. Sequence analysis reveals that c-erbB-2, also called HER2, a glycoprotein of 185 kilo-Dalton (gp185), is identical or closely related to the human analog of the neu oncogene (A. L. Schechter et al., Science 229: 976–978, 1985) and shows considerable sequence homology to the human epidermal growth factor (EGF) receptor.

Of particular interest in tumor diagnosis and therapy are antibodies directed to tumor markers. Polyclonal antibodies may be obtained from the serum of mammals immunized with the antigen, i.e. the tumor marker. The development of hybridoma technology made it possible to generate continuous cell lines, in particular murine hybridomas, producing monoclonal antibodies of the desired specificity. Murine monoclonal antibodies directed to c-erbB-2 are known and are described, for example, by S. J. McKenzie et al., Oncogene 4: 543–548, 1989; R. M. Hudziak et al., Molecular and Cellular Biology 9: 1165–1172, 1989; International Patent Application WO 89/06692 (Genentech); and Japanese Patent Application Kokai 02-150 293 (Ajinomoto KK).

A major limitation in the use of murine-derived monoclonal antibodies as in vivo diagnostic and therapeutic agents is their immunogenicity as foreign proteins, their rather long persistence in the circulation, and the formation of damaging immune complexes. On the other hand, the treatment with human monoclonal antibodies is also limited since human hybridoma cell lines are hard to prepare, generally unstable, and do not produce monoclonal antibodies of appropriate specificity in sufficient quantities and at reasonable costs. In principle, the in vitro use of murine monoclonal antibodies is without limitation. However, production costs of monoclonal antibodies and, depending on the type of immunoassay used, the need for attaching a detectable marker to the antibody make it desirable to find more economic alternatives to regular murine monoclonal antibodies.

A promising alternative is the modification of immunoglobulin genes in order to tailor antibodies for particular diagnostic and therapeutic tasks. Due to the fact that the variable region and each of the constant region domains of immunoglobulin molecules are encoded in separate exons with their own splice sites, recombinant DNA techniques can be used to isolate different parts of cloned immunoglobulin genes and ligate them to parts of other immunoglobulins or to effector molecules. The reconstructed genes are expressed by appropriate transformed continuous cell lines. Murine antibodies can, for example, be converted into "humanized" antibodies by exchanging murine constant domain exons for human immunoglobulin constant domain exons, thus generating chimeric antibodies with murine antibody-combining sites and human constant domains. The chimeric antibodies retain the antigen specificity determined by the murine variable domains, but also exhibit human effector functions (such as complement binding, stimulation of phagocytosis, triggering of granule release by mast cells) determined by the carboxy-terminal constant domain segments of the heavy chain polypeptides. An even more sophisticated technique in tailoring antibodies described in European Patent Application 0 239 400 exchanges also other fairly conserved domains, the so-called framework regions (FRs), within the murine variable domains for corresponding framework regions from human antibodies or for other human protein sequences. Such an antibody should be even less immunogenic in man since the only parts derived from a murine antibody are those hypervariable regions which define a particular specificity for an antigen, the so-called complementarity determining regions (CDRs).

Furthermore, fusion proteins different from immunoglobulins may be formed, e.g. single-chain antibodies, which retain the specificity and binding properties of the starting murine monoclonal antibody, but have otherwise novel properties derived from the non-immunoglobulin part of the fusion protein. The smallest domain of a monoclonal antibody which can bind to the antigen is the so-called Fv fragment which consists of the variable domains of the heavy and light chains. Fv fragments are difficult to prepare by proteolytic techniques since the corresponding variable domains tend to dissociate upon dilution. Fv molecules constructed by joining the variable domains of the heavy and light chains via a short peptide linker, also called single-chain antigen binding proteins, bind to an antigen with similar characteristics as the original monoclonal antibody (R. E. Bird et al., Science 242: 423–426, 1988; J. S. Huston et al., Proc. Natl. Acad. Sci. USA 85: 5879–5883, 1988; and International Patent Application WO 89/09825 (Celltech)). Fv encoding genes can, in principle, be linked to genes encoding effector molecules by recombinant gene technology. It is known, for example, that Fv encoding gene sequences can be linked to a gene encoding a portion of the Pseudomonas exotoxin A gene (V. K. Chaudhary et al., Nature 339: 394–397, 1989; and International Patent Application WO 89/11533 (I. Pastan et al.)).

OBJECT OF THE INVENTION

It is an object of this invention to provide recombinant antibodies directed to the extracellular domain of the human growth factor receptor c-erbB-2 comprising a light chain variable domain and a heavy chain variable domain of a monoclonal antibody, monoclonal antibodies directed to c-erbB-2 themselves, a method of manufacture of said recombinant antibodies and said monoclonal antibodies, hybridoma cells secreting said monoclonal antibodies, a method of manufacture of said hybridoma cells, DNA coding for the heavy chain variable domain, for the light chain variable domain and for the recombinant antibody, a method of manufacture of said DNA, hybrid vectors suitable for expression of said DNA, host cells transformed with said DNA, and the use of said recombinant antibodies and said monoclonal antibodies in the diagnosis and treatment of tumors.

DETAILED DESCRIPTION OF THE INVENTION

The invention concerns a recombinant antibody directed to the extracellular domain of the growth factor receptor c-erbB-2, a human glycoprotein of 185 kilo-Dalton (gp185), comprising a heavy chain variable domain and a light chain variable domain of a monoclonal antibody.

Such a recombinant antibody may be a chimeric antibody consisting, for example, of a mouse heavy chain variable domain with the specificity for c-erbB-2 and a human heavy chain constant domain α, γ, δ, ε or μ, preferably γ, such as γ1 or γ4, and of a mouse light chain variable domain with the specificity for c-erbB-2 and a human light chain constant domain κ or λ, preferably κ, all assembled to give a functional antibody.

The preferred recombinant antibody of the invention is a single-chain antibody wherein the heavy chain variable domain and the light chain variable domain are linked by way of a spacer group, preferably a peptide. Most preferred is a single-chain antibody wherein the heavy chain variable domain is located at the N-terminus of the recombinant antibody. The single-chain recombinant antibody may further comprise an effector molecule and/or signal sequences facilitating the processing of the antibody by the host cell in which it is prepared. Effector molecules considered are those useful for diagnostic or therapeutic purposes, for example enzymes causing a detectable reaction, e.g. phosphatase, such as alkaline phosphatase from *E. coli* or mamalian alkaline phosphatase, e.g. bovine alkaline phosphatase, horseradish peroxidase, β-D-galactosidase, glucose oxidase, glucoamylase, carbonic anhydrase, acetylcholinesterase, lysozyme, malate dehydrogenase or glucose-6-phosphate, a peptide having particular binding properties, e.g. streptavidin from *Streptomyces avidinii* strongly binding to biotin, or enzymes, toxins or other drugs attacking the cells to which the antibody is bound, e.g. a protease, a cytolysin or an exotoxin, for example ricin A, diphtheria toxin A, or Pseudomonas exotoxin. In the following a single-chain recombinant antibody further comprising an effector molecule is referred to as fusion protein or intended to be within the meaning of the terms "single chain (recombinant) antibody" or "recombinant antibody", if appropriate.

The term effector molecule also includes biologically active variants of the above-mentioned proteins, e.g. variants produced from a DNA which has been subjected to in vitro mutagenesis, with the provision that the protein encoded by said DNA retains the biological activity of the native protein. Such modifications may consist in an addition, exchange or deletion of amino acids, the latter resulting in shortened variants. For example, an enzyme, such as phosphatase, may be prepared from a DNA which has been modified to facilitate the cloning of the encoding gene, or an exotoxin, such as Pseudomonas exotoxin, may be prepared from a DNA which has been mutated to delete the cell binding domain.

The recombinant antibodies of the invention are tested for their specificity to the extracellular domain of c-erbB-2, for example by immunofluorescent staining of cells expressing high levels of c-erbB-2, by immunoblotting either directly or by way of immunoprecipitation and protein blotting of the immunocomplexes, or by another immunoassay such as a binding, crossinhibition or competition radio- or enzyme immunoassay.

The variable domain of an antibody heavy or light chain consists of so-called framework regions (FRs), which are fairly conserved in antibodies with different specificities, and of hypervariable regions also called complementarity determining regions (CDRs), which are typical for a particular specificity.

Preferred recombinant antibodies of the invention are those wherein the heavy chain variable domain comprises a polypeptide of the formula $$FR_1—CDR_{1H}—FR_2—CDR_{2H}—FR_3—CDR_{3H}—FR_4 \quad (I)$$

wherein $FR_1$ is a polypeptide residue comprising at least 25–29, preferably 25–33 naturally occurring amino acids, $FR_2$ is a polypeptide residue comprising 12–16 naturally occurring amino acids, $FR_3$ is a polypeptide residue comprising 30–34 naturally occurring amino acids, $FR_4$ is a polypeptide residue comprising at least 6–10, preferably 6–13 naturally occurring amino acids, $CDR_{1H}$ is a polypeptide residue of the amino acid sequence 32 to 36 of SEQ ID NO:4 and 5, $CDR_{2H}$ is a polypeptide residue of the amino acid sequence 51 to 67 of SEQ ID NO:4 and 5, and $CDR_{3H}$ is a polypeptide residue of the amino acid sequence 100 to 109 of SEQ ID NO:4 and 5, or, $CDR_{1H}$ is a polypeptide residue of the amino acid sequence 32 to 36 of SEQ ID NO:10 and 11, $CDR_{2H}$ is a polypeptide residue of the amino acid sequence 51 to 67 of SEQ ID NO:10 and 11, and $CDR_{3H}$ is a polypeptide residue of the amino acid sequence 100 to 110 of SEQ ID NO:10 and 11, and wherein the amino acid Cys may be in the oxidized state forming S—S-bridges. These particular complementarity determining regions are Asn-Tyr-Gly-Met-Asn ($CDR_{1H}$), Trp-Ile-Asn-Thr-Ser-Thr-Gly-Glu-Ser-Thr-Phe-Ala-Asp-Asp-Phe-Lys-Gly ($CDR_{2H}$), and Trp-Glu-Val-Tyr-His-Gly-Tyr-Val-Pro-Tyr ($CDR_{3H}$) according to SEQ. ID NO: 4 and 5, or Ser-Tyr-Trp-Met-Asn ($CDR_{1H}$), Met-Ile-Asp-Pro-Ser-Asp-Ser-Glu-Thr-Gln-Tyr-Asn-Gln-Met-Phe-Lys-Asp ($CDR_{2H}$) and Gly-Gly-Ala-Ser-Gly-Asp-Trp-Tyr-Phe-Asp-Val ($CDR_{3H}$) according to SEQ ID NO:10 and 11.

Especially preferred are recombinant antibodies comprising a heavy chain variable domain of formula I, wherein the polypeptide residues of the framework regions $FR_1$, $FR_2$, $FR_3$ and $FR_4$ are those preferably occurring in mammalian, especially murine or human, antibodies.

In a first embodiment of the invention, most preferred are recombinant antibodies with a heavy chain variable domain comprising a polypeptide of the amino acid sequence 2 to 120, of SEQ ID NO:4 and 5, wherein optionally one or more, e.g. 1, 2, 3 or 4, single amino acids within the amino acid sequences 2 to 31 ($FR_1$), 37 to 50 ($FR_2$), 68 to 99 ($FR_3$), and/or 110 to 120 ($FR_4$), are replaced by other amino acids or deleted, and wherein the amino acid Cys may be in the oxidized state forming S—S-bridges, in particular the recombinant antibodies with a heavy chain variable domain comprising a polypeptide of the amino acid sequence 2 to 120 of SEQ ID NO:4 and 5, wherein the amino acid Cys may be in the oxidized state forming S—S-bridges.

In a second embodiment of the invention, most preferred are recombinant antibodies wherein the heavy chain variable domain comprises a polypeptide of the amino acid sequence 2 to 121, of SEQ ID NO:10 and 11, wherein optionally one or more, e.g. 1, 2, 3 or 4, single amino acids within the amino acid sequences 2 to 31 ($FR_1$), 37 to 50 ($FR_2$), 68 to 99 ($FR_3$), and/or 111 to 121 ($FR_4$), are replaced by other amino acids or deleted, and wherein the amino acid Cys may be in the oxidized state forming S—S-bridges, in particular the recombinant antibodies with a heavy chain variable domain comprising a polypeptide of the amino acid sequence 2 to 121 of SEQ ID NO:10 and 11, wherein the amino acid Cys may be in the oxidized state forming S—S-bridges.

For example, a hydrophobic amino acid within the framework regions may be replaced by another amino acid, preferably also a hydrophobic amino acid, e.g. a homologous amino acid, replaced by two amino acids, or deleted. Likewise, a hydrophilic amino acid within the framework region may be replaced by another amino acid, two amino acids or deleted, whereby replacing amino acids preferably maintain the hydrogen bond structure of the corresponding framework region.

Likewise preferred recombinant antibodies of the invention are those wherein the light chain variable domain comprises a polypeptide of the formula

$$FR_6—CDR_{1L}—FR_7—CDR_{2L}—FR_8—CDR_{3L}—FR_9 \qquad (II)$$

wherein $FR_6$ is a polypeptide residue comprising naturally occurring amino acids, preferably 19–25, especially 19–23 naturally occurring amino acids, $FR_7$ is a polypeptide residue comprising 13–17 naturally occurring amino acids, $FR_8$ is a polypeptide residue comprising 30–34 naturally occurring amino acids, $FR_9$ is a polypeptide residue comprising naturally occurring amino acids, particularly 7–11 naturally occurring amino acids, and $CDR_{1L}$ is a polypeptide residue of the amino acid sequence 159 to 169 of SEQ ID NO:4 and 5, $CDR_{2L}$ is a polypeptide residue of the amino acid sequence 185 to 191 of SEQ ID NO:4 and 5, and $CDR_{3L}$ is a polypeptide residue of the amino acid sequence 224 to 232 of SEQ ID NO:4 and 5, or $CDR_{1L}$ is a polypeptide residue of the amino acid sequence 160 to 170 of SEQ ID NO:10 and 11, $CDR_{2L}$ is a polypeptide residue of the amino acid sequence 186 to 192 of SEQ ID NO:10 and 11, and $CDR_{3L}$ is a polypeptide residue of the amino acid sequence 225 to 232 of SEQ ID NO:10 and 11, and wherein the amino acid Cys may be in the oxidized state forming S—S-bridges. These particular complementarity determining regions are Lys-Ala-Ser-Gln-Asp-Val-Tyr-Asn-Ala-Val-Ala ($CDR_{1L}$), Ser-Ala-Ser-Ser-Arg-Tyr-Thr ($CDR_{2L}$), and Gln-Gln-His-Phe-Arg-Thr-Pro-Phe-Thr ($CDR_{3L}$) according to SEQ ID No:4, or Lys-Ala-Ser-Gln-Asp-Ile-Lys-Lys-Tyr-Ile-Ala ($CDR_{1L}$), Tyr-Thr-Ser-Val-Leu-Gln-Pro ($CDR_{2L}$) and Leu-His-Tyr-Asp-Tyr-Leu-Tyr-Thr ($CDR_{3L}$) according to SEQ ID No.10 and 11.

Especially preferred are recombinant antibodies comprising a light chain variable domain of formula II, wherein the polypeptide residues of the framework regions $FR_5$, $FR_6$, $FR_7$ and $FR_8$ are those preferably occurring in mammalian, especially murine or human, antibodies.

In one embodiment of the invention, most preferred are recombinant antibodies wherein the light chain variable domain comprises a polypeptide of the amino acid sequence 136 to 241 of SEQ ID NO:4 and 5, wherein optionally one or more, e.g. 1, 2, 3 or 4, single amino acids within the amino acid sequences 136 to 158 ($FR_6$), 170 to 184 ($FR_7$), 192 to 223 ($FR_8$), and/or 233 to 241 ($FR_9$) are replaced by other amino acids or deleted, and wherein the amino acid Cys may be in the oxidized state forming S—S-bridges, in particular the recombinant antibodies with a light chain variable domain comprising a polypeptide of the amino acid sequence 136 to 241 of SEQ ID NO:4 and 5, wherein the amino acid Cys may be in the oxidized state forming S—S-bridges.

In a second embodiment of the invention, most preferred are recombinant antibodies wherein the light chain variable domain comprises a polypeptide of the amino acid sequence 137 to 241 of SEQ ID NO:10 and 11, wherein optionally one or more, e.g. 1, 2, 3 or 4 single amino acids within the amino acid sequences 137 to 159 ($FR_6$), 171 to 185 ($FR_7$), 193 to 224 ($FR_8$), and/or 233 to 241 ($F_9$) are replaced by other amino acids or deleted, and wherein the amino acid Cys may be in the oxidized state forming S—S-bridges, in particular the recombinant antibody wherein the light chain variable domain comprises a polypeptide of the amino acid sequence 137 to 241 of SEQ ID NO:10 and 11, wherein the amino acid Cys may be in the oxidized state forming S—S-bridges.

For example, amino acids within the framework regions may be replaced by other amino acids or deleted as detailed above for the heavy chain.

Especially preferred is a single-chain recombinant antibody wherein the heavy chain variable domain and the light chain variable domain are linked by way of a spacer group consisting of 10 to 30, e.g. around 15, amino acids, in particular a single-chain recombinant antibody comprising a polypeptide of the formula

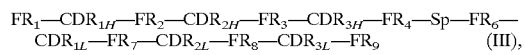

$$FR_1—CDR_{1H}—FR_2—CDR_{2H}—FR_3—CDR_{3H}—FR_4—Sp—FR_6—\\CDR_{1L}—FR_7—CDR_{2L}—FR_8—CDR_{3L}—FR_9 \qquad (III),$$

wherein $FR_1$, $CDR_{1H}$, $FR_2$, $CDR_{2H}$, $FR_3$, $CDR_{3H}$, $FR_4$, $FR_6$, $CDR_{1L}$, $FR_7$, $CDR_{2L}$, $FR_8$, $CDR_{3L}$ and $FR_9$ have the meanings as mentioned before and Sp is a peptide spacer consisting of about 10 to 30, e.g. around 15, amino acids; and wherein the heavy chain or the light chain variable domain is further connected to an effector molecule, e.g. an enzyme, such as phosphatase, particularly alkaline phosphatase, or a toxin, such as Pseudomonas exotoxin, or a variant thereof. Preferably, the effector molecule is connected to the light chain variable domain, optionally via a peptide spacer consisting of one or more, e.g. 1–10 amino acids.

These fusion proteins comprising a single-chain recombinant antibody and an effector molecule optionally comprise another peptide, e.g. a peptide facilitating purification, in particular a peptide being an epitope against which an antibody is available, such as the FLAG peptide. Purification, e.g. by means of affinity chromatography, of a fusion protein comprising such a peptide is advantageous e.g. in that it may be faster, more specific and/or gentler. The peptide may be placed at the N-terminus of the fusion protein, in between the recombinant antibody and the effector molecule, or at the C-terminus of the fusion protein. Preferably, it is located at the N-terminus or at the C-terminus, in particular at the N-terminus. Preferably, these constructs also contain a cleavage site, so that the fusion protein can be liberated therefrom, either by enzymatic cleavage, e.g. by enterokinase or by Factor Xa, or by the chemical methods known in the art. Furthermore these constructs may comprise a peptide spacer consisting of one or more, e.g. 1 to 10, in particular about 2 amino acids, said spacer facilitating the linkage of the above-mentioned peptide and/or the cleavage site to the recombinant antibody. The cleavage site is placed in such a way that the fusion protein comprising the recombinant antibody and the effector molecule can be easily liberated, if desired, preferably in vitro. For example, in the protein construct comprising the fusion protein designated Fv(FRP5)-ETA (cf. SEQ. ID NO:13 and 14), the FLAG peptide and an enterokinase cleavage site are linked to a spacer and placed in front of the Fv heavy chain/light chain variable domain and exotoxin A fusion protein. If desired, the FLAG peptide can be cleaved off by enterokinase, preferably after affinity purification of the protein, yielding a fusion protein comprising the single-chain antibody Fv(FRP5) and exotoxin A.

Most preferred is a single-chain recombinant antibody wherein the heavy chain variable domain and the light chain variable domain are derived from a mouse monoclonal antibody directed to the extracellular domain of the growth factor receptor c-erbB-2, e.g. derived from the mouse monoclonal antibodies FRP5, FSP16, FWP51 or FSP77, particularly from the mouse monoclonal antibodies FRP5 or FWP51. Likewise preferred is a single-chain recombinant antibody wherein the spacer group linking the light chain and the heavy chain variable domains is a polypeptide comprising about 15 amino acids selected from glycine and serine, in particular wherein the spacer group is the 15 amino acid polypeptide consisting of three repetitive subunits of Gly-Gly-Gly-Gly-Ser of SEQ ID NO:17.

Especially preferred is a single-chain antibody comprising the heavy chain variable domain of a mouse monoclonal antibody selected from the group consisting of FRP5, FSP16, FWP51 and FSP77, the 15 amino acid spacer group of SEQ ID NO:17 consisting of three repetitive subunits of Gly-Gly-Gly-Gly-Ser, the light chain variable domain of a mouse monoclonal antibody selected from the group consisting of FRP5, FSP16, FWP51 and FSP77 and an enzyme, for example a phosphatase such as the alkaline phosphatase phoA, or an exotoxin such as Pseudomonas exotoxin, or a variant thereof.

Particularly preferred is the particular single-chain recombinant antibody designated Fv(FRP5)-phoA comprising a polypeptide of the amino acid sequence 2 to 690 of SEQ ID NO:6 and 7.

Likewise preferred is a single-chain recombinant antibody comprising a peptide facilitating purification, a cleavage site and a particular single-chain recombinant antibody selected from the group consisting of Fv(FRP5)-ETA and Fv(FWP51)-ETA, in particular a single-chain recombinant antibody comprising a polypeptide selected from the group consisting of a polypeptide of the amino acid sequence −10 to 606 of SEQ ID NO:13 and 14 and of a polypeptide of the amino acid sequence −10 to 606 of SEQ ID NO:15 and 16, said protein being subjected to in vitro cleavage by enterokinase, if desired.

Particularly preferred is a single-chain recombinant antibody comprising a protein selected from the group consisting of a polypeptide of the amino acid sequence 2 to 606 of SEQ ID NO:13 and 14 and a polypeptide of the amino acid sequence 2 to 606 of SEQ ID NO:15 and 16.

The invention further concerns the mouse monoclonal antibodies directed to the extracellular domain of the growth factor receptor c-erbB-2 and designated FRP5, FSP16, FSP77, and FWP51, which are secreted by the hybridoma cell lines FRP5, FSP16, FSP77, and FWP51, respectively. Most preferred are the mouse monoclonal antibodies designated FRP5 and FWP51.

The invention further concerns a method of manufacture of the recombinant antibodies and of the mouse monoclonal antibodies of the invention. The antibodies are prepared by processes that are known per se, characterized in that host cells or hybridoma cells as defined further below producing such antibodies are multiplied in vitro or in vivo and, when required, the obtained antibodies are isolated. For example, the recombinant antibodies of the invention can be prepared by recombinant DNA techniques comprising culturing a transformed host under conditions which allow expression thereof and isolating said antibody.

More specifically, the present invention also relates to a process for the production of a protein of the invention selected from the group consisting of a heavy chain murine variable domain, a light chain murine variable domain, a heavy chain murine variable domain and a light chain murine variable domain, a single-chain recombinant antibody, a fusion protein, and a fusion protein optionally comprising a peptide facilitating purification, a cleavage site and a peptide spacer comprising culturing a host, e.g. E. coli, which has been transformed with a hybrid vector comprising an expression cassette comprising a promoter and a DNA coding for said protein which DNA is controlled by said promoter, and isolating said protein.

In particular, the present invention relates to a process for the production of a protein of the invention selected from the group consisting of a heavy chain murine variable domain, a light chain murine variable domain, a heavy chain murine variable domain and a light chain murine variable domain, a single-chain recombinant antibody, and a fusion protein optionally comprising a peptide facilitating purification, a cleavage site and a peptide spacer comprising culturing a host, e.g. E. coli, which has been transformed with a hybrid vector comprising an expression cassette comprising a promoter operably linked to a first DNA sequence encoding a signal peptide linked in the proper reading frame to a second DNA sequence encoding said protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antibodies, preferentially by immunofluorescent staining of cells expressing c-erbB-2, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with c-erbB-2 protein or with Protein-A.

The invention further concerns hybridoma cells secreting the monoclonal antibodies of the invention, in particular the hybridoma cell lines FRP5, FSP16, FSP77, and FWP51 deposited under the Budapest Treaty on Nov. 21, 1990 at the European Collection of Animal Cell Cultures (ECACC) in Porton Down, Salibury, UK, under the accession numbers 90112115, 90112116, 90112117, and 90112118, respectively. Most preferred is the hybridoma cell line designated FRP5, ECACC number 90112115 or the hybridoma cell line designated FWP51, ECACC number 90112118. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed to the extracellular domain of the growth factor receptor c-erbB-2, characterized in that a suitable mammal, for example a Balb/c mouse, is immunized with purified c-erbB-2 protein, an antigenic carrier containing purified c-erbB-2 or with cells bearing growth factor receptor c-erbB-2, antibody-producing cells of the immunized mammal are fused with cells of a suitable myeloma cell line, the hybrid cells obtained in the fusion are cloned, and cell clones secreting the desired antibodies are selected. For example spleen cells of Balb/c mice immunized with cells bearing c-erbB-2 are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterized in that Balb/c mice are immunized by injecting subcutaneously and/or intraperitoneally between $10^7$ and $10^8$ cells of the human breast tumor cell line SKBR3 containing a suitable adjuvant several times, e.g. four to six times, over several months, e.g. between two and four months, and spleen cells from the immunized mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunized mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant DNAs comprising an insert coding for a heavy chain murine variable domain and/or for a light chain murine variable domain of antibodies directed to the extracellular domain of the growth factor receptor c-erbB-2 as described hereinbefore. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain murine variable domain and/or for a light chain murine variable domain of antibodies directed to the extracellular domain of the growth factor receptor c-erbB-2 can be enzymatically or chemically synthezised DNA having the authentic DNA sequence coding for a heavy chain murine variable domain and/or for the light chain murine variable domain, or a mutant therof. A mutant of the authentic DNA is a DNA encoding a heavy chain murine variable domain and/or a light chain murine variable domain of the above-mentioned antibodies in which one or more amino acids are deleted or exchanged with one or more other amino acids. Preferably said modification(s) are outside the CDRs of the heavy chain murine variable domain and/or of the light chain murine variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

The invention relates to a recombinant DNA comprising an insert coding for a heavy chain murine variable domain of a monoclonal antibody selected from the group consisting of the antibodies FRP5, FSP16, FSP77 and FWP51, or coding for an amino acid sequence homologous to said heavy chain variable domain.

In particular, the invention concerns a recombinant DNA comprising an insert coding for a heavy chain murine variable domain, which originates from genomic DNA or mRNA of the hybridoma cell lines FRP5, FSP16, FSP77 or FWP51, or which is homologous to genomic DNA of said cell lines and codes for an amino acid sequence homologous to the heavy chain variable domain of monoclonal antibodies FRP5, FSP16, FSP77 or FWP51. Especially preferred is a recombinant DNA comprising an insert coding for a heavy chain murine variable domain, which originates from genomic DNA or mRNA of the hybridoma cell line FRP5, or which is homologous to genomic DNA of said cell line and codes for an amino acid sequence homologous to the heavy chain variable domain of monoclonal antibody FRP5; or a recombinant DNA comprising an insert coding for a heavy chain murine variable domain, which originates from genomic DNA or mRNA of the hybridoma cell line FWP51, or which is homologous to genomic DNA of said cell line and codes for an amino acid sequence homologous to the heavy chain variable domain of monoclonal antibody FWP51

Preferred is a recombinant DNA comprising an insert coding for the polypeptide of formula I, wherein $FR_1$, $FR_2$, $FR_3$, $FR_4$, $CDR_{1H}$, $CDR_{2H}$, and $CDR_{3H}$ have the meanings as mentioned hereinbefore, optionally further containing introns. Especially preferred is a recombinant DNA coding for the polypeptide of formula I comprising inserts coding for murine or human framework regions $FR_1$, $FR_2$, $FR_3$ and $FR_4$, and inserts coding for complementarity determining regions of the DNA sequence 99 to 113 ($CDR_{1H}$), the DNA sequence 156 to 206 ($CDR_{2H}$), and the DNA sequence 303 to 332 ($CDR_{3H}$) of SEQ ID NO:4 and 5 or coding for complementarity determining regions of the DNA sequence 99 to 113 (CDR$_{1H}$), the DNA sequence 156 to 206 (CDR$_{2H}$), and the DNA sequence 303 to 335 (CDR$_{3H}$) of SEQ ID NO:10 and 11. Most preferred is a DNA comprising an insert of the DNA sequence 9 to 365 of SEQ ID NO:4 and 5, wherein optionally one or more, e.g. 1 to 10, nucleotides are replaced by other nucleotides, in particular a DNA comprising an insert of the DNA sequence 9 to 365 of SEQ ID NO:4 and 5. Likewise preferred is a DNA comprising an insert of the DNA sequence 9 to 368 of SEQ ID NO:10 and 11, wherein optionally one or more, e.g. 1 to 10, nucleotides are replaced by other nucleotides, in particular a DNA comprising an insert of the DNA sequence 9 to 368 of SEQ ID NO:10 and 11.

In a DNA wherein nucleotides of the sequence given in SEQ ID NO:4 and 5, or in a DNA wherein nucleotides of the sequence given in SEQ ID NO:8, are replaced by other nucleotides, such replacement is preferred when it does not alter the amino acid sequence of the complementarity determining regions (CDRs) coded for. This means that such replacement of nucleotides may occur in the inserts coding for the framework regions (FRs) or in a position where it does not alter the amino acid coded for due to the degeneracy of the triplet codons.

Likewise the invention relates to a recombinant DNA comprising an insert coding for a light chain murine variable domain of a monoclonal antibody selected from the group consisting of the antibodies FRP5, FSP16, FSP77 and FWP51, or coding for an amino acid sequence homologous to said light chain variable domain.

More specifically, the invention concerns a recombinant DNA comprising an insert coding for a light chain murine variable domain, which originates from genomic DNA or mRNA of the hybridoma cell lines FRP5, FSP16, FSP77 or FWP51, or which is homologous to genomic DNA of said cell lines and codes for an amino acid sequence homologous to the light chain variable domain of monoclonal antibodies FRP5, FSP16, FSP77 or FWP51. Particularly preferred is a recombinant DNA comprising an insert coding for a light chain murine variable domain, which originates from genomic DNA or mRNA of the hybridoma cell line FRP5, or which is homologous to genomic DNA of said cell line and codes for an amino acid sequence homologous to the light chain variable domain of monoclonal antibody FRP5, or a recombinant DNA comprising an insert coding for a light chain murine variable domain, which originates from genomic DNA or mRNA of the hybridoma cell line FwP51, or which is homologous to genomic DNA of said cell line and codes for an amino acid sequence homologous to the light chain variable domain of monoclonal antibody FWP51.

Preferred is a recombinant DNA comprising an insert coding for the polypeptide of formula II, wherein FR$_5$, FR$_6$, FR$_7$, FR$_8$, CDR$_{1L}$, CDR$_{2L}$, and CDR$_{3L}$ have the meanings as mentioned hereinbefore, optionally further containing introns. Especially preferred is a recombinant DNA coding for the polypeptide of formula II comprising inserts coding for murine or human framework regions FR$_5$, FR$_6$, FR$_7$ and FR$_8$, and inserts coding for complementarity determining regions of the DNA sequence 480 to 512 (CDR$_{1L}$), the DNA sequence 558 to 578 (CDR$_{2L}$), and the DNA sequence 675 to 701 (CDR$_{3L}$) of SEQ ID NO:4 and 5, or coding for complementarity determining regions of the DNA sequence 483 to 515 (CDR$_{1L}$), the DNA sequence 561 to 581 (CDR$_{2L}$), and the DNA sequence 678 to 701 (CDR$_{3L}$) of SEQ ID NO:10 and 11.

Most preferred is a DNA comprising an insert of the DNA sequence 411 to 728 of SEQ ID NO:4 and 5, wherein optionally one or more, e.g. 1 to 10, nucleotides are replaced by other nucleotides, in particular a DNA comprising an insert of the DNA sequence 411 to 728 of SEQ ID NO:4 and 5. Likewise preferred is a DNA comprising an insert of the DNA sequence 414 to 728 of SEQ ID NO:10 and 11, wherein optionally one or more, e.g. 1 to 10, nucleotides are replaced by other nucleotides, in particular a DNA comprising an insert of the DNA sequence 414 to 728 of SEQ ID NO:10 and 11. In a DNA wherein nucleotides of the sequence given in SEQ ID NO:4 and 5, or in a DNA wherein nucleotides of the sequence given in SEQ ID NO:10 and 11, are replaced by other nucleotides, such replacement is preferred when it does not alter the amino acid sequence of the complementarity determining regions (CDRs) coded for, as is described above for DNA coding for the heavy chain variable domain.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant DNAs comprising an insert coding for a heavy chain murine variable domain of an antibody directed to the extracellular domain of c-erbB-2 fused to a human constant domain γ, for example γ1, γ2, γ3 or γ4, preferably γ1 or γ4. Likewise the invention concerns recombinant DNAs comprising an insert coding for a light chain murine variable domain of an antibody directed to the extracellular domain of c-erbB-2 fused to a human constant domain κ or λ, preferably κ.

The invention especially concerns recombinant DNAs coding for a single-chain recombinant antibody as defined hereinbefore, e.g. recombinant DNA wherein the heavy chain variable domain and the light chain variable domain are linked by way of a DNA insert coding for a spacer group, in particular a recombinant DNA coding for a protein of the formula III, wherein FR$_1$,FR$_2$,FR$_3$,FR$_4$,FR$_6$,FR$_7$,FR$_8$,FR$_9$, SP, CDR$_{1H}$,CDR$_{2H}$,CDR$_{3H}$, CDR$_{1L}$, CDR$_{2L}$ and CDR$_{3L}$ have the meanings given above, optionally comprising further DNA coding for an effector molecule and/or signal sequences facilitating the processing of the antibody in the host cell. In particular the invention concerns a DNA comprising an insert of the DNA sequence 9–728 of SEQ ID NO:4 and 5, wherein optionally one or more, e.g. 1 to 10, nucleotides are replaced by other nucleotides, especially a DNA comprising an insert of the DNA sequence 9 to 728 of SEQ ID NO:4 and 5. Furthermore the invention relates to a DNA comprising an insert of the DNA sequence 9–728 of SEQ ID NO:10 and 11 wherein optionally one or more, e.g. 1 to 10, nucleotides are replaced by other nucleotides, especially a DNA comprising an insert of the DNA sequence 9 to 728 of SEQ ID NO:10 and 11.

In another embodiment the invention pertains to recombinant DNAs coding for a recombinant DNA wherein the heavy chain variable domain and the light chain variable domain are linked by way of a DNA insert coding for a spacer group, optionally comprising a signal sequence facilitating the processing of the antibody in the host cell and/or a DNA coding for a peptide facilitating the purification of the antibody and/or a DNA coding for a cleavage site and/or a DNA coding for a peptide spacer and/or a DNA coding for an effector molecule.

The DNA coding for an effector molecule is intended to be a DNA coding for the above-mentioned effector molecules, particularly a DNA coding for alkaline phosphatase or Pseudomonas exotoxin A. The DNA encoding such an effector molecule has the sequence of a naturally occurring enzyme or toxin encoding DNA, or a mutant therof, and can be prepared by methods well known in the art. A mutant of the naturally occurring DNA encoding e.g. alkaline phosphatase or Pseudomonas exotoxin A, or a variant thereof can be obtained e.g. analogously to the methods described above.

Most preferred is a DNA comprising an insert of the DNA sequence 23 to 814 of SEQ ID NO:5, of the DNA sequence 86 to 2155 of SEQ ID NO:6 and 7 or of the DNA sequence 23 to 2155 of SEQ ID NO:6 and 7, wherein optionally one or more, e.g. 1 to 10, nucleotides are replaced by other nucleotides, in particular a DNA comprising an insert of the DNA sequence 23 to 2155 of SEQ ID NO:6 and 7.

Equally preferred is a DNA comprising an insert of the DNA sequence 1 to 1911 of SEQ ID NO:13 and 14, of the DNA sequence 64 to 1911 of SEQ ID NO:13 and 14, or of the DNA sequence 97 to 1911 of SEQ ID NO: 10, wherein optionally one or more, e.g. 1 to 10, nucleotides are replaced by other nucleotides, in particular a DNA comprising an insert of the DNA sequence 1 to 1911 of SEQ IDs NO: 13 and 14; or a DNA comprising an insert of the DNA sequence 1 to 1911 of SEQ ID NO:15 and 16, of the DNA sequence 64 to 1911 of SEQ ID NO:15 and 16, of the DNA sequence 96 to 1911 of SEQ ID NO:15 and 16, or of the DNA sequence 97 to 1911 of SEQ ID NO:15 and 16, wherein optionally one or more, e.g. 1 to 10, nucleotides are replaced by other nucleotides, in particular a DNA comprising an insert of the DNA sequence 1 to 1911 of SEQ ID NO: 15 and 16.

Furthermore the invention concerns a recombinant DNA which is a hybrid vector comprising an insert coding for the variable domain of a murine heavy chain as described hereinbefore and/or an insert coding for the variable domain of a murine light chain as described hereinbefore, an origin of replication or an autonomously replicating sequence, one or more dominant marker sequences and, optionally, expression control sequences, signal sequences and additional restriction sites.

In a first embodiment the hybrid vector according to the invention comprises an expression cassette comprising a promoter and a DNA coding for a protein of the invention selected from the group consisting of a heavy chain murine variable domain, a light chain murine variable domain, a heavy chain murine variable domain and a light chain murine variable domain, a single-chain recombinant antibody, a fusion protein, and a fusion protein optionally comprising a peptide facilitating purification, a cleavage site and a peptide spacer, which DNA is controlled by said promoter, and isolating said protein.

In a second embodiment, the hybrid vector according to the invention comprises an expression cassette comprising a promoter operably linked to a first DNA sequence encoding a signal peptide linked in the proper reading frame to a second DNA sequence encoding a protein of the invention selected from the group consisting of a heavy chain murine variable domain, a light chain murine variable domain, a heavy chain murine variable domain and a light chain murine variable domain, a single-chain recombinant antibody, and a fusion protein optionally comprising a peptide facilitating purification, a cleavage site and a peptide spacer.

Vectors typically perform two functions in collaboration with compatible host cells. One function is to facilitate the cloning of the nucleic acid that encodes the immunoglobulin variable domains, i.e. to produce usable quantities of the nucleic acid (cloning vectors). The other function is to provide for replication and expression of the recombinant gene constructs in a suitable host, either by maintenance as an extrachromosomal element or by integration into the host chromosome (expression vectors). A cloning vector comprises the recombinant gene constructs as described above, an origin of replication or an autonomously replicating sequence, dominant marker sequences and, optionally, signal sequences and additional restriction sites. An expression vector additionally comprises expression control sequences essential for the transcription and translation of the recombinant genes.

An origin of replication or an autonomously replicating sequence is provided either by construction of the vector to include an exogeneous origin such as derived from Simian virus 40 (SV 40) or another viral source, or by the host cell chromosomal mechanisms.

The markers allow for selection of host cells which contain the vector. Selection markers include genes which confer resistance to heavy metals such as copper or to antibiotics such as geneticin (G-418) or hygromycin, or genes which complement a genetic lesion of the host cell such as the absence of thymidin kinase, hypoxanthine phosphoryl transferase, dihydrofolate reductase or the like.

Signal sequences may be, for example, presequences or secretory leaders directing the secretion of the recombinant antibody, splice signals, or the like. Examples for signal sequences directing the secretion of the recombinant antibody are sequences derived from the ompA gene, the pelB (pectate lyase) gene or the phoA gene.

As expression control sequences, the vector DNA comprises a promoter, sequences necessary for the initiation and termination of transcription and for stabilizing the mRNA and, optionally, enhancers and further regulatory sequences.

A wide variety of promoting sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of viral origin, e.g. derived from Simian virus, polyoma virus, bovine papilloma virus or Moloney sarcoma virus, or of genomic, especially murine, origin.

The various DNA segments of the vector DNA are operationally linked, i.e. they are contiguous and placed into a functional relationship with each other. Examples of vectors which are suitable for replication and expression in an E. coli strain are bacteriophages, for example derivatives of λ bacteriophages, or plasmids, such as, in particular, the plasmid ColE1 and its derivatives, for example pMB9, pSF2124, pBR317 or pBR322 and plasmids derived from pBR322, such as pUC9, pUCK0, pHRi148 and pLc24. Suitable vectors contain a complete replicon, a marker gene, recognition sequences for restriction endonucleases, so that the foreign DNA and, if appropriate, the expression control sequence can be inserted at these sites, and optionally signal sequences and enhancers.

Microbial promoters are, for example, the strong leftward promoter $P_L$ of bacteriophage λ which is controlled by a temperature sensitive repressor. Also suitable are E. coli promoters such as the lac (lactose) promoter regulated by the lac repressor and induced by isopropyl-β-D-thiogalactoside, the trp (tryptophan) promoter regulated by the trp repressor and induced e.g. by tryptophan starvation, and the tac (hybrid trp-lac promoter) regulated by the lac repressor.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the 2μ (2 mikron) plasmid DNA from *Saccharomyces cerevisiae* can be used. Such vectors will get integrated by recombination into 2μ plasmids already existing within the cell, or replicate autonomously. 2μ sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Vectors suitable for replication and expression in mammalian cells are preferably provided with promoting sequences derived from DNA of viral origin, e.g. from Simian virus 40 (SV40), Rous sarcoma virus (RSV), adenovirus 2, bovine papilloma virus (BPV), papova-virus BK mutant (BKV), or mouse or human cytomegalovirus (CMV). Alternatively, the vectors may comprise promoters from mammalian expression products, such as actin, collagen, myosin etc., or the native promoter and control sequences which are normally associated with the desired gene sequence, i.e. the immunoglobulin H-chain or L-chain promoter.

Preferred vectors are suitable for both procaryotic and eucaryotic hosts and are based on viral replication systems. Particularly preferred are vectors comprising Simian virus promoters, e.g. pSVgpt or pSVneo, further comprising an enhancer, e.g. an enhancer normally associated with the immunoglobulin gene sequences, in particular the mouse Ig H- or L-chain enhancer.

The recombinant DNA coding for a recombinant antibody of the invention can be prepared, for example, by culturing a transformed host cell and optionally isolating the prepared DNA.

In particular, such DNA can be prepared by a method comprising a) preparing murine DNA coding for the variable heavy and/or light chain domains of the antibody with the desired specificity, e.g. by isolating the DNA from the genome of a suitable hybridoma cell line and selecting the desired DNA using DNA probes, or by isolating mRNA from a suitable hybridoma cell line and preparing cDNA coding for the variable heavy and/or light chain domains of the antibody with the desired specificity using oligonucleotide primers, b) preparing DNA coding for the desired signal sequence and/or preparing DNA coding for an effector molecule, e.g. by isolating the desired DNA(s) from a suitable source, e.g. from a genomic library or a cDNA library using DNA probes, c) synthesizing DNA coding for the desired spacer group by chemical methods, d) constructing recombinant genes encoding the recombinant antibodies by incorporating the DNA of step a) and, optionally, b) and/or c) into appropriate hybrid vectors, e) transferring the obtained hybrid vectors into a recipient host cell or retrieving the DNA coding for the recombinant genes and transferring the unlinked DNA into a recipient host cell, f) selecting and culturing the transformed host cell, and g) optionally isolating the desired DNA.

The DNA according to step a) of the process described above can be obtained by isolation of genomic DNA or by preparation of cDNA from isolated mRNA. Genomic DNA from hybridoma cells is isolated by methods known in the art which include steps for disruption of the cells, e.g. by lysis in presence of detergents like Triton™, extracting the DNA, e.g. by treatment with phenol and $CHCl_3$/isoamyl alcohol, and precipitation of DNA. The DNA is fragmented, conveniently by one or more restriction endonucleases, the resulting fragments are replicated on a suitable carrier, e.g. nitrocellulose membranes, and screened with a DNA probe for the presence of the DNA sequences coding for the polypeptide sequence of interest, in particular for the presence of the rearranged H- and L-chain Ig gene loci. By this procedure DNA fragments are found that contain inserts with heavy chain V, D and J regions and light chain V and J regions, respectively, together with a leader sequence and introns, if any. cDNA from hybridoma cells is likewise prepared by methods known in the art, e.g. by extracting total cellular RNA, isolating mRNA by a suitable chromatographic method, e.g. chromatography on oligo(dT)-cellulose, synthesizing cDNA with a mixture of deoxynucleotide triphosphates and reverse transcriptase in the presence of oligonucleotide primers complementary to suitable regions in the murine immunoglobulin heavy and light chain constant domain genes, and isolating the cDNA. As a tool simplifying DNA isolation, the desired genomic DNA or cDNA may be amplified using polymerase chain reaction (PCR) technology. PCR involves repeated rounds of extension from two primers specific for DNA regions at each end of the gene.

Preferably, cDNA transcripts of total mRNA from the suitable hybridoma cell line is treated in a heating/cooling cycle with Taq DNA polymerase in the presence of primers tailored to hybridize to Ig H- and L-chain variable domains, respectively.

Genomic DNA or cDNA according to step b) of the process described above is isolated from suitable bacterial or mammalian cells according to methods known in the art. Preferably, the methods as described under a) are used, substituting the corresponding source cells for the murine hybridoma cells and using DNA probes designed to hybridize with the desired signal sequences or the genes coding for the desired effector molecules. In bacteria wherein separation of mRNA from total RNA is not possible with olig(dT)-cellulose, cDNA is prepared from total RNA using corresponding oligonucleotide primers. The DNA isolation is simplified considerably by the PCR technology.

DNA according to step c) is prepared by conventional chemical and enzymatic methods, e.g. by chemical synthesis of oligonucleotides of between thirty and sixty bases with overlapping complementary sequences, hybridization of such oligonucleotides, and enzymatic ligation, optionally after filling-in of missing bases with suitable enzymes in the presence of the corresponding deoxynucleotide triphosphates.

The DNA probe for the mouse variable chain domains may be a synthetic DNA, a cDNA derived from mRNA coding for the desired immunoglobulin or a genomic DNA or DNA fragment of known nucleotide sequence. As probes for the detection and/or amplification of the rearranged Ig gene loci of the variable domains of L-/H-chains, DNA fragments of known nucleotide sequences of adjacent conserved variable or constant domains are selected which constitute the Ig loci of the L-/H-chain in the mammal from which the DNA is derived, e.g. Balb/c mice. The DNA probe is synthesized by chemical methods or isolated from suitable tissue of an appropriate mammal, e.g. Balb/c mouse liver, and purified by standard methods. If required, the probe DNA is labelled, e.g. radioactively labelled by the well-known nick-translation technique, then hybridized with the DNA library in buffer and salt solutions containing adjuncts, e.g. calcium chelators, viscosity regulating compounds, proteins, non-specific DNA and the like, at temperatures favoring selective hybridization.

Once a fragment has been identified which contains the desired DNA sequence, this fragment may be further manipulated to remove nonessential DNA, modified at one or both termini, and treated to remove all or a portion of intervening sequences, or the like.

The joining of the various DNA fragments in order to produce recombinant genes encoding the recombinant antibodies is performed in accordance with conventional techniques, for example, by blunt- or staggered-end ligation, restriction enzyme digestion to provide for appropriate cohesive termini, filling-in cohesive ends as appropriate, alkaline phosphatase treatment to avoid undesirable joining, and ligation with appropriate ligases.

The transfer of the recombinant DNAs, e.g. the transfer of hybrid vectors, and the selection of transformed cells is described below.

Moreover, the invention relates to host cells transformed with the recombinant DNAs described above, namely host cells which are transformed with a DNA encoding the heavy chain and/or a DNA encoding the light chain of the desired recombinant antibody, in particular host cells transformed with a DNA encoding the preferred single-chain recombinant antibody.

More specifically, the invention concerns a host cell which has been transformed with a hybrid vector comprising an expression cassette comprising a promoter and a DNA coding for a protein of the invention selected from the group consisting of a heavy chain murine variable domain, a light chain murine variable domain, a heavy chain murine variable domain and a light chain murine variable domain, a single-chain recombinant antibody, a fusion protein, and a fusion protein further comprising a peptide facilitating purification, a cleavage site and a peptide spacer which DNA is controlled by said promoter.

Furthermore, the invention pertains to a host cell which has been transformed with a hybrid vector comprising an expression cassette comprising a promoter operably linked to a first DNA sequence encoding a signal peptide linked in the proper reading frame to a second DNA sequence encoding a protein of the invention selected from the group consisting of a heavy chain murine variable domain, a light chain murine variable domain, a heavy chain murine variable domain and a light chain murine variable domain, a single-chain recombinant antibody, a fusion protein, and a fusion protein further comprising a peptide facilitating purification, a cleavage site and a peptide spacer.

In particular, the present invention relates to a process for the production of a protein of the invention selected from the group consisting of a heavy chain murine variable domain, a light chain murine variable domain, a heavy chain murine variable domain and a light chain murine variable domain, a single-chain recombinant antibody, a fusion protein, and a fusion protein further comprising a peptide facilitating purification, a cleavage site and a peptide spacer comprising culturing a host, e.g. E. coli, which has been transformed with a hybrid vector comprising an expression cassette comprising a promoter operably linked to a first DNA sequence encoding a signal peptide linked in the proper reading frame to a second DNA sequence encoding said protein, and isolating said protein. The host cells of the present invention have to be capable of culture in vitro. Suitable host cells are of procaryotic or of eucaryotic origin and are, for example, bacterial cells, e.g. E. coli, yeasts, e.g. Saccharomyces cerevisiae, or mammalian cells. For the preparation of functional chimeric human/mouse antibodies the host cells have to be of higher eucaryotic origin to provide a suitable environment for the production of active antibodies, since the biosynthesis of functional tetrameric antibody molecules requires correct nascent polypeptide chain folding, glycosylation, and assembly.

Examples of suitable hosts are microorganisms which are devoid of or poor in restriction enzymes or modification enzymes, such as bacteria, in particular strains of *Escherichia coli*, for example *E. coli* X1776, *E. coli* Y1090, *E. coli* HB 101, *E. coli* W3110, *E. coli* HB 101/LM1035, *E. coli* JA 221, *E. coli* DH5α, *E. coli* K12, or *E. coli* CC118 strain, *Bacillus subtilis, Bacillus stearothermophilus,* Pseudomonas, Haemophilus, Streptococcus and others, and yeasts, for example *Saccharomyces cerevisiae* such as *S. cerevisiae* GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells, or cells of lymphoid origin, such as lymphoma, myeloma, hybridoma, trioma or quadroma cells, for example PAI, Sp2/0 or X63-Ag8.653 cells.

The above mentioned strains of *E. coli,* in particular *E. coli* CC118, are preferred as hosts.

The invention also concerns processes for the preparation of transformed host cells wherein suitable recipient host cells as described hereinbefore are transformed with a hybrid vector according to the invention, and the transformed cells are selected.

Transformation of microorganisms is carried out as described in the literature, for example for *S. cerevisiae* (A. Hinnen et al., Proc. Natl. Acad. Sci. USA 75: 1929, 1978), for *B. subtilis* (Anagnostopoulos et al., J. Bacteriol. 81: 741, 1961), and for *E. coli* (M. Mandel et al., J. Mol. Biol. 53: 159, 1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eucaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected, for example, by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The host cells are transformed with the recombinant L-chain gene construct alone, with the recombinant H-chain gene construct alone, with both, either sequentially or simultaneously, or by using, a vector construct comprising both the L-chain and H-chain genes, for example a recombinant single-chain antibody gene construct as indicated hereinbefore.

Preferred are host cells transformed with a recombinant single-chain antibody gene construct comprising DNA coding for the heavy chain variable domain of an anti-c-erbB-2 antibody, DNA coding for a spacer group, DNA coding for the light chain variable domain of an anti-c-erbB-2 antibody and DNA coding for an effector molecule, in particular transfected with the preferred recombinant single-chain antibody gene construct as indicated hereinbefore. Further examples of host cells of the invention are cells transfected with similar recombinant plasmids which contain alternative orientations of the H- and L-chain gene constructs, and those incorporating additional DNA elements to facilitate high levels of expression of the recombinant antibodies.

The host cells of the invention are genetically stable, secrete recombinant antibodies of the invention of constant specificity and can be activated from deep-frozen cultures by thawing and recloning.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of said amino acid is used to culture the transformed cells.

Cells of higher eucaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum titer of the polypeptide or derivative of the invention is obtained. Thus, an *E. coli* or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

When the cell density has reached a sufficient value, the culture is interrupted and the polypeptide or derivative can be isolated. If the hybrid vector contains a suitable secretion signal sequence, the polypeptide or derivative is secreted by the transformed cell directly into the culture medium. Otherwise, the cells have to be destroyed, for example by treatment with a detergent such as SDS, NP-40™, Triton™ or deoxycholic acid, lysed with lysozyme or a similarly acting enzyme, or disrupted by an osmotic shock or ultrasound. Break-up of the cells will also be required if the signal sequence directs the secretion of the desired protein into the cell periplasm. If yeast is used as a host microorganism, the cell wall may be removed by enzymatic digestion with a glucosidase. Alternatively or additionally, mechanical forces, such as shearing forces (e.g. French press, Dyno mill and the like) or shaking with glass beads or aluminium oxide, or alternating freezing, for example in liquid nitrogen, and thawing, for example at 30° C. to 40° C., as well as ultra-sound can be used to break the cells.

The cell supernatant or the solution obtained after centrifugation of the mixture obtained after breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides and derivatives of the invention are precipitated, for example, by saturation of the solution with ammonium sulfate or with other salts. Otherwise, the cell supernatant or lysate is directly pre-purified by filtering through suitable membranes and/or with chromatographic methods, for example affinity chromatography.

The recombinant antibodies and the monoclonal antibodies according to the invention can be used for the qualitative and quantitative determination of the extracellular domain of the growth factor receptor c-erbB-2. This is especially useful for the monitoring of tumor progression, for the decision whether a tumor is amenable to treatment with the recombinant or monoclonal antibodies of the invention, and for monitoring the treatment of tumor with chemotherapy. Tumors considered are those over-expressing c-erbB-2, for example breast and ovarian tumors.

In general, the monoclonal and the recombinant antibodies according to the invention can be used in any of the known immunoassays which rely on the binding interaction between the antibodies and the antigen, i.e. the extracellular domain of the c-erbB-2 protein. Examples of such assays are radio-, enzyme, fluorescence, chemiluminescence, immunoprecipitation, latex agglutination, and hemagglutination immunoassays, and, in particular, immunostaining methods.

The antibodies according to the invention can be used as such or in the form of enzyme-conjugated derivatives in an enzyme immunoassay. Any of the known modifications of an enzyme immunoassay can be used, for example soluble phase (homogeneous) enzyme immunoassay, solid phase (heterogeneous) enzyme immunoassay, single enzyme immunoassay or double (sandwich) enzyme immunoassay with direct or indirect (competitive) determination of the c-erbB-2 protein.

An example of such an enzyme immunoassay is a sandwich enzyme immunoassay in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with a monoclonal antibody of the invention by simple adsorption or optionally after activation of the carrier, for example with glutaraldehyde or cyanogen bromide. Then test solutions containing the soluble c-erbB-2 protein and finally single-chain recombinant antibodies of the invention comprising a detectable enzyme, e.g. alkaline phosphatase, are added. The amount of the soluble c-erbB-2 protein in the test solution is directly proportional to the amount of bound recombinant antibody and is determined by adding an enzyme substrate solution. The enzyme substrate reaction results, for example, in a color change which can be observed by eye or with optical measuring devices.

The antibodies according to the invention can be used as such or in the form of radioactively labelled derivatives in a radioimmunoassay (RIA). As described above for enzyme immunoassays, any of the known modifications of a radioimmunoassay can be used.

The tests are carried out in an analogous manner to the enzyme immunoassays described above using a radioactive label, e.g. $^{125}I$, instead of an enzyme label. The amount of immune complex formed which corresponds to the amount of c-erbB-2 protein present in the test solutions is determined by measuring the radioactivity of the immune complex.

For immunostaining cryosections of cryopreserved biopsy material or paraffin embedded tissue sections are treated with a solution containing a recombinant antibody of the invention comprising a detectable enzyme. Bound recombinant antibody is detected by treatment with a suitable enzyme substrate, preferably an enzyme substrate which leads to a solid deposit (stain) at the site of the recombinant antibody of the invention. In place of recombinant antibodies comprising an enzyme, a recombinant antibody comprising streptavidin and a solution of a biotin-enzyme-conjugate may be used, which leads to higher enzyme concentration at the site of the antibody and hence increased sensitivity of the immunostaining method. The solid deposit of the enzyme substrate is detected by inspection with a microscope, for example with a fluorescence microscope, or by scanning the optical density at the wavelength of the stain.

The use according to the invention of recombinant and/or monoclonal antibodies as described hereinbefore for the determination of c-erbB-2 protein also includes other immunoassays known per se, for example immunofluorescence assays, latex agglutination with antibody-coated or antigen coated latex particles, hemagglutination with antibody-coated or antigen-coated red blood corpuscles, evanescent light assays using an antibody-coated optical fibre and other direct-acting immunosensors which convert the binding event into an electrical or optical signal, or the like.

The invention also concerns test kits for the qualitative and quantitative determination of c-erbB-2 protein comprising recombinant antibodies of the invention and/or monoclonal antibodies of the invention and, optionally, adjuncts.

Test kits according to the invention for an enzyme immunoassay contain, for example, a suitable carrier, optionally freeze-dried solutions of a monoclonal antibody, optionally freeze-dried or concentrated solutions of a recombinant antibody comprising an enzyme or streptavidin, solutions of an enzyme-biotin conjugate if a recombinant antibody comprising streptavidin is used, enzyme substrate in solid or dissolved form, standard solutions of c-erbB-2 protein, buffer solutions, and, optionally, polypeptides or detergents for preventing non-specific adsorption and aggregate formation, pipettes, reaction vessels, calibration curves, instruction manuals and the like.

Test kits according to the invention for immunostaining contain, for example, optionally freeze-dried or concentrated solutions of a recombinant antibody comprising an enzyme or streptavidin, solutions of an enzyme-biotin conjugate if a recombinant antibody comprising streptavidin is used, enzyme substrate in solid or dissolved form, buffer solutions, and, optionally, pipettes, reaction vessels, calibration curves, instruction manuals and the like.

The recombinant and monoclonal antibodies of the invention can be used for the qualitative and quantitative determination of c-erbB-2 protein. Due to the fact that the growth factor receptor c-erbB-2 is overexpressed in certain tumor types, for example breast and ovarian tumors, the antibodies are particularly well suited for detection and monitoring of the mentioned tumors. In addition, radiolabelled derivatives of the antibodies of the invention may be used for the in vivo localization of tumors in a patient using radioscanning techniques. To that end, radiolabelled derivatives of antibodies of the invention are injected into the patient, and the patient scanned with a gamma imager at regular intervals. Cells over-expressing the growth factor receptor c-erbB-2 will take up more radioactive antibodies than other tissue and will be clearly recognized by the gamma imaging camera. Preferentially recombinant or monoclonal antibodies labelled with $^{131}I$ or with $^{99m}Tc$ are used for radioscanning in amounts of 3 to 8 µg representing 15 to 30 µCi per kg body weight.

The antibodies of the invention can further be used for the isolation and purification of the c-erbB-2 protein from natural sources or from transformed host cells by immunoaffinity chromatography.

Furthermore, the monoclonal antibodies and the recombinant antibodies of the invention, in particular recombinant antibodies comprising an effector molecule, especially a toxin, in particular Pseudomonas exotoxin, are useful for the treatment of patients with tumors over-expressing the growth factor receptor c-erbB-2, for example breast or ovarian tumors. If it is desired, tumor therapy may comprise applying more than one, e.g. two different, antibodies of the invention, for example applying both FRP5 and FWP51. The recombinant antibodies comprising a phosphatase may be used in connection with a phosphorylated prodrug such as mitomycin phosphate or etoposide phosphate, thus enabling the conversion of the active drug to the prodrug at the site of the tumor.

The invention therefore also concerns pharmaceutical compositions for treating tumors over-expressing the growth factor receptor c-erbB-2 comprising a therapeutically effective amount of a recombinant antibody or of a monoclonal antibody according to the invention and a pharmaceutically acceptable carrier. Preferred are pharmaceutical compositions for parenteral application. Compositions for intramuscular, subcutaneous or intravenous application are e.g. isotonic aqueous solutions or suspensions, optionally prepared shortly before use from lyophilized or concentrated preparations. Suspensions in oil contain as oily component the vegetable, synthetic or semi-synthetic oils customary for injection purposes. The pharmaceutical compositions may be sterilized and contain adjuncts, e.g. for conserving, stabilizing, wetting, emulsifying or solubilizing the ingredients, salts for the regulation of the osmotic pressure, buffer and/or compounds regulating the viscosity, e.g. sodium carboxycellulose, carboxymethylcellulose, sodium carboxymethylcellulose, dextran, polyvinylpyrrolidine or gelatine.

The pharmaceutical compositions of the invention contain from approximately 0.01% to approximately 50% of active ingredients. They may be in dosage unit form, such as ready-to-use ampoules or vials, or also in lyophilized solid form.

In general, the therapeutically effective dose for mammals is between approximately 5 and 25 µg of a recombinant antibody of the invention or of a monoclonal antibody of the invention per kg body weight depending on the type of antibody, the status of the patient and the mode of application. The specific mode of administration and the appropriate dosage will be selected by the attending physician taking into account the particulars of the patient, the state of the disease, the type of tumor treated, and the like. The pharmaceutical compositions of the invention are prepared by methods known in the art, e.g. by conventional mixing, dissolving, confectioning or lyophilizing processes. Pharmaceutical compositions for injection are processed, filled into ampoules or vials, and sealed under aseptic conditions according to methods known in the art.

The invention particularly concerns the monoclonal antibodies, the hybridoma cell lines, the recombinant single-chain antibodies, the recombinant DNAs, the transformed host cells, and the methods for the preparation thereof as described in the Examples. The following examples illustrate the invention but do not limit it to any extent.

Abbreviations

| | |
|---|---|
| ATP | adenosine triphosphate |
| BSS | Earle's balanced salt solution |
| BSA | bovine serum albumin |
| DEAE | diethylaminoethyl |
| DMEM | Dulbecco's modified Eagle's medium |
| dNTP | deoxynucleotide triphosphate |
| DTT | dithiothreitol |
| EDTA | disodium ethylenediaminetetraacetate |
| EGF | epidermal growth factor |
| EGTA | ethyleneglycol-bis-(β-aminoethyl ether)-N,N,N',N'-tetraacetic acid |
| FCS | fetal calf serum |
| HAT medium | hypoxanthine, aminopterin and thymidine medium |
| HEPES | N-2-hydroxyethylpiperazine-N'-2-ethanesulfonic acid |
| HT medium | hypoxanthine and thymidine medium |
| Ig | immunoglobulin |
| IPTG | isopropyl-β-thiogalactoside |
| MAb | monoclonal antibody |
| PBS | phosphate-buffered saline |
| PCR | polymerase chain reaction |
| PMSF | phenylmethylsulfonyl fluoride |
| SDS-PAGE | sodium dodecyl sulfate-polyacrylamide gel electrophoresis |
| Tris | Tris-(hydroxymethyl)-aminomethane |
| U | unit |
| $V_L$ | light chain variable domain |
| $V_H$ | heavy chain variable domain |
| XP | 5-bromo-4-chloro-3-indolyl phosphate p-toluidine salt |

EXAMPLES

Example 1

Preparation of Hybridoma Cell Lines FRP5, FSP16, FWP51 and FSP77

1.1 Source of antigen and immunization of Balb/c mice: The SKBR3 human breast tumor cell line (ATCC HTB 30), isolated in 1970 from a pleural effusion of a breast cancer patient, expresses approximately $1\times10^6$ molecules of the c-erbB-2 receptor protein per cell. $20\times10^6$ SKBR3 cells in PBS are injected subcutaneously and/or intraperitoneally into Balb/c mice. The cells are mixed 1:1 (v/v) with complete Freund's adjuvant. The injections are repeated a total of five times over the period of approximately 3 months replacing Freund's incomplete adjuvant for complete adjuvant. The final injection of cells is given three days before the fusion.

1.2 Cell fusion: Immunized mice are sacrificed and their splenocytes fused according to conventional methods (Koehler & Milstein, Nature 256: 495, 1976). Spleen cells are mixed at a 5:1 to 10:1 ratio with the fusion partner, the mouse myeloma cell line PAI (Stoker et al., Research Disclosure #21713, 1982), in the presence of 41% polyethylene glycol 4000 (Merck). Fused cells are plated at a density of $1\times10^6$ cells per well in 24-well microtiter plates on peritoneal macrophages and fed 3 times per week with standard HAT selection medium for 2 weeks followed by 2 weeks of HT medium. When the growth of hybridoma cells becomes visible, the supernatants are screened as described in Example 1.3. Positive hybridomas are cloned and stored.

1.3 Antibody detection in hybridoma supernatants: Culture fluids of growing hybridomas are tested for the presence of anti-c-erbB-2 antibody using a protocol involving two steps, immunofluorescence and immunoprecipitation.

1.3.1 Immunofluorescence: In the first step, hybridoma supernatants are tested for their immunofluorescent staining of mouse cells expressing high levels of the human c-erbB-2 protein. To isolate these cells the HC11 mouse mammary epithelial cell line (Ball et al., EMBO J. 7: 2089, 1988) is transfected according to conventional, previously described methods (Graham & van der Eb, Virology 52: 456, 1973) with a plasmid expressing the human c-erbB-2 protein (Masuko et al., Jpn. Cancer Res. 80: 10, 1989) and with the plasmid pSV2neo (Southern & Berg, J. Mol. Appl. Genet. 1: 327, 1982) which encodes the gene for resistance to the drug G418. Transfected cells are selected 2 weeks in medium containing 200 µg/ml G418 (Geneticin, Gibco-BRL). Individual clones are selected and analyzed for expression of the human c-erbB-2 protein using conventional protein blotting techniques (Towbin et al., Proc. Natl. Acad. Sci. USA 76: 4350, 1979). A clone expressing high levels of the human c-erbB-2 protein (clone R1#11) is selected and used in the immunofluorescent assay. Non-transfected HC11 cells serve as control cells.

The assay is done in the following manner: The cells (R1#11 or HC11) are grown in RPMI medium containing 8% heat inactivated FCS (Amimed), 10 ng/ml EGF (Inotech) and 5 µg/ml insulin (Sigma) for 1–2 days on fibronectin (Boehringer Mannheim) coated cover slips. Fibronectin coated cover slips are prepared and stored at room temperature and they are used routinely for screening. The coverslips are rinsed in PBS containing calcium and magnesium and fixed by treatment for 10 min with 3.7% formaldehyde (v/v in PBS). To reduce the non-specific binding the coverslips are incubated 20 min in PBS containing 3% BSA (Sigma). The coverslips are washed in PBS and in water, then allowed to dry at room temperature. 20–30 μl of hybridoma supernatants are added to circled areas on a coverslip which is incubated 1–2 h at room temperature in a humified atmosphere. The coverslips are then washed three times with PBS containing 0.05% Triton-X100™ (Fluka) and incubated an additional hour with anti-mouse Ig, fluorescein-linked whole antibody from sheep (Amersham). After three washes with PBS and one wash with water the cells are screened for fluorescence using a fluorescence microscope and a water immersion lens. Those hybridoma supernatants which are positive are screened in the second step described in Example 1.3.2.

1.3.2 Immunoprecipitation and protein blotting analysis: The SKBR3 human breast tumor cells express approximately $1 \times 10^6$ molecules of the c-erbB-2 protein per cell. A cell lysate is prepared by extracting approximately $4 \times 10^6$ cells in 1 ml of buffer containing 1% Triton-X100™ (Fluka), 50 mM Tris-HCl, pH 7.5, 5 mM EGTA, 0.15 M NaCl, 1 mM PMSF (Boehringer Mannheim), 80 μg/ml aprotinin (Boehringer Mannheim), 50 μg/ml leupeptin (Boehringer Mannheim), and 4 μg/ml pepstatin (Boehringer Mannheim). 200–500 μl supernatant of hybridomas which are positive in the immunofluorescence assay described in Example 1.3.1 are incubated with 100 μl of the SKBR3 extract (2.5–4.0 mg/ml). This amount of extract contains approximately 50–100 ng of c-erbB-2 protein. The hybridoma supernatants and SKBR3 extract are incubated overnight on ice, then 1 μl of the IgG fraction of sheep anti-mouse Ig (ICN Immunobiologicals) is added. The complexes are collected by the addition of Protein-A Sepharose™ (Pharmacia), washed with TNET (140 mM NaCl, 50 mM Tris-HCl, pH 7.5, 5 mM EDTA, 1% Triton X-100™) and water, boiled in sample buffer (80 mM Tris-HCl, pH 6.8, 0.2% SDS, 10% glycerol) and the supernatants loaded onto 8% SDS-PAGE. The proteins are electrophoresed and blotted onto PVDF membranes (Millipore) using a technique originally described by Towbin et al. (Proc. Natl. Acad. Sci. USA 76: 4350, 1979) with some modifications. The proteins are transferred using a semi-dry blotter (G. Frobel, Model 1004.01) following the instructions of the manufacturer. The membranes are blocked in PBS containing 0.5% gelatin (Merck) for 1 h at 37° C. The membranes are washed twice for 5 min at 37° C. in PTG (PBS containing 0.02% gelatin (Merck) and 0.25% Triton-X100™ (Fluka)). The c-erbB-2 protein is detected by incubating the membrane 45 min at 37° C. in PTG containing an antiserum which is raised against the carboxy terminal 13 amino acids of the c-erbB-2 protein (Gullick et al., Int. J. Cancer 40: 246, 1987, antiserum 21N). The membranes are washed 3 times for 5 min at 37° C. in PTG. The membrane-bound 21N antiserum is detected by incubating the membrane in PTG containing 0.1 μC/ml $^{125}$I-labeled protein-A (Amersham). The membranes are washed 4 times for 5 min at 37° C. in PTG and exposed to X-ray film. The hybridomas whose supernatants are able to specifically immunoprecipitate the c-erbB-2 protein are grown for single cell cloning and further characterization described below.

Example 2

Characterization of c-erbB-2 Specific MAbs 2.1 Hybridoma storage and processing: Hybridoma FRP5, FSP16, FWP51 and FSP77 secreting anti-c-erbB-2 MAb FRP5, FSP16, FWP51 and FSP77, respectively, can be grown in culture, frozen at −80° C. or in liquid nitrogen and recultivated. The cells are cloned by the method of limiting dilution and have been deposited with the European Collection of Animal Cell Lines in England. The hybridoma cell lines have the following access numbers: FRP5: 90112115, FSP16: 90112116, FSP77: 90112117, FWP51: 90112118. The cells are expanded by forming ascites in Balb/c mice primed with pristane. The antibodies are purified from the ascites by ammonium sulfate precipitation and ion exchange chromatography on DE 52 DEAE-cellulose columns (Whatman). Purified MAbs are stored in PBS at −80° C.

2.2 Isotyping of the MAbs: The isotype of the MAbs FRP5, FSP16, FWP51 and FSP77 is determined by ELISA analysis with rabbit antisera to mouse Ig classes and subclasses (Biorad Mouse Typer TMSub Isotyping Kit™) as per manufacturer's suggested procedure. MAbs FRP5, FWP51, and FSP77 are of the IgG1 isotype, while FSP16 is of the IgG2b isotype. The light chains of all the MAbs are of the kappa type.

2.3 Flow cytometry: A FACS analysis using the c-erbB-2 specific MAbs is carried out as follows: SKBR3 human breast tumor cells are trypsinized, washed in FACS medium (BSS containing 10 μM sodium azide, 4% FCS and 25 mM EDTA), and $1 \times 10^6$ cells are resuspended in 100 μl of FACS medium. Non-specific binding sites are blocked by incubating the cells 10 min at room temperature with 5 μl of goat serum. The SKBR3 cells are collected by centrifugation, resuspended in 50 μl of a 1:2 dilution of the supernatant made in FACS medium and incubated 45 min on ice. The cells are washed with 4 ml FACS medium, collected by centrifugation, resuspended in 50 μl of FACS medium containing a 1:20 dilution of anti-mouse Ig, fluorescein-linked whole antibody from sheep (Amersham), and incubated for 30 min on ice. 4 ml of FACS medium are added, the cells are collected by centrifugation, resuspended in 100 μl of FACS medium and analyzed without fixation for their fluorescence in a Becton-Dickinson FACScan™. As a control, SKBR3 cells are incubated with a non-reacting IgG1 MAb (1236S31-3). The FACS analysis shows that the SKBR3 cells treated with MAb FRP5, FSP16, FWP51, and FSP77 have a higher fluorescence than cells treated with the control MAb. These results show that the MAbs bind to the extracellular domain of the c-erbB-2 protein.

2.4 Binding domain of c-erbB-2 specific MAbs: MAbs FRP5 and FSP77 are covalently linked with $^{125}$I (as carrier free sodium $^{125}$iodide, Amersham) to a specific activity of 1 μC/μg using Iodogen (1,3,4,6-tetrachloro-3a,6a-diphenylglycouril, Sigma) according to a standard protocol (Antibodies: A Laboratory Manual, Cold Spring Harbor Laboratory, 1988, p. 330). Competition experiments are conducted by incubating SKBR3 cells (0.5–$1 \times 10^5$ cells per 15 mm well, Nunclon™ 4-well multidish) with 250 μl RIA buffer (120 mM NaCl, 50 mM HEPES, pH 7.8, 1 mM EDTA, 2% BSA) containing labeled FRP5 or FSP77 and varying amounts of unlabeled MAb FRP5, FSP16, FWP51 and FSP77 for 2 h at 4° C. The cells are washed 5 times with the RIA buffer, solubilized in 0.5 ml 1% Triton X-100™, 10% glycerol, 20 mM HEPES, pH 7.4, for 30 min at room temperature and the bound radioactivity is measured in a gamma counter. The results show that MAbs FRP5 and FSP16 compete with each other for binding to SKBR3 cells which suggests that these 2 MAbs bind to the same domain on the c-erbB-2 protein. MAbs FWP51 and FSP77 neither compete with each other nor with FRP5 or FSP16 for binding to the c-erbB-2 protein. In conclusion, the panel of 4 MAbs bind to 3 different domains of the extracellular portion of the c-erbB-2 membrane receptor tyrosine kinase.

Example 3

Isolation of RNA from the Hybridoma Cell Line FRP5

3.1 Growth of FRP5 cells: FRP5 hybridoma cells ($1\times10^8$) are grown in suspension culture at 37° C. in DMEM (Seromed) further containing 10% FCS (Amimed), 1 mM sodium pyruvate (Seromed), 2 mM glutamine (Seromed), 50 $\mu$M 2-mercaptoethanol and 100 $\mu$g/ml of gentamycin (Seromed) in a humidified atmosphere of air and 7.5% $CO_2$ in 175 cm tissue culture flasks (Falcon 3028). The cells are harvested by centrifugation, washed once in PBS, flash frozen in liquid nitrogen and kept frozen as a pellet at -80° C. in a clean, sterile plastic capped tube.

3.2 Extraction of total cellular RNA from FRP5 cells: Total RNA is extracted using the acid guanidinium thiocyanate-phenol-chloroform method described by Chomczynski & Sacchi (Anal. Biochem. 162: 156, 1987). Cell pellets of FRP5 cells ($1\times10^8$) are thawed directly in the tube in the presence of 10 ml of denaturing solution (4 M guanidinium thiocyanate (Fluka), 25 mM sodium citrate, pH 7.0, 0.5% N-lauroylsarcosine (Sigma), 0.1 M 2-mercaptoethanol). The solution is homogenized at room temperature. Sequentially, 1 ml of 2 M sodium acetate, pH 4, 10 ml of phenol (water saturated) and 2 ml of chloroform-isoamyl alcohol mixture (49:1) are added to the homogenate. The final suspension is shaken vigorously for 10 sec and cooled on ice for 15 min. The samples are centrifuged at 10,000×g for 20 min at 4° C. After centrifugation, RNA which is present in the aqueous phase is mixed with 10 ml of isopropanol and placed at -20° C. for 1 h. The RNA precipitate is collected by centrifugation, the pellet dissolved in 3 ml water and the RNA reprecipitated by addition of 1 volume of isopropanol at -20° C. After centrifugation and washing the pellet in ethanol, the final pellet of RNA is dissolved in water. The method yields approximately 300 $\mu$g of total cellular RNA. The final purified material is stored frozen at -20° C.

3.3 Isolation of poly(A) containing RNA: Poly(A) containing RNA is selected from total RNA by chromatography on oligo(dT)-cellulose (Boehringer Mannheim) as described originally by Edmonds et al. (Proc. Natl. Acad. Sci. USA 68: 1336, 1971) and modified by Maniatis et al. (Molecular Cloning: A Laboratory Manual, Cold Spring Harbor Laboratory, 1982, p. 197). The poly(A)-containing RNA is prepared as described in the published procedure with the exception that the RNA is eluted from the oligo(dT)-cellulose with water rather than SDS-containing buffer. The poly(A)-containing RNA is precipitated with ethanol and collected by centrifugation. The yield of poly(A)-containing RNA is approximately 30 $\mu$g from 300 $\mu$g of total cellular RNA. The final purified material is stored frozen at -20° C.

Example 4

Cloning of Functional Heavy and Light Chain Rearrangements from the FRP5 Hybridoma Cell Line Poly(A)-containing RNA isolated from FRP5 hybridoma cells as described in Example 3.3 provides the source for cDNA synthesis and subsequent amplification of V-region minigenes. Amplification products of the expected size are purified from agarose gels and cloned into appropriate vectors. Functional rearrangements are identified by sequencing.

4.1 Oligonucleotides:

MCK2 is designed to be complementary to a region in the murine immunoglobulin κ (kappa) constant minigene. This is described in SEQ ID NO:19.

5'-TCACTGGATGGTGGGAAGATGGA-3'

MCHC2 is designed to be complementary to a region in the murine immunoglobulin γ1 constant minigene. This is described in SEQ ID NO:20.

5'-AGATCCAGGGGCCAGTGGATAGA-3'

The oligonucleotides VH1FOR, VH1BACK, VK1FOR, and VK1BACK are designed by Orlandi et al. (Proc. Natl. Acad. Sci. USA 86: 3833, 1989) to match consensus sequences. These are described as SEQ ID NO:18, 21, 22 and 23.

VH1FOR: 5'-TGAGGAGACGGTGACCGTGGTCCCTTG-GCCCCAG-3'

VH1BACK: 5'-AGGT(C/G)(C/A)A(G/A)CTGCAG(G/C)AGTC(T/A)GG-3'

VK1FOR: 5'-GTTAGATCTCCAGCTTGGT(C/G)C(C/G)-3'

VK1BACK: 5'-GACATTCAGCTGACCCAGTCTCCA-3'

4.2 cDNA synthesis: 55 ng of poly(A)-containing RNA is dissolved in a buffer containing 50 mM Tris-HCl, pH 8.3,mM magnesium chloride, 10 mM DTT, 75 mM KCl, 400 $\mu$M dNTPs (N=G, A, T and C), 100 $\mu$g BSA (molecular biology grade, Boehringer Mannheim), 100 U RNAse inhibitor (Boehringer Mannheim), 25 pmol MCK2 and 25 pmol MCHC2. The RNA is denatured at 70° C. for 5 min and then chilled on ice for 2 min. After addition of 200 U of MMLV reverse transcriptase (Gibco, BRL) cDNA synthesis is achieved by incubation for 1 h at 37° C.

4.3 Polymerase chain reaction: One tenth of the cDNA reaction is used for DNA amplification in buffer containing 10 mM Tris-HCl, pH 8.3, 1.5 mM $MgCl_2$, 50 mM KCl, 10 mM β-mercaptoethanol, 200 $\mu$M dNTPs (N=G, A, T and C), 0.05% Tween-20™ (Merck), 0.05% NP-40™ (Merck), 10% DMSO (Merck), 25 pmol oligonucleotide 1 (see below), 25 pmol oligonucleotide 2 (see below) and 2.5 U Amplitaq™ DNA polymerase (Perkin Elmer Cetus). Taq polymerase is added after initial denaturation at 93° C. for 1 min and subsequent annealing at 37° C. In the first 4 cycles primer extension is performed at 71° C. for 0.2 min, denaturation at 93° C. for 0.01 min and annealing at 37° C. for 0.2 min. For the last 25 cycles the annealing temperature is raised to 62° C. Finally, amplification is completed by a 3 min primer extension step at 71 ° C.

| PCR Product | oligonucleotide 1 | oligonucleotide 2 |
| --- | --- | --- |
| HC | MCHC2 | VH1BACK |
| H | VH1FOR | VH1BACK |
| LC | MCK2 | VK1BACK |
| L | VK1FOR | VK1BACK |

4.4 Modification and purification: Amplified material is extracted with $CHCl_3$ and precipitated with ethanol in the presence of 200 mM LiCl. To facilitate cloning, blunt ends are created by a 3 min treatment with 1 U T4 DNA polymerase (Boehringer Mannheim) in 66 mM Tris-acetate, pH 7.9, 132 mM potassium acetate, 20 mM magnesium acetate, 1 mM DTT, 200 μg/ml BSA (molecular biology grade, Boehringer Mannheim), and 400 μM dNTPs (N=G, A, T and C). The polymerase is inactivated by heating for 15 min at 65° C. before phosphorylation of the DNA with 10 U T4 polynucleotide kinase (Pharmacia) at 37° C. for 1 h. For this purpose the buffer is adjusted to 50 mM EDTA and 1 mM ATP. The modified amplification products are separated on a 1.2% (w/v) agarose gel (ultra pure DNA grade agarose, Biorad) and DNA of the expected size is eluted by means of DEAE NA 45 membranes (Schleicher & Schuell).

4.5 Ligation: Bluescript™ KS+ (70 ng) linearized with XbaI, treated with Klenow DNA polymerase (Boehringer Mannheim) to give blunt ends and dephosphorylated with calf intestinal phosphatase, and 30 ng of purified amplification product are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of the ligation mixture is used to transform E. coli K803 to obtain ampicillin resistant colonies. These are screened for the desired ligation products using a NaOH based plasmid "miniprep" method (Maniatis et al., Molecular Cloning: A Laboratory Manual, Cold Spring Harbor Laboratory, 1982). The following plasmids are obtained:

| PCR product | Plasmid clones |
|---|---|
| HC | pMZ15/1 |
|  | pMZ15/2 |
| H | pMZ16/1 |
|  | pMZ16/2 |
| L | pMZ17/1 |
|  | pMZ17/2 |
| LC | pMZ18/1 |
|  | pMZ18/2 |

4.6 Sequencing: Sequencing is done using Sequenase™ kits (United States Biochemicals) with T3 and T7 oligonucleotide primers according to procedures provided by the manufacturer.

Plasmid pMZ17/1 contains a non-functional rearrangement. Plasmid pMZ17/2 contains an Ig-unrelated sequence. Plasmids pMZ18/1 (SEQ ID NO:2) and pMZ18/2 contain identical functional FRP5 kappa light chain variable domain inserts. Plasmids pMZ16/1 (SEQ ID NO:1) and pMZ16/2 contain identical functional FRP5 heavy chain variable domain inserts. Plasmids pMZ15/1 and pMZ15/2 also contain FRP5 heavy chain variable domain inserts together with some constant region DNA. Plasmids pMZ16/1 and pMZ18/1 are used as a source for further subcloning steps.

Example 5

Construction of the MAb FRP5 Single-Chain Fv Gene 5.1 Construction and sequence of a cloning linker for the heavy and light chain variable domain cDNAs: Using oligonucleotides, a linker sequence which allows the cloning of PCR amplified mouse heavy chain variable domain cDNA as a PstI/BstEII fragment and of PCR amplified mouse kappa light chain variable domain cDNA as a PvuII/BglII fragment is constructed. This creates an open reading frame in which heavy and light chain variable domains are connected by a sequence coding for the 15 amino acid stretch Gly-Gly-Gly-Gly-Ser-Gly-Gly-Gly-Gly-Ser-Gly-Gly-Gly-Gly-Ser of SEQ ID NO:17. This amino acid linker has been shown to allow correct folding of an antigen binding domain present in heavy and light chain variable domains in a single-chain Fv (Huston et al., Proc. Natl. Acad. Sci. USA 85: 5879, 1988).

For the construction of the cloning linker the 6 complementary oligonucleotides 1A, 1B, 2A, 2B, 3A, 3B are used. These are described as SEQ ID NO:24, 25, 26, 27, 28, and 29.

1A: 5'-CAAGCTTCTCAGGTACAACTGCAGGAGGT-CACCGTTTCCTCTGGCGG-3'
1B: 5'-GAAACGGTGACCTCCTGCAGTTGTACCTGA-GAAGCTTGCATG-3'
2A: 5'-TGGCGGTTCTGGTGGCGGTGGCTCCGGCG-GTGGCGGTTCTGAC-3'
2B: 5'-GCCACCGCCGGAGCCACCGCCACCAGAAC-CGCCACCGCCAGAG-3'
3A: 5'-ATCCAGCTGGAGATCTAGCTGATCAAAGCT-3'
3B: 5'-CTAGAGCTTTGATCAGCTAGATCTCCAGCT-GGATGTCAGAACC-3'

40 pM of oligonucleotides 1B, 2A, 2B, 3A are phosphorylated at the 5' end using T4 polynucleotide kinase (Boehringer Mannheim) in four separate reactions in a total volume of 20 μl following the method described by Maniatis et al. (Molecular Cloning: A Laboratory Manual, Cold Spring Harbor Laboratory, 1982). Oligonucleotides 1A and 3B are not phosphorylated in order to avoid self ligation of the linker in the final ligation reaction. After the kinase reaction, the enzyme is inactivated by incubation at 70° C. for 30 min. In three separate reactions, each containing 40 pM of two oligonucleotides in a total volume of 40 μl, non-phosphorylated 1A and phosphorylated 1B, phosphorylated 2A and phosphorylated 2B, and phosphorylated 3A and non-phosphorylated 3B are mixed. Hybridization of the oligonucleotides in the three reactions is carried out by heating to 95° C. for 5 min, incubation at 65° C. for 5 min and slowly cooling to room temperature. 10 μl from each of the three reactions are mixed, 4 μl of 10×ligation buffer (Boehringer) and 4 units of T4 DNA ligase (Boehringer) are added and the total volume is adjusted to 40 μl with sterile water. The annealed pairs of oligonucleotides are ligated into one linker sequence for 16 h at 14° C. The reaction mixture is extracted with an equal volume of phenol/chloroform (1:1) followed by re-extraction of the aqueous phase with an equal volume of chloroform/isoamylalcohol (24:1). The aqueous phase is collected, 0.1 volumes of 3 M sodium acetate pH 4.8 and 2 volumes of ethanol are added, and the DNA is precipitated at −70° C. for 4 h and collected by centrifugation. The resulting linker sequence has a SphI and a XbaI adaptor end. It is ligated to SphI and XbaI digested pUC19 in a reaction containing 100 ng of ligated linker and 200 ng of SphI/XbaI digested pUC19. After transformation into E. coli XL1 Blue™ (Stratagene), plasmid DNA from 4 independent colonies is isolated by the alkaline lysis mini-preparations method (Maniatis et al., Molecular Cloning: A Laboratory Manual, Cold Spring Harbor Laboratory, 1982). The DNA sequence of the linker cloned in pUC19 is determined by sequencing double stranded DNA in both directions with Sequenase II (United States Biochemicals) and pUC universal and reverse primers (Boehringer) following the manufacturer's protocol. Three out of the four recombinant pUC19 isolates sequenced contain the correct linker sequence. One of them is designated pWW19 and used in the further experiments. The sequence is shown in SEQ ID NO:3.

5.2 Preparation of a plasmid for the subcloning of variable domains: The Fv cloning linker sequence is derived as a 144 bp HindIII/SacI fragment from pWW19 and inserted into HindIII/SacI digested Bluescript™ KS+ (ex PvuII) (Stratagene) which contains no PvuII restriction sites. The resulting plasmid, pWW15, allows cloning of heavy and light chain variable domains as PstI/BstEII and PvuII/BglII fragments, respectively.

5.2.1 Subcloning of the FRP5 heavy chain variable domain: Plasmid pMZ16/1 is digested with PstI and BstEII and the 338 bp heavy chain variable domain fragment of FRP5 is isolated. It is cloned into PstI/BstEII digested pWW19 yielding the plasmid pWW31.

5.2.2 Mutation of the FRP5 light chain variable domain and assembly of the Fv fusion gene: To facilitate subcloning of the FRP5 light chain variable domain into the Fv cloning linker, a PvuII restriction site and a BglII restriction site are introduced at the 5' and 3' ends, respectively, of the coding region. The FRP5 light chain variable domain coding region is isolated as a SacI/BamHI fragment from pMZ18/1. SacI and BamHI are restriction sites of the Bluescript™ polylinker present in pMZ18/1. The fragment contains the complete light chain variable domain fragment of 392 bp amplified by PCR using the oligonucleotide MCK2 (see above). This fragment is mutated and amplified by PCR using the oligonucleotides, described as SEQ ID NO:30 and 31.

$V_L5'$: 5'-GACATTCAGCTGACCCAG-3' and
$V_L3'$: 5'-GCCCGTTAGATCTCCAATTTTGTCCCCGAG-3' for the introduction of a PvuII restriction site at the 5' end ($V_L5'$) and a BglII restriction site at the 3' end ($V_L3'$) of the kappa light chain variable domain DNA. 20 ng of the FRP5 variable light chain SacI/BamHI fragment are used as a template in a 100 μl reaction following the PCR conditions described in Example 4.3. The amplified and mutated fragment is isolated after PvuII/BglII digestion as a 309 bp fragment from a 1.5% agarose gel and cloned into PvuII/BglII digested pWW15 generating plasmid pWW41. The FRP5 kappa light chain variable domain is isolated as a BstEII/XbaI fragment from pWW41 and inserted into BstEII/XbaI digested pWW31. Thus the FRP5 heavy chain variable domain in pWW31 and the FRP5 kappa light chain variable domain are fused to one open reading frame. Double stranded DNA of three independent clones is sequenced with Sequenase II™ kit (United Biochemicals) in both orientations using pUC universal and reverse primers (Boehringer) following the manufacturer's protocol. One of the plasmids carrying the FRP5 heavy chain variable domain fused to the mutated FRP5 light chain variable domain is selected and designated pWW52. The sequence of the HindIII/XbaI insert in plasmid pWW52 is shown in SEQ ID NO:4 and 5.

Example 6

Construction of a Single-Chain Fv-Phosphatase Fusion Gene Expression Plasmid

The MAb FRP5 single-chain Fv gene is fused to the bacterial alkaline phosphatase. This chimeric gene encodes a bifunctional molecule which retains binding activity to the c-erbB-2 protein and has enzymatic activity.

6.1 Mutation of the single-chain Fv(FRP5) gene: To allow gene fusion between the single-chain Fv(FRP5) encoding gene from pWW52 and the alkaline phosphatase gene phoA the stop codon at sequence position 729 to 731 in pWW52 (see Example 5.2.3) is deleted as follows: Plasmid DNA of pWW52 is digested with BstEII and BglII and the linker sequence and FRP5 light chain variable domain encoding fragment is isolated. In another digestion, pWW52 is cleaved with BstEII and BclI. Thus, the large fragment containing vector sequences and the FRP5 heavy chain variable domain encoding sequence is isolated. The BstEII/BglII $V_L$ fragment is now inserted into BstEII/BclI cleaved pWW52 containing $V_H$. In the resulting plasmid, pWW53, the BglII/BclI junction is determined by sequencing double stranded DNA as described above.

Sequence of the BglII/BclI junction in pWW53 (position numbers correspond to position numbers of the HindIII/XbaI insert in plasmid pWW52, SEQ ID NO:4 and 5):

```
           BglII/BclI
ACA AAA TTG GAG ATC AAA GCT CTA GA
        714-728 | 738-748,
    described as SEQ ID NO:32.
```

6.2 Mutation of the E.coli alkaline phosphatase gene phoA: For the construction of the Fv(FRP5)-phoA fusion gene the E. coli alkaline phosphatase gene phoA is mutated to generate a XbaI cleavage site in the coding region of phoA near the N terminus of the mature protein and a SacI cleavage site in the 3' untranslated region of phoA. This step facilitates the cloning of the mutated fragment. A pBR322 derivative carrying the recombinant transposon TnPhoA (Manoil & Beckwith, Proc. Natl. Acad. Sci. USA 82: 8129, 1985) is linearized by BglII cleavage. 20 ng of the linearized template DNA is used for a 100 μl PCR reaction carried out as described previously using oligonucleotides PhoA5' and PhoA3' as primers 1 and 2, described as SEQ ID NO:33 and 34.

PhoA5': 5'-CCCTCTAGAGCCTGTTCTGGAAAAC-3'
PhoA3': 5'-CCCGAGCTCTGCCATTAAG-3'

Following XbaI/SacI digestion of the PCR products, a 1419 bp fragment is isolated from a 1.5% agarose gel and inserted into XbaI/SacI digested plasmid pUC19. Ligation is carried out as described above. Ligated DNA is transformed into E. coli XL1 Blue™ (Stratagene). Thus, the open reading frame of the mutated phoA gene is fused in frame to the lacZ open reading frame of pUC19. To show that the mutated phoA gene expresses functional alkaline phosphatase, recombinant clones are plated onto LB agar plates containing 100 μg/ml ampicillin, 0.5 mM IPTG (Sigma), and 40 μg/ml XP (Boehringer). Following induction of the lac promoter of pUC19, a lacZ-phoA fusion protein is expressed. The phosphatase activity of this fusion protein converts the indicator XP to a blue dye. One of the blue colonies is isolated and the presence of the introduced restriction sites is confirmed by digestion of miniprep DNA with XbaI and SacI. Partial 5' and 3' DNA sequences of the mutated phoA gene are obtained by sequencing double stranded DNA as described above. The DNA sequences are included in the assembly of the final Fv(FRP5)-phoA fusion gene sequence shown in SEQ ID NO:6 and 7. The isolated plasmid is designated pWW61 and used for further subcloning steps.

6.3 Construction of a FRP5 Fv-phoA expression plasmid: From plasmid pWW19 (see Example 5.1.2) the cloning linker sequence is isolated as a HindIII/EcoRI fragment and inserted into HindIII/EcoRI digested plasmid pINIII-ompA-Hind (Rentier-Delrue et al., Nucl. Acids Res. 16: 8726, 1988) leading to plasmid pWW16.

From pWW61 (see Example 6.2) the mutated phoA gene is isolated as a XbaI/SacI fragment and inserted into XbaI/SacI digested pWW53. The resulting plasmid, pWW615, carries the Fv(FRP5) gene fused in frame to the mutated alkaline phosphatase gene. The Fv(FRP5)-phoA gene is isolated as a HindIII/SacI fragment from pWW615 and inserted into HindIII/SacI digested plasmid pWW16. This leads to the production of the Fv(FRP5)-phoA expression plasmid pWW616 (see below). All ligations are carried out as described above. Recombinant plasmids are transformed into E. coli XL1 Blue™ (Stratagene). The constructs are confirmed by restriction enzyme analysis of plasmid DNA isolated by an alkaline mini preparation method (Maniatis et al., Molecular Cloning: A Laboratory Manual, Cold Spring Harbor Laboratory, 1982).

In this construct the Fv single-chain antibody of FRP5, genetically fused to the alkaline phosphatase phoA, can be expressed in E. coli following induction with IPTG. The recombinant protein carries the E. coli outer membrane protein A (ompA) signal sequence at the N terminus (encoded by the pINIII-ompA-Hind vector) to facilitate secretion of the protein into the periplasmic space of E. coli expressor cells.

The sequence of the Fv(FRP5)-phoA fusion gene in expression plasmid pWW616 is shown in SEQ ID NO:6 and 7. Part of the phoA sequence is assembled from Chang et al., Gene 44: 121, 1986.

Example 7

Expression of Fv(FRP5)-phoA in E. coli

Plasmid pWW616 is transformed into the phoA negative E. coli strain CC118 (Manoil & Beckwith, Proc. Natl. Acad. Sci. USA 82: 8129, 1985). A recombinant single colony is grown overnight in 50 ml LB medium containing 70 μg/ml ampicillin. The overnight culture is diluted 1:10 in 500 ml fresh LB medium containing 70 μg/ml ampicillin and grown at 37° C. to an $OD_{550}$ of 0.1. IPTG is added to a final concentration of 2 mM and expression is induced for 1.5 h at 37° C. The cells are harvested at 4° C. by centrifugation at 4000 rpm for 25 min in a Beckman GPKR centrifuge. The supernatant of CC118/pWW616 is set aside on ice for preparation of Fv(FRP5)-phoA, see Example 7.2.

7.1 Isolation of Fv(FRP5)-phoA from the periplasmic proteins of CC118/pWW616: The bacterial pellet is suspended in 10 ml TES buffer (0.2 M Tris-HCl, pH 8.0, 0.5 mM EDTA, 0.5 M sucrose) and kept on ice for 10 min. After centrifugation at 4° C. for 10 min at 5000 rpm in a Heraeus minifuge, the supernatant is discarded and the washed pellet is suspended in 15 ml ice-cold TES, diluted (1:4) with water. The cells are kept on ice for 30 min and recentrifuged as above. The supernatant containing periplasmic proteins is recentrifuged at 45,000×g for 15 min in a Beckman TL100 ultracentrifuge. The periplasmic extract is concentrated in an Amersham ultrafiltration unit through a YM10 membrane to a final volume of 2 ml. Following fivefold dilutions with PBS and reconcentration through the YM10 membrane five times, the 1:4 diluted TES buffer of the periplasmic extract is exchanged with PBS. $NaN_3$ and protease inhibitors are added to the periplasmic proteins (2 ml in PBS) to the final concentration of 0.02% $NaN_3$, 0.1 mM PMSF, 2 μg/ml aprotinin, 1 μg/ml leupeptin, and 1 μg/ml pepstatin. The periplasmic extract is stored at 4° C.

7.2 Isolation of Fv(FRP5)-phoA from the concentrated supernatant of E. coli CC118/pWW616 cultures: The supernatant (500 ml) of the induced E. coli culture CC118/pWW616 is filtered through a 0.45 μm membrane. The filtrate is concentrated in an Amicon ultrafiltration unit through a YM10 membrane to a final volume of 10 ml in PBS as described above. $NaN_3$ and protease inhibitors are added to the concentrated supernatant to the final concentrations indicated above. The concentration of Fv(FRP5)-phoA in the extracts is determined by densitometry in comparison to BSA standards of coomassie stained 9% SDS-PAGE gels.

Example 8

Activity of Fv(FRP5)-phoA 8.1 Detection of c-erbB-2 in SKBR3 breast tumor cells by immunostaining using Fv(FRP5)-phoA: The Fv domain of Fv(FRP5)-phoA enables the molecule to bind to the extracellular domain of the c-erbB-2 protein. Bound Fv(FRP5)-phoA can be visualized by staining procedures using color substrates for the detection of alkaline phosphatase activity.

8.1.1 Fixation of cells: SKBR3 human breast tumor cells carrying about $1 \times 10^6$ c-erbB-2 receptors per cell are grown on fibronectin coated glass cover slips. The cells are washed twice with PBS and then fixed with PBS/3.7% formaldehyde at room temperature for 30 min. The fixed cells are washed three times with PBS at room temperature. Unspecific binding, sites are blocked by incubating the cells for 1 h with PBS/3% BSA at 37° C. in a humid incubator. The cells are then washed twice with PBS.

8.1.2 Pretreatment of Fv(FRP5)-phoA: Alkaline phosphatase phoA from E. coli must be dimerized to be enzymatically active. In the periplasm of E. coli natural phoA is dimerized, i.e. two molecules of phoA are held together by two $Zn^{2+}$ ions. The Fv(FRP5)-phoA is also produced as a dimer in E. coli. To increase binding of Fv(FRP5)-phoA to the antigen, the dimers are monomerized by adding EGTA to the solution. This step removes $Zn^{2+}$ from the solution. Monomerized phosphatase can be re-dimerized by the addition of $Zn^{2+}$. EGTA is added to a final concentration of 5 mM to 200 μl of 40×concentrated supernatant or periplasmic proteins from CC118/pWW616 (see above). The solution is incubated at 37° C. for 1 h just before use in the immunoassay.

8.1.3 Staining of cells: After blocking with PBS/3% BSA (see above) fixed cells are incubated for 1 h with pretreated Fv(FRP5)-phoA at a concentration of 1 μg/ml at 37° C. in a humidified incubator. The cells are washed three times with PBS at room temperature. The staining solution consists of 300 μl naphtol AS-MX™ phosphate (Sigma, 13 mg/ml in dimethyl formamide), 8 mg of levamisole (Sigma), and 10 mg of Fast Red TR™ salt (Sigma) added to 9.7 ml of 100 mM Tris-HCl, pH 8.2, 1 mM $ZnCl_2$. This mixture is prepared and filtered through a 0.45 μm filter immediately before use. $ZnCl_2$ is added to the staining solution to allow re-dimerization of bound Fv(FRP5)-phoA and thereby activating the alkaline phosphatase. Cells are incubated in the Fast Red™ staining solution for 15 min at room temperature. The phosphatase activity is blocked after staining by washing the cells twice with PBS and once with 1 M $KH_2PO_4$. Glass cover slips are mounted with gel mount (Biomeda). The cells are examined under a fluorescence microscope using green light for excitation. Stained SKBR3 cells show intense red cell surface fluorescence.

8.2 Detection of c-erbB-2 protein over-expression in immunoblots using Fv(FRP5)-phoA: Proteins from total cell lysates of SKBR3 cells over-expressing c-erbB-2 protein are separated by SDS-PAGE and blotted onto PVDF membrane (Millipore). For preparation of extracts and immunoblotting technique see Example 1.3.2. Free binding sites of the membrane are blocked by incubation for 1 h at room temperature in a solution containing 10 mM Tris-HCl, pH 7.5, 0.9% NaCl, 0.05% Tween 20™ (BioRad), and 3% BSA. Pretreated Fv(FRP5)-phoA (see Example 7.2.) is diluted in blocking solution to a final concentration of 0.1 μg/ml. The membrane is incubated in the Fv(FRP5)-phoA solution for 1 h at room temperature and then washed three times for 5 min at room temperature in 10 mM Tris-HCl, pH 7.5, 0.9% NaCl, 0.05% Tween 20™ and once in 10 mM Tris-HCl, pH 7.5, 0.9% NaCl. For detection of bound Fv(FRP5)-phoA the membrane is incubated for 20 min at 37° C. in the Fast Red™ substrate solution described in Example 7.3 without levamisole. The reaction is stopped by washing the membrane twice in water. Fv(FRP5)-phoA specifically detects the 185 kD c-erbB-2 protein.

Example 9

Expression and Isolation of Fv(FRP5)-phoA from E. coli 9.1 Preparation of periplasmic extract: Plasmid pWW616 is transformed into the phoA negative E. coli strain CC118 according to standard procedures (Maniatis et al., Molecular Cloning: A Laboratory Manual, Cold Spring Harbor Laboratory, 1982). A single colony is picked and grown overnight in LB medium containing 70 μg/ml ampicillin. The overnight culture is diluted 1:10 in fresh LB medium containing ampicillin and grown at 37° C. to an $OD_{550}$ of 0.1. At this point expression of the Fv(FRP5)-phoA gene is induced by the addition of IPTG to a final concentration of 2 mM, and the cells are grown for an additional 1.5 to 2 h. The cells are harvested by centrifugation and treated with a mild osmotic shock which releases the periplasmatic proteins into the supernatant. The proteins are concentrated in an Amersham ultrafiltration unit through a YM10 membrane.

9.2 Preparation of an antigen affinity column: The c-erbB-2 protein is isolated from insect cells infected with a baculovirus vector expressing the c-erbB-2 extracellular domain by standard methods (V. A. Luckow & M. D. Summers, Biotechnology 6: 47–55, 1988). MAb FSP77 is coupled to CNBR-activated Sepharose 4B™ (Pharmacia) following the instructions of the manufacturer. The insect cell lysates are incubated with the coupled MAb FSP77 in a buffer containing 50 mM Tris-HCl, pH 7.5, 5 mM EGTA, 0.5% Triton X-100™, 150 mM NaCl for 2 h at 4° C. on a shaking platform. The beads are packed into a column and washed with pre-elution buffer consisting of 10 mM phosphate, pH 6.8, and 100 mM NaCl to remove non-specifically bound proteins. The c-erbB-2 protein is recovered from the column by treatment with a low pH elution buffer containing 100 mM glycine, pH 3.0, and 100 mM NaCl. The fractions from the column are collected into phosphate buffer, pH 8.0, in order to raise the pH. The c-erbB-2 extracellular domain is detected by running a part of each fraction on 8% SDS-PAGE gel, blotting onto PVDF membrane (Millipore) and treating the filter with MAb FSP77 followed by sheep anti-mouse IgG. Bound IgG is detected by $^{125}$I-Protein-A treatment. The fractions containing the extracellular domain are pooled and the protein is coupled to CNBR-activated Sepharose 4B™ (Pharmacia) following the instructions of the manufacturer.

9.3 Isolation of Fv(FRP5)-phoA by affinity chromatography: The sepharose coupled to c-erbB-2 protein (Examle 9.2) is incubated for 2–4 h at 4° C. on a rocking platform with the periplasmic extract isolated as described in Example 9.1. The beads are packed into a column and washed with pre-elution buffer as in Example 9.2. The Fv(FRP5)-phoA protein is recovered by elution with the low pH elution buffer of Example 9.2. The fractions are monitored for the presence of the Fv(FRP5)-phoA by testing for phoA enzymatic activity using a standard protocol.

Example 10

Immunoassay for c-erbB-2 Protein in Tumors 10.1 Preparation of tumor sections: To determine the level of c-erbB-2 protein in tumors, tumor tissue is pretreated to give either frozen tumor sections or paraffin-embedded tumor sections. Tumor pieces are quick frozen, then cut with a cryostat, collected onto 1% gelatin-coated glass slides, and fixed with 4% paraformaldehyde. Following several washes with PBS, the tumor tissue sections are ready for staining. Alternatively, tumor pieces are placed in 4% paraformaldehyde for fixation, embedded in paraffin, then sections cut and collected onto polylysine-coated glass cover slips. To prepare the sections for staining, they are heated overnight at 56° C., dewaxed in xylene, stepwise rehydrated by washing in 95%, 70% and 35% ethanol and water, and washed in PBS.

10.2 Pretreatment of Fv(FRP5)-phoA: Since the dimer of the Fv(FRP5)-phoA as obtained from the E. coli periplasm does not bind optimally to the c-erbB-2 antigen, it is first monomerized. This is accomplished by treating the solution of Fv(FRP5)-phoA for 1 h at 37° C. with EGTA at a final concentration of 5 mM. This treatment chelates the $Zn^{2+}$ ions which are important for maintaining the dimeric structure of Fv(FRP5)-phoA.

10.3 Staining of the tumor sections: Non-specific staining of the tumor sections prepared according to Example 10.1 is blocked by incubating the sections in PBS containing 3% BSA. The blocked sections are incubated for 1–2 h with pretreated Fv(FRP5)-phoA (Example 10.2) at a concentration of 1 μg/ml in a humidified chamber at room temperature. The sections are washed three times with PBS at room temperature. The bound Fv(FRP5)-phoA protein is detected using Fast Red™ as a substrate for the alkaline phosphatase. The staining solution consists of 300 μl naphthol AS-MX phosphate (Sigma, 13 mg/ml in dimethylformamide), 8 mg of levamisole (an inhibitor of endogenous alkaline phosphatase, Sigma), and 10 mg of Fast Red TR™ salt (Sigma) added to 9.7 ml of 100 mM Tris-HCl, pH 8.2, and 1 mM $ZnCl_2$. This mixture is prepared and filtered through a 0.45 μm filter immediately before use. $ZnCl_2$ is added to the staining solution to allow re-dimerization of the bound Fv(FRP5)-phoA protein and activation of the alkaline phosphatase. The tumor sections treated with Fv(FRP5)-phoA are incubated in the Fast Red™ staining solution for 15 min at room temperature. After staining the phosphatase activity is blocked by washing the cells twice with PBS and once with 1 M $KH_2PO_4$. The glass cover slips are mounted with gel mount. The cells are examined under a fluorescence microscope using green light for excitation. Positively stained cells show an intense red cell surface fluorescence.

Alternatively, the tumor sections treated with the Fv(FRP5)-phoA protein may be stained with naphthol AS-BI phosphate (Sigma) and New Fuchsin™ (Sigma), or with 5-bromo-4-chloro-3-indolyl phosphate (BCIP, Sigma) and Nitro Blue Tetrazolium™ (Sigma). The stained sections can then be viewd with a regular light microscope.

Example 11

Cloning of Functional Heavy and Light Chain Rearrangements from the FWP51 Hybridoma Cell Line Poly(A)-containing RNA isolated from FWP51 hybridoma cells as described in Example 3.3 provides the source for cDNA synthesis and subsequent amplification of V-region minigenes. cDNA synthesis and amplification of FWP51 heavy and light chain variable domain cDNA by polymerase chain reaction is carried out as described in Example 4. Amplification products of the expected size are purified from agarose gels and cloned into appropriate vectors. Functional rearrangements are identified by sequencing.

11.1 Subcloning of FWP51 heavy and light chain variable domain cDNA: Material amplified according to Example 4.3 is extracted with CHCl$_3$ and precipitated in the presence of 200 mM LiCl. To facilitate cloning, the FWP51 heavy chain variable domain cDNA is cleaved with restriction enzymes PstI and BstEII, the fragment purified by agarose gel electrophoresis, and ligated to PstI and BstEII digested pWW15 DNA. The FWP51 light chain variable domain cDNA is cleaved with restriction enzymes PvuII and BglII, the fragment is purified by agarose gel electrophoresis, and ligated to PvuII and BglII digested pWW15 DNA (cf. Example 5). Ligation, transformation, and screening for the desired ligation products are carried out as described in Example 4.5. The following plasmids are obtained:

| PCR product | Plasmid clones |
| --- | --- |
| H | pWW15-VH51-1 |
|   | pWW15-VH51-2 |
|   | pWW15-VH51-3 |
| L | pWW15-VL51-1 |
|   | pWW15-VL51-2 |
|   | pWW15-VL51-3 |

11.2 Sequencing: Sequencing is done as described in Example 4.6.

Plasmids pWW15-VH51-1 (SEQ ID NO:8), pWW15-VH51-2, pWW15-VH51-3 contain identical functional FWP51 heavy chain variable domain inserts. Plasmids pWW15-VL51-1 (SEQ ID NO:9), pWW15-VL51-2, pWW15-VL51-3 contain identical functional FWP51 kappa light chain variable domain inserts. Plasmids pWW15-VH51-1 and pWW15-VL51-1 are used as a source for further subcloning steps.

Example 12

Construction of the MAb FWP51 Single Chain Gene 12.1 Assembly of the Fv fusion gene: Plasmid pWW15-VH51-1 is digested with PstI and BstEII and the 342 bp heavy chain variable domain fragment of FWP51 is isolated. It is cloned into PstI/BstEII digested pWW15-VL-51-1 yielding the plasmid pWW15-Fv51 (SEQ ID NO:10 and 11).

12.2 Mutation of the single-chain Fv(FWP51) gene: To allow gene fusion between the single-chain Fv(FWP51) encoding gene from pWW15-Fv51 and effector genes the stop codon at sequence position 729 to 731 in pWWFv15-51 (SEQ ID NO:10 and 11) is deleted as follows (see also Example 6.1): plasmid DNA of pWW15-Fv51 is digested with BstEII and BglII and the linker sequence and FWP51 light chain variable domain encoding fragment is isolated. In another digestion, pWW15-Fv51 is cleaved with BstEII and BclI. Thus, the large fragment containing vector sequences and the FWP51 heavy chain variable domain encoding sequence is isolated. The BstEII/BglII V$_L$ fragment is now inserted into BstEII/BclI cleaved pWW15-Fv51 containing V$_H$. The resulting plasmid pWW15-Fv51-ORF is used as a source for the construction of Fv(FWP51)-effector fusion genes.

Example 13

Construction of Single-Chain Fv-exotoxin A Fusion Gene Expression Plasmids

The MAb FRP5 and MAb FWP51 single-chain Fv genes are fused to a truncated bacterial toxin, exotoxin A (ETA) from Pseudomonas aeruginosa. These chimeric genes encode recombinant immunotoxins which selectively inhibit protein synthesis in c-erbB-2 expressing cells.

13.1 Mutation of the Exotoxin A gene of Pseudomonas aeruginosa PAK: For the construction of Fv-exotoxin A (Fv-ETA) fusion genes the ETA gene from Pseudomonas aeruginosa PAK is mutated to delete the original cell binding domain I at the N-terminus of the toxin and to generate a XbaI cleavage site at the former domain I/domain II boundary of the ETA coding region. Plasmid pMS150A (Lory et al., J. Bacteriol. 170: 714, 1988) is linearized by EcoRI cleavage. 20 ng of the linearized template DNA is used for a 100 µl PCR reaction carried out as described previously using the following oligonucleotides as primers 1 and 2.

1: 5'-CACGGAAGCTTAAGGAGATCTGCATGCTTCTAGAGGGCGGCA-GCCTGGCCGCGCTG-3'

2: 5'-GCGGATCGCTTCGCCCAGGT-3'

Following HindIII/SalI digestion of the PCR products, a 201 bp fragment is isolated from a 1.5% agarose gel and inserted into HindIII/SalI digested plasmid pUC18. Ligation is carried out as described above. Ligated DNA is transformed into E.coli XL1 Blue™ (Stratagene). Two recombinant plasmids are isolated and the insert DNA is sequenced as described above using pUC universal and reverse primers (Boehringer). One plasmid containing the expected product is designated pWW22 (SEQ ID NO:12) and used as a source for further subcloning steps. Plasmid pWW22 is cleaved with HindIII and SalI, the mutated ETA gene fragment is isolated, and inserted into the large fragment of HindIII/SalI digested plasmid pMS150A containing pUC9 vector sequences and part of the ETA gene coding for the C-terminal half of the toxin. Thereby in the resulting plasmid pWW20 a truncated ETA gene coding for domains II and III of the toxin is created.

13.2 Assembly of single-chain Fv-ETA fusion genes: HindIII/XbaI single-chain Fv gene fragments suitable for the construction of Fv-ETA fusion genes are isolated from plasmid pWW53 (single-chain Fv FRP5), and plasmid pWW15-Fv51-ORF (single-chain Fv FWP51) and inserted into HindIII/XbaI digested pWW20. Ligation and transformation into E.coli XL1 Blue™ (Stratagene) are carried out as described above. The resulting plasmids pWW20-Fv5 (Fv(FRP5)-ETA) and pWW20-Fv51 (Fv(FWP51)-ETA) are used as a source for further subcloning, steps.

13.3 Construction of single-chain Fv-exotoxin A fusion gene expression plasmids: For the expression of single-chain Fv-exotoxin A fusion genes in E.coli the expression plasmid pFLAG-1 (IBI Biochemicals) is used. The fusion-genes are fused in frame to the outer membrane protein A (ompA) signal sequence encoded by pFLAG-1. Plasmid DNA from pWW20-Fv5 and pWW20-Fv51 is digested with HindIII and blunt ends are created by Klenow fill-in as described in Example 4.5. Blunt ended DNA is digested with EcoRI and single-chain Fv-ETA gene fragments are isolated (Fv (FRP5)-ETA: 1916 bp, Fv(FWP51)-ETA: 1916 bp). pFLAG-1 plasmid DNA is digested with HindIII, blunt ends are created as described above, the resulting DNA fragment is isolated, and digested with EcoRI. Blunt-end/EcoRI Fv-ETA fusion gene fragments are inserted into the modified pFLAG-1 plasmid DNA. Thereby Fv-ETA fragments are fused in frame to the ompA signal sequence of pFLAG-1 creating plasmids pWW215-5 for the expression of Fv(FRP5)-ETA (SEQ ID NO: 13 and 14) and pWW215-51 for the expression of Fv(FWP51)-ETA (SEQ ID NO:15 and 16).

Example 14

Expression and Isolation of Fv(FRP5)-ETA and Fv (FWP51)-ETA from E. coli 14.1 Preparation of total lysates: Plasmids pWW215-5 and pWW215-51 are transformed into the *E.coli* strain CC118 according to standard procedures (see Example 9.1). Single colonies are picked and grown overnight in LB medium containing 100 μg/ml ampicillin and 0.4% glucose. The overnight cultures are diluted 1:30 in fresh LB medium containing ampicillin and glucose and grown at 37° C. to an $OD_{550}$ of 0.5. At this point expression of the Fv(FRP5)-ETA and Fv(FWP51)-ETA genes is induced by the addition of IPTG to a final concentration of 0.5 mM, and the cells are grown for an additional 30 min. The cells are harvested by centrifugation and lysed by sonication in PBS/1 mM $CaCl_2$. The lysates are cleared by ultracentrifugation at 25 000 g for 45 min at 4° C. The supernatants are collected.

14.2 Isolation of Fv(FRP5)-ETA and Fv(FWP51)-ETA by affinity chromatography: Cleared *E.coli* lysates containing the 66.4 kDa Fv(FRP5)-ETA or the 66.3 kDa Fv(FWP51)-ETA protein are passed through a M1 monoclonal antibody affinity column (IBI Biochemicals). The column is washed three times with PBS/1 mM $CaCl_2$. Bound Fv(FRP5)-ETA or Fv(FWP51)-ETA proteins are eluted with PBS/2 mM EDTA. The fractions are monitored for the presence of Fv-ETA proteins by SDS-PAGE and immunoblotting (see Example 1.3.2) using an anti-exotoxin A antiserum developed in rabbit.

Example 15

Selective Inhibition of Protein Synthesis in c-erbB-2 Expressing Cells with Fv(FRP5)-ETA and Fv (FWP5 1)-ETA In vitro the recombinant immunotoxins Fv(FRP5)-ETA and Fv(FWP51)-ETA selectively inhibit protein synthesis and growth of cells expressing high levels of the human c-erbB-2 protein. The immunotoxins do not affect cells expressing no, or low levels of human c-erbB-2 protein.

15.1 Immunotoxin treatment of cell lines: Human breast and ovarian tumor cell lines SK-BR3, MDAMB-231, MDA-MB-453, HTB77, the mouse mammary epithelial cell line HC11, and HC11 cells transfected with the human c-erbB-2 cDNA are plated on 48 well tissue culture plates (Costar) at a density of $105^5$ cells/well. After 4 h the medium is removed and replaced by normal growth medium containing Fv(FRP5)-ETA or Fv(FWP51)-ETA at various concentrations ranging from 1 to 1000 ng/ml. The cells are incubated with toxin fusion proteins for 16 h.

15.2 $^3$H-leucine labeling of cells: The immunotoxin-treated cells are washed twice and incubated in normal growth medium containing 4 μCi $^3$H-leucin/ml for 4 h. The labeled cells are washed twice and $^3$H-leucine labeled total proteins are harvested by TCA precipitation onto Whatman GFC filters. The rate of protein synthesis in immunotoxin-treated cells is determined in comparison to untreated control cells.

Example 16

Fv(FRP5)-ETA and MAbs FWP51 and FSP77 Inhibit the Growth of c-erbB-2 Expressing Cells in Nude Mice The administration of Fv(FRP5)-ETA and the MAbs FWP51 and FSP77 to animals injected with c-erbB-2 expressing cells inhibits the tumor growth of these cells.

16.1 Nude mouse tumor model.: The NIH/3T3 mouse fibroblast cell line is transfected according to conventional, previously described methods (Graham & van der Eb, Virology 52: 456, 1973) with a plasmid expressing the point mutated, activated human c-erbB-2 protein (Masuko et al., Jpn. Cancer Res. 80: 10, 1989) and with the plasmid pSV2neo (Southern & Berg, J. Mol. Appl. Genet. 1:327, 1982) which encodes the gene for resistance to the drug G418. Transfected cells are selected 2 weeks in medium containing 500 ug/ml G418 (Geneticin, Gibco-BRL). Individual clones are selected and analyzed for the expression of the human c-erbB-2 protein using conventional protein blotting techniques (Towbin et al., Proc. Natl. Acad. Sci. USA 76: 4350, 1979). A clone expressing moderate levels of the point mutated, activated human c-erbB-2 protein (clone 3.7) is selected, and tested for growth in nude mice. 2–5×106 clone 3.7 cells (per animal) suspended in 0.2 ml PBS are subcutaneously injected into the flank of female Balb/c nude mice. The 3.7 cells injected at a dose of 2×106 cells rapidly form tumors in nude mice (control animals, cf. Example 16.2)

16.2 Immunotoxin treatment of animals: 2×106 clone 3.7 cells are injected subcutaneously into nude mice. The animals are treated continuously for a total of 7 days with the Fv(FRP5)-ETA. 200 μl of Fv(FRP5)-ETA (concentration 35 μg/ml in PBS) is placed in an osmotic pump (Alzet mini osmotic pump, Model 2001, Alza, Palo Alto, Calif., #94303-0802) which is implanted subcutaneously into the animals at the same time as the clone 3.7 cells are injected. The pump continuously releases Fv(FRP5)-ETA and delivers 1 μg/day for 7 days to each animal. In comparison with the control animals (cf. Example 16.1), the administration of Fv(FRP5)-ETA delays the onset of tumor formation.

16.3 MAb treatment of animals: 5×106 clone 3.7 cells are injected subcutaneously into nude mice. Starting on the same day as injection of clone 3.7 cells, the animals are treated daily, for a total of 10 days, with either MAb FWP51 or MAb FSP77 (MAb dose is 50 ug/200 ul BSS/day). The MAb is injected intraveneously in the tail vein of the mouse. Both antibodies delay the onset of tumor growth. Compared therewith, a synergistic effect in inhibiting tumor growth is observed on simultaneous administration of both antibodies MAb FWP51 and MAb FSP77.

DESCRIPTION OF THE SEQUENCES

SEQ ID NO:1 is the nucleotide sequence of pM716/1, which encodes the heavy chain variable domain of monoclonal antibody FRP5.

SEQ ID NO:2 is the nucleotide sequence of pM718/1, which encodes the kappa light chain variable domain of monoclonal antibody FRP5.

SEQ ID NO:3 is the nucleotide sequence of pWW19, which is used to link the heavy and light chain variable domains.

SEQ ID NO:4 is the nucleotide sequence of pWW52, which encodes the Fv heavy chain/light chain variable domain fusion protein binding to the growth factor receptor c-erbB-2.

SEQ ID NO:5 is the amino acid sequence of the Fv heavy chain/light chain variable domain fusion protein binding to the growth factor receptor c-erbB-2 encoded by pWW52.

SEQ ID NO:6 is the nucleotide sequence of pWW616, which encodes the Fv heavy chain/light chain variable domain and alkaline phosphatase fusion protein Fv(FRP5)-phoA binding to the growth factor receptor c-erbB-2.

SEQ ID NO:7 is the amino acid sequence of Fv heavy chain/light chain variable domain and alkaline phosphatase fusion protein Fv(FRP5)-phoA binding to the growth factor receptor c-erbB-2 encoded by pWW616.

SEQ ID NO:8 is the nucleotide sequence of pWW15-VH51-1, which encodes the heavy chain variable domain of monoclonal antibody FWP51.

SEQ ID NO:9 is the nucleotide sequence of pWW15-VL51-1, which encodes the light chain variable domain of monoclonal antibody FWP51.

SEQ ID NO:10 is the nucleotide sequence of pWW15-Fv51, which encodes single-chain Fv fusion gene comprising monoclonal antibody FWP51 heavy and kappa light chain variable domains.

SEQ ID NO:11 is the amino acid sequence of single-chain Fv fusion gene comprising monoclonal antibody FWP51 heavy and kappa light chain variable domains, encoded by pWW15-Fv51.

SEQ ID NO:12 is the nucleotide sequence of pWW22, which encodes part of the mutated exotoxin A gene from *Pseudomonas aeruginosa* PAK.

SEQ ID NO:13 is the nucleotide sequence of pWW215-5, which encodes Fv heavy chain/light chain variable domain and exotoxin A fusion protein Fv(FRP5)-ETA binding to the c-erbB-2 protein.

SEQ ID NO:14 is the amino acid sequence of the Fv heavy chain/light chain variable domain and exotoxin A fusion protein Fv(FRP5)-ETA binding to the c-erbB-2 protein encoded by pWW215-5.

SEQ ID NO:15 is the nucleotide sequence of pWW215-51, which encodes Fv heavy chain/light chain variable domain and exotoxin A fusion protein Fv(FWP51)-ETA binding to the c-erbB-2 protein.

SEQ ID NO:16 is the amino acid sequence for Fv heavy chain/light chain variable domain and exotoxin A fusion protein Fv(FWP51)-ETA binding to the c-erbB-2 protein, encoded by pWW215-51.

SEQ ID NO:17 is the amino acid sequence of the three repetitive submits in the spacer group.

SEQ ID NO: 18, 19, 20, 21, and 22 are the nucleotide sequences of the oligonucleotide VH1FOR, MCK2, MCHC2, VH1BACK, VK1FOR, and VK1BACK, respectively.

SEQ ID NO: 24, 25, 26, 27, 28, and 29 are the nucleotide sequences of the oligonucleotides 1A, 1B, 2A, 2B, 3A, and 3B, respectively.

SEQ ID NO: 30 and 31 are the nucleotide sequences of the oligonucleotides $V_L5'$ and $V_L3'$, respectively.

SEQ ID NO:32 is the nucleotide sequence of the oligonucleotide junction.

SEQ ID NO: 33 and 34 are the nucleotide sequences of the oligonucleotides PhoA5' and PhoA3', respectively.

We claim:

1. A fusion protein comprising a single-chain recombinant antibody which binds to the extracellular domain of the growth factor receptor c-erbB-2 comprising a heavy chain variable domain and a light chain variable domain of a monoclonal antibody which domains are linked by a polypeptide spacer group and an effector molecule, and optionally comprising a peptide facilitating purification, a cleavage site and a peptide spacer; wherein the heavy chain variable domain and a light chain variable domain effector molecule are derived from a mouse monoclonal antibody selected form the group consisting of FRP5, FSP16, FWP51, and FSP77, deposited under the Budapest Treaty on Nov. 21, 1990 at the European Collection of Animal Cell Cultures (ECACC) in Porton Down. Salisbury, UK, under accession numbers 90112115, 90112116, 90112117, and 90112118, respectively.

2. The fusion protein of claim 1 wherein the mouse monoclonal antibody is FRP5.

3. The fusion protein of claim 1 wherein the mouse monoclonal antibody is FSP16.

4. The fusion protein of claim 1 wherein the mouse monoclonal antibody is FWP51.

5. The fusion protein of claim 1 wherein the mouse monoclonal antibody is FSP77.

6. A test kit for the qualitative and quantitative determination of c-erbB-2 protein comprising a recombinant antibody according to claim 1 and a buffer.

* * * * *

SEQUENCE LISTING

```
(1) GENERAL INFORMATION:

(iii) NUMBER OF SEQUENCES: 34

(2) INFORMATION FOR SEQ ID NO:1:

(i) SEQUENCE CHARACTERISTICS:
         (A) LENGTH: 361 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (A) ORGANISM: Mouse
         (C) INDIVIDUAL ISOLATE: E. coli (vii) IMMEDIATE SOURCE:
         (B) CLONE: pMZ16/1

(ix) FEATURE:
         (A) NAME/KEY: primer_bind
         (B) LOCATION: 6..27
         (D) OTHER INFORMATION: /note= "VH1BACK primer region"

(ix) FEATURE:
         (A) NAME/KEY: misc_feature
         (B) LOCATION: 95..328
         (D) OTHER INFORMATION: /note= "from 95 to 109 CDR1H; from
             152 to 202 CDR2H; from 299 to 328 CDR3H"

(ix) FEATURE:
         (A) NAME/KEY: primer_bind
         (B) LOCATION: 329..361
         (D) OTHER INFORMATION: /note= "VH1FOR primer region"

(xi) SEQUENCE DESCRIPTION: SEQ ID NO:1:
```

```
TCTAGAGGTG AAACTGCAGC AGTCTGGACC TGAACTGAAG AAGCCTGGAG AGACAGTCAA      60

GATCTCCTGC AAGGCCTCTG GGTATCCTTT CACAAACTAT GGAATGAACT GGGTGAAGCA     120

GGCTCCAGGA CAGGGTTTAA AGTGGATGGG CTGGATTAAC ACCTCCACTG GAGAGTCAAC     180

ATTTGCTGAT GACTTCAAGG GACGGTTTGA CTTCTCTTTG GAAACCTCTG CCAACACTGC     240

CTATTTGCAG ATCAACAACC TCAAAAGTGA AGACATGGCT ACATATTTCT GTGCAAGATG     300
6:

GGAGGTTTAC CACGGCTACG TTCCTTACTG GGGCCAAGGG ACCACGGTCA CCGTCTCCTC     360

A                                                                    361
```

(2) INFORMATION FOR SEQ ID NO:2:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Mouse
        (C) INDIVIDUAL ISOLATE: E. coli (vii) IMMEDIATE SOURCE:
        (B) CLONE: pMZ18/1

(ix) FEATURE:
        (A) NAME/KEY: primer_bind
        (B) LOCATION: 6..28
        (D) OTHER INFORMATION: /note= "MCK2 primer region"

(ix) FEATURE:
        (A) NAME/KEY: misc_feature
        (B) LOCATION: 98..319
        (D) OTHER INFORMATION: /note= "from 98 to 130 CDR1L; from
            176 to 196 CDR2L; from 293 to 319 CDR3L"

(ix) FEATURE:
        (A) NAME/KEY: primer_bind
        (B) LOCATION: 374..404
        (D) OTHER INFORMATION: /note= "MCK2 primer region"

(xi) SEQUENCE DESCRIPTION: SEQ ID NO:2:

```
TCTAGTCACT GGATGGTGGG AAGATGGAGA CATTGTGATG ACCCAGTCTC ACAAATTCCT      60

GTCCACTTCA GTAGGAGACA GGGTCAGCAT CACCTGCAAG GCCAGTCAGG ATGTGTATAA     120

TGCTGTTGCC TGGTATCAAC AGAAACCAGG ACAATCTCCT AAACTTCTGA TTTACTCGGC     180

ATCCTCCCGG TACACTGGAG TCCCTTCTCG CTTCACTGGC AGTGGCTCTG GCCGGATTT     240

CACTTTCACC ATCAGCAGTG TGCAGGCTGA AGACCTGGCA GTTTATTTCT GTCAGCAACA     300

TTTTCGTACT CCATTCACGT TCGGCTCGGG GACAAAATTG GAAATAAAAC GGGCTGATGC     360

TGCACCAACT GTATCCATCT TCCCACCATC CAGTGACTAG AACTAGA                  407
```

(2) INFORMATION FOR SEQ ID NO:3:

(i) SEQUENCE CHARACTERISTICS:
        (A) LENGTH: 175 base pairs
        (B) TYPE: nucleic acid
        (C) STRANDEDNESS: single
        (D) TOPOLOGY: linear

```
        (ii) MOLECULE TYPE: DNA (iii) HYPOTHETICAL: NO (iv) ANTI-SENSE: NO (vi) ORIGINAL SOURCE:
              (A) ORGANISM: Synthetic
              (C) INDIVIDUAL ISOLATE: E. coli (vii) IMMEDIATE SOURCE:
              (B) CLONE: pWW19

(ix) FEATURE:
              (A) NAME/KEY: misc_feature
              (B) LOCATION: 30..117
              (D) OTHER INFORMATION: /note= "30-35 PstI site;38-44
                   BstEII site for subcloning of heavy chain var
                   domain;54-98 coding seq of (GlyGlyGlyGlySer)3;
                   105-110 PvuII site; 112-117 BglII site (ix) FEATURE:
              (A) NAME/KEY: misc_feature
              (B) LOCATION: 120..125
              (D) OTHER INFORMATION: /note= "BclI site for subcloning of
                   light chain variable domain"

(xi) SEQUENCE DESCRIPTION: SEQ ID NO:3:

AAGCTTGCAT GCAAGCTTCT CAGGTACAAC TGCAGGAGGT CACCGTTTCC TCTGGCGGTG      60

GCGGTTCTGG TGGCGGTGGC TCCGGCGGTG GCGGTTCTGA CATCCAGCTG GAGATCTAGC     120

TGATCAAAGC TCTAGAGGAT CCCCGGGTAC CGAGCTCGAA TTCACTGGCC GTCGT         175

(2) INFORMATION FOR SEQ ID NO:4:

(i) SEQUENCE CHARACTERISTICS:
              (A) LENGTH: 748 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (A) ORGANISM: Mouse
              (C) INDIVIDUAL ISOLATE: E. coli (vii) IMMEDIATE SOURCE:
              (B) CLONE: pWW52

(ix) FEATURE:
              (A) NAME/KEY: CDS
              (B) LOCATION: 6..728

(ix) FEATURE:
              (A) NAME/KEY: misc_feature
              (B) LOCATION: 1..701
              (D) OTHER INFORMATION: /note= "1-8 synthetic spacer;9-365
                   FRP5 heavy chain var. domain;99-113 CDR1H;156-206
                   CDR2H;303-332 CDR3H;366-410 15 aa linker seq;411-728
                   FRP5 light chain var dom;480-512 CDR1L;558-578 CDR2L;
                   675-701 CDR3L (xi) SEQUENCE DESCRIPTION: SEQ ID NO:4:

AAGCT TCT CAG GTA CAA CTG CAG CAG TCT GGA CCT GAA CTG AAG AAG         47
      Ser Gln Val Gln Leu Gln Gln Ser Gly Pro Glu Leu Lys Lys
      1               5                   10

CCT GGA GAG ACA GTC AAG ATC TCC TGC AAG GCC TCT GGG TAT CCT TTC       95
Pro Gly Glu Thr Val Lys Ile Ser Cys Lys Ala Ser Gly Tyr Pro Phe
15                  20                  25                  30
```

```
ACA AAC TAT GGA ATG AAC TGG GTG AAG CAG GCT CCA GGA CAG GGT TTA    143
Thr Asn Tyr Gly Met Asn Trp Val Lys Gln Ala Pro Gly Gln Gly Leu
             35                  40                  45

AAG TGG ATG GGC TGG ATT AAC ACT TCC ACT GGA GAG TCA ACA TTT GCT    191
Lys Trp Met Gly Trp Ile Asn Thr Ser Thr Gly Glu Ser Thr Phe Ala
         50                  55                  60

GAT GAC TTC AAG GGA CGG TTT GAC TTC TCT TTG GAA ACC TCT GCC AAC    239
Asp Asp Phe Lys Gly Arg Phe Asp Phe Ser Leu Glu Thr Ser Ala Asn
     65                  70                  75

ACT GCC TAT TTG CAG ATC AAC AAC CTC AAA AGT GAA GAC ATG GCT ACA    287
Thr Ala Tyr Leu Gln Ile Asn Asn Leu Lys Ser Glu Asp Met Ala Thr
 80                  85                  90

TAT TTC TGT GCA AGA TGG GAG GTT TAC CAC GGC TAC GTT CCT TAC TGG    335
Tyr Phe Cys Ala Arg Trp Glu Val Tyr His Gly Tyr Val Pro Tyr Trp
 95                 100                 105                 110

GGC CAA GGG ACC ACG GTC ACC GTT TCC TCT GGC GGT GGC GGT TCT GGT    383
Gly Gln Gly Thr Thr Val Thr Val Ser Ser Gly Gly Gly Gly Ser Gly
                115                 120                 125

GGC GGT GGC TCC GGC GGT GGC GGT TCT GAC ATC CAG CTG ACC CAG TCT    431
Gly Gly Gly Ser Gly Gly Gly Gly Ser Asp Ile Gln Leu Thr Gln Ser
            130                 135                 140

CAC AAA TTC CTG TCC ACT TCA GTA GGA GAC AGG GTC AGC ATC ACC TGC    479
His Lys Phe Leu Ser Thr Ser Val Gly Asp Arg Val Ser Ile Thr Cys
        145                 150                 155

AAG GCC AGT CAG GAT GTG TAT AAT GCT GTT GCC TGG TAT CAA CAG AAA    527
Lys Ala Ser Gln Asp Val Tyr Asn Ala Val Ala Trp Tyr Gln Gln Lys
    160                 165                 170

CCA GGA CAA TCT CCT AAA CTT CTG ATT TAC TCG GCA TCC TCC CGG TAC    575
Pro Gly Gln Ser Pro Lys Leu Leu Ile Tyr Ser Ala Ser Ser Arg Tyr
175                 180                 185                 190

ACT GGA GTC CCT TCT CGC TTC ACT GGC AGT GGC TCT GGG CCG GAT TTC    623
Thr Gly Val Pro Ser Arg Phe Thr Gly Ser Gly Ser Gly Pro Asp Phe
                195                 200                 205

ACT TTC ACC ATC AGC AGT GTG CAG GCT GAA GAC CTG GCA GTT TAT TTC    671
Thr Phe Thr Ile Ser Ser Val Gln Ala Glu Asp Leu Ala Val Tyr Phe
            210                 215                 220

TGT CAG CAA CAT TTT CGT ACT CCA TTC ACG TTC GGC TCG GGG ACA AAA    719
Cys Gln Gln His Phe Arg Thr Pro Phe Thr Phe Gly Ser Gly Thr Lys
        225                 230                 235

TTG GAG ATC TAGCTGATCA AAGCTCTAGA                                  748
Leu Glu Ile
    240

(2) INFORMATION FOR SEQ ID NO:5:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:5:

Ser Gln Val Gln Leu Gln Gln Ser Gly Pro Glu Leu Lys Lys Pro Gly
  1               5                  10                  15

Glu Thr Val Lys Ile Ser Cys Lys Ala Ser Gly Tyr Pro Phe Thr Asn
             20                  25                  30

Tyr Gly Met Asn Trp Val Lys Gln Ala Pro Gly Gln Gly Leu Lys Trp
         35                  40                  45

Met Gly Trp Ile Asn Thr Ser Thr Gly Glu Ser Thr Phe Ala Asp Asp
     50                  55                  60
```

```
Phe Lys Gly Arg Phe Asp Phe Ser Leu Glu Thr Ser Ala Asn Thr Ala
 65                  70                  75                  80

Tyr Leu Gln Ile Asn Asn Leu Lys Ser Glu Asp Met Ala Thr Tyr Phe
                 85                  90                  95

Cys Ala Arg Trp Glu Val Tyr His Gly Tyr Val Pro Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Asp Ile Gln Leu Thr Gln Ser His Lys
130                 135                 140

Phe Leu Ser Thr Ser Val Gly Asp Arg Val Ser Ile Thr Cys Lys Ala
145                 150                 155                 160

Ser Gln Asp Val Tyr Asn Ala Val Ala Trp Tyr Gln Gln Lys Pro Gly
                165                 170                 175

Gln Ser Pro Lys Leu Leu Ile Tyr Ser Ala Ser Ser Arg Tyr Thr Gly
            180                 185                 190

Val Pro Ser Arg Phe Thr Gly Ser Gly Ser Gly Pro Asp Phe Thr Phe
            195                 200                 205

Thr Ile Ser Ser Val Gln Ala Glu Asp Leu Ala Val Tyr Phe Cys Gln
    210                 215                 220

Gln His Phe Arg Thr Pro Phe Thr Phe Gly Ser Gly Thr Lys Leu Glu
225                 230                 235                 240

Ile (2) INFORMATION FOR SEQ ID NO:6:

(i) SEQUENCE CHARACTERISTICS:
        (A) LENGTH: 2233 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Mouse and E. coli
        (C) INDIVIDUAL ISOLATE: E. coli (vii) IMMEDIATE SOURCE:
        (B) CLONE: pWW616

(ix) FEATURE:
        (A) NAME/KEY: CDS
        (B) LOCATION: 23..2155
        (D) OTHER INFORMATION: /note= "89-445 FRP5 heavy chain
            var.domain; 446-490 15 aa linker sequence; 491-814
            FRP5 light chain var.domain; 815-2155 coding region
            of phoA (ix) FEATURE:
        (A) NAME/KEY: 5'UTR
        (B) LOCATION: 1..22
        (D) OTHER INFORMATION: /function= "ompA 5'non-coding
            region"

(ix) FEATURE:
        (A) NAME/KEY: sig_peptide
        (B) LOCATION: 23..85
        (D) OTHER INFORMATION: /note= "ompA signal peptide"

(ix) FEATURE:
        (A) NAME/KEY: 3'UTR
        (B) LOCATION: 2156..2233
        (D) OTHER INFORMATION: /function= "phoA 3' non-coding
``` region"

(ix) FEATURE:
    (A) NAME/KEY: mat_peptide
    (B) LOCATION: 86..2155

(xi) SEQUENCE DESCRIPTION: SEQ ID NO:6:

```
TCTAGATAAC GAGGCGCAAA AA ATG AAA AAG ACA GCT ATC GCG ATT GCA GTG        52
                          Met Lys Lys Thr Ala Ile Ala Ile Ala Val
                          -21 -20                 -15

GCA CTG GCT GGT TTC GCT ACC GTA GCG CAA GCT TCT CAG GTA CAA CTG        100
Ala Leu Ala Gly Phe Ala Thr Val Ala Gln Ala Ser Gln Val Gln Leu
        -10                  -5                   1               5

CAG CAG TCT GGA CCT GAA CTG AAG AAG CCT GGA GAG ACA GTC AAG ATC        148
Gln Gln Ser Gly Pro Glu Leu Lys Lys Pro Gly Glu Thr Val Lys Ile
                10                  15                  20

TCC TGC AAG GCC TCT GGG TAT CCT TTC ACA AAC TAT GGA ATG AAC TGG        196
Ser Cys Lys Ala Ser Gly Tyr Pro Phe Thr Asn Tyr Gly Met Asn Trp
            25                  30                  35

GTG AAG CAG GCT CCA GGA CAG GGT TTA AAG TGG ATG GGC TGG ATT AAC        244
Val Lys Gln Ala Pro Gly Gln Gly Leu Lys Trp Met Gly Trp Ile Asn
        40                  45                  50

ACC TCC ACT GGA GAG TCA ACA TTT GCT GAT GAC TTC AAG GGA CGG TTT        292
Thr Ser Thr Gly Glu Ser Thr Phe Ala Asp Asp Phe Lys Gly Arg Phe
    55                  60                  65

GAC TTC TCT TTG GAA ACC TCT GCC AAC ACT GCC TAT TTG CAG ATC AAC        340
Asp Phe Ser Leu Glu Thr Ser Ala Asn Thr Ala Tyr Leu Gln Ile Asn
70                  75                  80                  85

AAC CTC AAA AGT GAA GAC ATG GCT ACA TAT TTC TGT GCA AGA TGG GAG        388
Asn Leu Lys Ser Glu Asp Met Ala Thr Tyr Phe Cys Ala Arg Trp Glu
                90                  95                  100

GTT TAC CAC GGC TAC GTT CCT TAC TGG GGC CAA GGG ACC ACG GTC ACC        436
Val Tyr His Gly Tyr Val Pro Tyr Trp Gly Gln Gly Thr Thr Val Thr
            105                 110                 115

GTT TCC TCT GGC GGT GGC GGT TCT GGT GGC GGT GGC TCC GGC GGT GGC        484
Val Ser Ser Gly Gly Gly Gly Ser Gly Gly Gly Gly Ser Gly Gly Gly
        120                 125                 130

GGT TCT GAC ATC CAG CTG ACC CAG TCT CAC AAA TTC CTG TCC ACT TCA        532
Gly Ser Asp Ile Gln Leu Thr Gln Ser His Lys Phe Leu Ser Thr Ser
    135                 140                 145

GTA GGA GAC AGG GTC AGC ATC ACC TGC AAG GCC AGT CAG GAT GTG TAT        580
Val Gly Asp Arg Val Ser Ile Thr Cys Lys Ala Ser Gln Asp Val Tyr
150                 155                 160                 165

AAT GCT GTT GCC TGG TAT CAA CAG AAA CCA GGA CAA TCT CCT AAA CTT        628
Asn Ala Val Ala Trp Tyr Gln Gln Lys Pro Gly Gln Ser Pro Lys Leu
                170                 175                 180

CTG ATT TAC TCG GCA TCC TCC CGG TAC ACT GGA GTC CCT TCT CGC TTC        676
Leu Ile Tyr Ser Ala Ser Ser Arg Tyr Thr Gly Val Pro Ser Arg Phe
            185                 190                 195

ACT GGC AGT GGC TCT GGG CCG GAT TTC ACT TTC ACC ATC AGC AGT GTG        724
Thr Gly Ser Gly Ser Gly Pro Asp Phe Thr Phe Thr Ile Ser Ser Val
        200                 205                 210

CAG GCT GAA GAC CTG GCA GTT TAT TTC TGT CAG CAA CAT TTT CGT ACT        772
Gln Ala Glu Asp Leu Ala Val Tyr Phe Cys Gln Gln His Phe Arg Thr
    215                 220                 225

CCA TTC ACG TTC GGC TCG GGG ACA AAA TTG GAG ATC AAA GCT CTA GAG        820
Pro Phe Thr Phe Gly Ser Gly Thr Lys Leu Glu Ile Lys Ala Leu Glu
230                 235                 240                 245

CCT GTT CTG GAA AAC CGG GCT GCT CAG GGC GAT ATT ACT GCA CCC GGC        868
Pro Val Leu Glu Asn Arg Ala Ala Gln Gly Asp Ile Thr Ala Pro Gly
                250                 255                 260
```

-continued

| | |
|---|---|
| GGT GCT CGC CGT TTA ACG GGT GAT CAG ACT GCC GCT CTG CGT GAT TCT<br>Gly Ala Arg Arg Leu Thr Gly Asp Gln Thr Ala Ala Leu Arg Asp Ser<br>265                              270                          275 | 916 |
| CTT AGC GAT AAA CCT GCA AAA AAT ATT ATT TTG CTG ATT GGC GAT GGG<br>Leu Ser Asp Lys Pro Ala Lys Asn Ile Ile Leu Leu Ile Gly Asp Gly<br>            280                          285                          290 | 964 |
| ATG GGG GAC TCG GAA ATT ACT GCC GCA CGT AAT TAT GCC GAA GGT GCG<br>Met Gly Asp Ser Glu Ile Thr Ala Ala Arg Asn Tyr Ala Glu Gly Ala<br>295                              300                          305 | 1012 |
| GGC GGC TTT TTT AAA GGT ATA GAT GCC TTA CCG CTT ACC GGG CAA TAC<br>Gly Gly Phe Phe Lys Gly Ile Asp Ala Leu Pro Leu Thr Gly Gln Tyr<br>310                              315                          320                        325 | 1060 |
| ACT CAC TAT GCG CTG AAT AAA AAA ACC GGC AAA CCG GAC TAC GTC ACC<br>Thr His Tyr Ala Leu Asn Lys Lys Thr Gly Lys Pro Asp Tyr Val Thr<br>                      330                          335                          340 | 1108 |
| GAC TCG GCT GCA TCA GCA ACC GCC TGG TCA ACC GGT GTC AAA ACC TAT<br>Asp Ser Ala Ala Ser Ala Thr Ala Trp Ser Thr Gly Val Lys Thr Tyr<br>                     345                          350                          355 | 1156 |
| AAC GGC GCG CTG GGC GTC GAT ATT CAC GAA AAA GAT CAC CCA ACG ATT<br>Asn Gly Ala Leu Gly Val Asp Ile His Glu Lys Asp His Pro Thr Ile<br>                  360                          365                          370 | 1204 |
| CTG GAA ATG GCA AAA GCC GCA GGT CTG GCG ACC GGT AAC GTT TCT ACC<br>Leu Glu Met Ala Lys Ala Ala Gly Leu Ala Thr Gly Asn Val Ser Thr<br>375                              380                          385 | 1252 |
| GCA GAG TTG CAG GAT GCC ACG CCC GCT GCG CTG GTG GCA CAT GTG ACC<br>Ala Glu Leu Gln Asp Ala Thr Pro Ala Ala Leu Val Ala His Val Thr<br>390                              395                          400                        405 | 1300 |
| TCG CGC AAA TGC TAC GGT CCG AGC GCG ACC AGT GAA AAA TGT CCG GGT<br>Ser Arg Lys Cys Tyr Gly Pro Ser Ala Thr Ser Glu Lys Cys Pro Gly<br>                     410                          415                          420 | 1348 |
| AAC GCT CTG GAA AAA GGC GGA AAA GGA TCG ATT ACC GAA CAG CTG CTT<br>Asn Ala Leu Glu Lys Gly Gly Lys Gly Ser Ile Thr Glu Gln Leu Leu<br>                  425                          430                          435 | 1396 |
| AAC GCT CGT GCC GAC GTT ACG CTT GGC GGC GGC GCA AAA ACC TTT GCT<br>Asn Ala Arg Ala Asp Val Thr Leu Gly Gly Gly Ala Lys Thr Phe Ala<br>                  440                          445                          450 | 1444 |
| GAA ACG GCA ACC GCT GGT GAA TGG CAG GGA AAA ACG CTG CGT GAA CAG<br>Glu Thr Ala Thr Ala Gly Glu Trp Gln Gly Lys Thr Leu Arg Glu Gln<br>455                              460                          465 | 1492 |
| GCA CAG GCG CGT GGT TAT CAG TTG GTG AGC GAT GCT GCC TCA CTG AAT<br>Ala Gln Ala Arg Gly Tyr Gln Leu Val Ser Asp Ala Ala Ser Leu Asn<br>470                              475                          480                        485 | 1540 |
| TCG GTG ACG GAA GCG AAT CAG CAA AAA CCC CTG CTT GGC CTG TTT GCT<br>Ser Val Thr Glu Ala Asn Gln Gln Lys Pro Leu Leu Gly Leu Phe Ala<br>                     490                          495                          500 | 1588 |
| GAC GGC AAT ATG CCA GTG CGC TGG CTA GGA CCG AAA GCA ACG TAC CAT<br>Asp Gly Asn Met Pro Val Arg Trp Leu Gly Pro Lys Ala Thr Tyr His<br>                  505                          510                          515 | 1636 |
| GGC AAT ATC GAT AAG CCC GCA GTC ACC TGT ACG CCA AAT CCG CAA CGT<br>Gly Asn Ile Asp Lys Pro Ala Val Thr Cys Thr Pro Asn Pro Gln Arg<br>                  520                          525                          530 | 1684 |
| AAT GAC AGT GTA CCA ACC CTG GCG CAG ATG ACC GAC AAA GCC ATT GAA<br>Asn Asp Ser Val Pro Thr Leu Ala Gln Met Thr Asp Lys Ala Ile Glu<br>535                              540                          545 | 1732 |
| TTG TTG AGT AAA AAT GAG AAA GGC TTT TTC CTG CAA GTT GAA GGT GCG<br>Leu Leu Ser Lys Asn Glu Lys Gly Phe Phe Leu Gln Val Glu Gly Ala<br>550                              555                          560                        565 | 1780 |
| TCA ATC GAT AAA CAG GAT CAT GCT GCG AAT CCT TGT GGG CAA ATT GGC<br>Ser Ile Asp Lys Gln Asp His Ala Ala Asn Pro Cys Gly Gln Ile Gly<br>                  570                          575                          580 | 1828 |

-continued

```
GAG ACG GTC GAT CTC GAT GAA GCC GTA CAA CGG GCG CTG GAA TTC GCT    1876
Glu Thr Val Asp Leu Asp Glu Ala Val Gln Arg Ala Leu Glu Phe Ala
        585                 590                 595

AAA AAG GAG GGT AAC ACG CTG GTC ATA GTC ACC GCT GAT CAC GCC CAC    1924
Lys Lys Glu Gly Asn Thr Leu Val Ile Val Thr Ala Asp His Ala His
            600                 605                 610

GCC AGC CAG ATT GTT GCG CCG GAT ACC AAA GCT CCG GGC CTC ACC CAG    1972
Ala Ser Gln Ile Val Ala Pro Asp Thr Lys Ala Pro Gly Leu Thr Gln
    615                 620                 625

GCG CTA AAT ACC AAA GAT GGC GCA GTG ATG GTG ATG AGT TAC GGG AAC    2020
Ala Leu Asn Thr Lys Asp Gly Ala Val Met Val Met Ser Tyr Gly Asn
630                 635                 640                 645

TCC GAA GAG GAT TCA CAA GAA CAT ACC GGC AGT CAG TTG CGT ATT GCG    2068
Ser Glu Glu Asp Ser Gln Glu His Thr Gly Ser Gln Leu Arg Ile Ala
                650                 655                 660

GCG TAT GGC CCG CAT GCC GCC AAT GTT GTT GGA CTG ACC GAC CAG ACC    2116
Ala Tyr Gly Pro His Ala Ala Asn Val Val Gly Leu Thr Asp Gln Thr
            665                 670                 675

GAT CTC TTC TAC ACC ATG AAA GCC GCT CTG GGG CTG AAA TAAAACCGCG    2165
Asp Leu Phe Tyr Thr Met Lys Ala Ala Leu Gly Leu Lys
        680                 685                 690

CCCGGCAGTG AATTTTCGCT GCCGGGTGGT TTTTTTGCTG TTAGCAACCA GACTTAATGG    2225

CAGAGCTC                                                              2233
```

(2) INFORMATION FOR SEQ ID NO:7:

(i) SEQUENCE CHARACTERISTICS:
      (A) LENGTH: 711 amino acids
      (B) TYPE: amino acid
      (D) TOPOLOGY: linear (ii) MOLECULE TYPE: protein (xi) SEQUENCE DESCRIPTION: SEQ ID NO:7:

```
Met Lys Lys Thr Ala Ile Ala Ile Ala Val Ala Leu Ala Gly Phe Ala
-21 -20                 -15                 -10

Thr Val Ala Gln Ala Ser Gln Val Gln Leu Gln Gln Ser Gly Pro Glu
 -5              1                   5                  10

Leu Lys Lys Pro Gly Glu Thr Val Lys Ile Ser Cys Lys Ala Ser Gly
                15                  20                  25

Tyr Pro Phe Thr Asn Tyr Gly Met Asn Trp Val Lys Gln Ala Pro Gly
            30                  35                  40

Gln Gly Leu Lys Trp Met Gly Trp Ile Asn Thr Thr Gly Glu Ser
         45                  50                  55

Thr Phe Ala Asp Asp Phe Lys Gly Arg Phe Asp Phe Ser Leu Glu Thr
 60              65                  70                  75

Ser Ala Asn Thr Ala Tyr Leu Gln Ile Asn Asn Leu Lys Ser Glu Asp
                80                  85                  90

Met Ala Thr Tyr Phe Cys Ala Arg Trp Glu Val Tyr His Gly Tyr Val
             95                 100                 105

Pro Tyr Trp Gly Gln Gly Thr Thr Val Thr Val Ser Ser Gly Gly Gly
        110                 115                 120

Gly Ser Gly Gly Gly Gly Ser Gly Gly Gly Gly Ser Asp Ile Gln Leu
    125                 130                 135

Thr Gln Ser His Lys Phe Leu Ser Thr Ser Val Gly Asp Arg Val Ser
140                 145                 150                 155

Ile Thr Cys Lys Ala Ser Gln Asp Val Tyr Asn Ala Val Ala Trp Tyr
                160                 165                 170
```

-continued

```
Gln Gln Lys Pro Gly Gln Ser Pro Lys Leu Leu Ile Tyr Ser Ala Ser
            175                 180                 185

Ser Arg Tyr Thr Gly Val Pro Ser Arg Phe Thr Gly Ser Gly Ser Gly
            190                 195                 200

Pro Asp Phe Thr Phe Thr Ile Ser Ser Val Gln Ala Glu Asp Leu Ala
205                 210                 215

Val Tyr Phe Cys Gln Gln His Phe Arg Thr Pro Phe Thr Phe Gly Ser
220                 225                 230                 235

Gly Thr Lys Leu Glu Ile Lys Ala Leu Glu Pro Val Leu Glu Asn Arg
            240                 245                 250

Ala Ala Gln Gly Asp Ile Thr Ala Pro Gly Gly Ala Arg Arg Leu Thr
            255                 260                 265

Gly Asp Gln Thr Ala Ala Leu Arg Asp Ser Leu Ser Asp Lys Pro Ala
            270                 275                 280

Lys Asn Ile Ile Leu Leu Ile Gly Asp Gly Met Gly Asp Ser Glu Ile
285                 290                 295

Thr Ala Ala Arg Asn Tyr Ala Glu Gly Ala Gly Gly Phe Phe Lys Gly
300                 305                 310                 315

Ile Asp Ala Leu Pro Leu Thr Gly Gln Tyr Thr His Tyr Ala Leu Asn
            320                 325                 330

Lys Lys Thr Gly Lys Pro Asp Tyr Val Thr Asp Ser Ala Ala Ser Ala
            335                 340                 345

Thr Ala Trp Ser Thr Gly Val Lys Thr Tyr Asn Gly Ala Leu Gly Val
            350                 355                 360

Asp Ile His Glu Lys Asp His Pro Thr Ile Leu Glu Met Ala Lys Ala
365                 370                 375

Ala Gly Leu Ala Thr Gly Asn Val Ser Thr Ala Glu Leu Gln Asp Ala
380                 385                 390                 395

Thr Pro Ala Ala Leu Val Ala His Val Thr Ser Arg Lys Cys Tyr Gly
                400                 405                 410

Pro Ser Ala Thr Ser Glu Lys Cys Pro Gly Asn Ala Leu Glu Lys Gly
            415                 420                 425

Gly Lys Gly Ser Ile Thr Glu Gln Leu Leu Asn Ala Arg Ala Asp Val
            430                 435                 440

Thr Leu Gly Gly Gly Ala Lys Thr Phe Ala Glu Thr Ala Thr Ala Gly
            445                 450                 455

Glu Trp Gln Gly Lys Thr Leu Arg Glu Gln Ala Gln Ala Arg Gly Tyr
460                 465                 470                 475

Gln Leu Val Ser Asp Ala Ala Ser Leu Asn Ser Val Thr Glu Ala Asn
                480                 485                 490

Gln Gln Lys Pro Leu Leu Gly Leu Phe Ala Asp Gly Asn Met Pro Val
            495                 500                 505

Arg Trp Leu Gly Pro Lys Ala Thr Tyr His Gly Asn Ile Asp Lys Pro
            510                 515                 520

Ala Val Thr Cys Thr Pro Asn Pro Gln Arg Asn Asp Ser Val Pro Thr
            525                 530                 535

Leu Ala Gln Met Thr Asp Lys Ala Ile Glu Leu Leu Ser Lys Asn Glu
540                 545                 550                 555

Lys Gly Phe Phe Leu Gln Val Glu Gly Ala Ser Ile Asp Lys Gln Asp
            560                 565                 570

His Ala Ala Asn Pro Cys Gly Gln Ile Gly Glu Thr Val Asp Leu Asp
            575                 580                 585

Glu Ala Val Gln Arg Ala Leu Glu Phe Ala Lys Lys Glu Gly Asn Thr
            590                 595                 600
```

```
Leu Val Ile Val Thr Ala Asp His Ala His Ala Ser Gln Ile Val Ala
        605                 610                 615

Pro Asp Thr Lys Ala Pro Gly Leu Thr Gln Ala Leu Asn Thr Lys Asp
620                 625                 630                 635

Gly Ala Val Met Val Met Ser Tyr Gly Asn Ser Glu Glu Asp Ser Gln
                640                 645                 650

Glu His Thr Gly Ser Gln Leu Arg Ile Ala Ala Tyr Gly Pro His Ala
            655                 660                 665

Ala Asn Val Val Gly Leu Thr Asp Gln Thr Asp Leu Phe Tyr Thr Met
        670                 675                 680

Lys Ala Ala Leu Gly Leu Lys
        685                 690
```

(2) INFORMATION FOR SEQ ID NO:8:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Mouse
        (C) INDIVIDUAL ISOLATE: E. coli (vii) IMMEDIATE SOURCE:
        (B) CLONE: pWW15-VH51-1

(ix) FEATURE:
        (A) NAME/KEY: misc_feature
        (B) LOCATION: 1..342
        (D) OTHER INFORMATION: /note= "1-14 partial seq. of
            VH1BACK primer region; 82-96 CDR1H; 139-189 CDR2H;
            286-318 CDR3H; 317-342 partial seq. of VH1FOR primer
            region (xi) SEQUENCE DESCRIPTION: SEQ ID NO:8:

```
CTGCAGCAGT CTGGGGCTGA GCTGGTGAGG CCTGGGACTT CAGTGAAGCT GTCCTGCAAG    60

GCTTCTGATT ACACCTTCAC CAGCTACTGG ATGAACTGGG TGAAGCAGAG GCCTGGACAA   120

GGCCTTGAAT GGATTGGTAT GATTGATCCT TCAGACAGTG AAACTCAATA CAATCAAATG   180

TTCAAGGACA AGGCCGCATT GACTGTAGAC AAGTCCTCCA ATACAGCCTA CATGCAACTC   240

AGCAGCCTGA CATCTGAGGA CTCTGCGGTC TATTACTGTG CAAAAGGGGG GGCCTCTGGG   300

GACTGGTACT TCGATGTCTG GGGCCAAGGG ACCACGGTCA CC                     342
```

(2) INFORMATION FOR SEQ ID NO:9:

(i) SEQUENCE CHARACTERISTICS:
        (A) LENGTH: 310 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Mouse

```
          (C) INDIVIDUAL ISOLATE: E. coli (vii) IMMEDIATE SOURCE:
          (B) CLONE: pWW15-VL51-1

(ix) FEATURE:
          (A) NAME/KEY: misc_feature
          (B) LOCATION: 1..310
          (D) OTHER INFORMATION: /note= "1-18 partial seq. of
              VK1BACK primer region; 64-96 CDR1L; 142-162 CDR2L;
              259-282 CDR3L; 292-310 partial seq. of VK1FOR
              primer region (xi) SEQUENCE DESCRIPTION: SEQ ID NO:9:

CAGCTGACCC AGTCTCCATC CTCACTGTCT GCATCTCTGG GAGGCGAAGT CACCATCACT      60

TGCAAGGCAA GCCAAGACAT TAAGAAGTAT ATAGCTTGGT ACCAACACAA GCCTGGAAAA     120

AGTCCTCGGC TACTCATACA CTACACATCT GTATTACAGC CAGGCATCCC ATCCAGGTTC     180

AGTGGAAGTG GGTCTGGGAG AGATTATTCC TTCAGCATCC ACAACCTGGA GCCTGAAGAT     240

ATTGCAACTT ATTATTGTCT ACATTATGAT TATCTGTACA CGTTCGGAGG GGGCACCAAG     300

CTGGAGATCT                                                           310

(2) INFORMATION FOR SEQ ID NO:10:

(i) SEQUENCE CHARACTERISTICS:
          (A) LENGTH: 748 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (A) ORGANISM: Mouse
          (C) INDIVIDUAL ISOLATE: E. coli (vii) IMMEDIATE SOURCE:
          (B) CLONE: pWW15-Fv51

(ix) FEATURE:
          (A) NAME/KEY: CDS
          (B) LOCATION: 6..728
          (D) OTHER INFORMATION: /note= "1-8 synthetic spacer;9-368
              FWP51 Heavy ChainVar.Dom.;99-113 CDR1H;156-206
              CDR2H;303-335 CDR3H;369-413 Syn.Spcr;414-728 FWP51
              Light ChainVar.Dom;483-515 CDR1L;561-581 CDR2L;
              729-748 Syn.Spcr.

(xi) SEQUENCE DESCRIPTION: SEQ ID NO:10:

AAGCT TCT CAG GTA CAA CTG CAG CAG TCT GGG GCT GAG CTG GTG AGG          47
      Ser Gln Val Gln Leu Gln Gln Ser Gly Ala Glu Leu Val Arg
       1               5                   10

CCT GGG ACT TCA GTG AAG CTG TCC TGC AAG GCT TCT GAT TAC ACC TTC        95
Pro Gly Thr Ser Val Lys Leu Ser Cys Lys Ala Ser Asp Tyr Thr Phe
 15                  20                  25                  30

ACC AGC TAC TGG ATG AAC TGG GTG AAG CAG AGG CCT GGA CAA GGC CTT       143
Thr Ser Tyr Trp Met Asn Trp Val Lys Gln Arg Pro Gly Gln Gly Leu
             35                  40                  45

GAA TGG ATT GGT ATG ATT GAT CCT TCA GAC AGT GAA ACT CAA TAC AAT       191
Glu Trp Ile Gly Met Ile Asp Pro Ser Asp Ser Glu Thr Gln Tyr Asn
                 50                  55                  60

CAA ATG TTC AAG GAC AAG GCC GCA TTG ACT GTA GAC AAG TCC TCC AAT       239
Gln Met Phe Lys Asp Lys Ala Ala Leu Thr Val Asp Lys Ser Ser Asn
         65                  70                  75
```

```
ACA GCC TAC ATG CAA CTC AGC AGC CTG ACA TCT GAG GAC TCT GCG GTC      287
Thr Ala Tyr Met Gln Leu Ser Ser Leu Thr Ser Glu Asp Ser Ala Val
    80                  85                  90

TAT TAC TGT GCA AAA GGG GGG GCC TCT GGG GAC TGG TAC TTC GAT GTC      335
Tyr Tyr Cys Ala Lys Gly Gly Ala Ser Gly Asp Trp Tyr Phe Asp Val
95              100                 105                 110

TGG GGC CAA GGG ACC ACG GTC ACC GTT TCC TCT GGC GGT GGC GGT TCT      383
Trp Gly Gln Gly Thr Thr Val Thr Val Ser Ser Gly Gly Gly Gly Ser
                115                 120                 125

GGT GGC GGT GGC TCC GGC GGT GGC GGT TCT GAC ATC CAG CTG ACC CAG      431
Gly Gly Gly Gly Ser Gly Gly Gly Gly Ser Asp Ile Gln Leu Thr Gln
            130                 135                 140

TCT CCA TCC TCA CTG TCT GCA TCT CTG GGA GGC GAA GTC ACC ATC ACT      479
Ser Pro Ser Ser Leu Ser Ala Ser Leu Gly Gly Glu Val Thr Ile Thr
            145                 150                 155

TGC AAG GCA AGC CAA GAC ATT AAG AAG TAT ATA GCT TGG TAC CAA CAC      527
Cys Lys Ala Ser Gln Asp Ile Lys Lys Tyr Ile Ala Trp Tyr Gln His
        160                 165                 170

AAG CCT GGA AAA AGT CCT CGG CTA CTC ATA CAC TAC ACA TCT GTA TTA      575
Lys Pro Gly Lys Ser Pro Arg Leu Leu Ile His Tyr Thr Ser Val Leu
175                 180                 185                 190

CAG CCA GGC ATC CCA TCC AGG TTC AGT GGA AGT GGG TCT GGG AGA GAT      623
Gln Pro Gly Ile Pro Ser Arg Phe Ser Gly Ser Gly Ser Gly Arg Asp
                195                 200                 205

TAT TCC TTC AGC ATC CAC AAC CTG GAG CCT GAA GAT ATT GCA ACT TAT      671
Tyr Ser Phe Ser Ile His Asn Leu Glu Pro Glu Asp Ile Ala Thr Tyr
            210                 215                 220

TAT TGT CTA CAT TAT GAT TAT CTG TAC ACG TTC GGA GGG GGC ACC AAG      719
Tyr Cys Leu His Tyr Asp Tyr Leu Tyr Thr Phe Gly Gly Gly Thr Lys
        225                 230                 235

CTG GAG ATC TAGCTGATCA AAGCTCTAGA                                    748
Leu Glu Ile
240
```

(2) INFORMATION FOR SEQ ID NO:11:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:11:

```
Ser Gln Val Gln Leu Gln Gln Ser Gly Ala Glu Leu Val Arg Pro Gly
1               5                   10                  15

Thr Ser Val Lys Leu Ser Cys Lys Ala Ser Asp Tyr Thr Phe Thr Ser
            20                  25                  30

Tyr Trp Met Asn Trp Val Lys Gln Arg Pro Gly Gln Gly Leu Glu Trp
        35                  40                  45

Ile Gly Met Ile Asp Pro Ser Asp Ser Glu Thr Gln Tyr Asn Gln Met
    50                  55                  60

Phe Lys Asp Lys Ala Ala Leu Thr Val Asp Lys Ser Ser Asn Thr Ala
65                  70                  75                  80

Tyr Met Gln Leu Ser Ser Leu Thr Ser Glu Asp Ser Ala Val Tyr Tyr
                85                  90                  95

Cys Ala Lys Gly Gly Ala Ser Gly Asp Trp Tyr Phe Asp Val Trp Gly
            100                 105                 110

Gln Gly Thr Thr Val Thr Val Ser Ser Gly Gly Gly Gly Ser Gly Gly
        115                 120                 125
```

```
Gly Gly Ser Gly Gly Gly Ser Asp Ile Gln Leu Thr Gln Ser Pro
    130             135                 140

Ser Ser Leu Ser Ala Ser Leu Gly Gly Glu Val Thr Ile Thr Cys Lys
145             150              155                     160

Ala Ser Gln Asp Ile Lys Lys Tyr Ile Ala Trp Tyr Gln His Lys Pro
                165             170                 175

Gly Lys Ser Pro Arg Leu Leu Ile His Tyr Thr Ser Val Leu Gln Pro
        180             185                 190

Gly Ile Pro Ser Arg Phe Ser Gly Ser Gly Ser Gly Arg Asp Tyr Ser
        195             200                 205

Phe Ser Ile His Asn Leu Glu Pro Glu Asp Ile Ala Thr Tyr Tyr Cys
    210             215                 220

Leu His Tyr Asp Tyr Leu Tyr Thr Phe Gly Gly Gly Thr Lys Leu Glu
225             230                 235                 240

Ile
```

(2) INFORMATION FOR SEQ ID NO:12:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Pseudomonas aeruginosa PAK
        (C) INDIVIDUAL ISOLATE: E. coli (vii) IMMEDIATE SOURCE:
        (B) CLONE: pWW22

(ix) FEATURE:
        (A) NAME/KEY: misc_feature
        (B) LOCATION: 1..201
        (D) OTHER INFORMATION: /note= "from 1 to 27 synthetic
           spacer; from 29 to 201 partial exotoxin A sequence
           corresponding to nucleotide positions 1574 to 1747
           bp of the exotoxin A sequence (Gray et al.)

(x) PUBLICATION INFORMATION:
        (A) AUTHORS: Gray, et al.
        (C) JOURNAL: Proc. Natl. Acad. Sci. U.S.A.
        (D) VOLUME: 81
        (F) PAGES: 2645-2649
        (G) DATE: 1984
        (K) RELEVANT RESIDUES IN SEQ ID NO:12: FROM 29 TO 201

(xi) SEQUENCE DESCRIPTION: SEQ ID NO:12:

```
AAGCTTAAGG AGATCTGCAT GCTTCTAGAG GGCGGCAGCC TGGCCGCGCT GACCGCGCAC      60

CAGGCCTGCC ACCTGCCGCT GGAGACTTTC ACCCGTCATC GCCAGCCGCG CGGCTGGGAA     120

CAACTGGAGC AGTGCGGCTA TCCGGTGCAG CGGCTGGTCG CCCTCTACCT GGCGGCGCGA     180

CTGTCATGGA ACCAGGTCGA C                                              201
```

(2) INFORMATION FOR SEQ ID NO:13:

(i) SEQUENCE CHARACTERISTICS:
        (A) LENGTH: 2012 base pairs
        (B) TYPE: nucleic acid
        (C) STRANDEDNESS: single
        (D) TOPOLOGY: linear

```
    (ii) MOLECULE TYPE: DNA (iii) HYPOTHETICAL: NO (iv) ANTI-SENSE: NO (vi) ORIGINAL SOURCE:
         (A) ORGANISM: Mouse/Pseudomonas aeruginosa
         (C) INDIVIDUAL ISOLATE: E. coli (vii) IMMEDIATE SOURCE:
         (B) CLONE: pWW215-5

(ix) FEATURE:
         (A) NAME/KEY: CDS
         (B) LOCATION: 1..1911
         (D) OTHER INFORMATION: /note= "64-87 FLAG peptide and
             enterokinase cleavage site; 97-453 heavy chain
             variable domain;454-498 15 aa linker sequence;
             499-822 FRP5 light chain variable domain (ix) FEATURE:
         (A) NAME/KEY: sig_peptide
         (B) LOCATION: 1..63
         (D) OTHER INFORMATION: /note= "ompA signal peptide"

(ix) FEATURE:
         (A) NAME/KEY: mat_peptide
         (B) LOCATION: 94..1911

(ix) FEATURE:
         (A) NAME/KEY: 3'UTR
         (B) LOCATION: 1912..2012
         (D) OTHER INFORMATION: /function= "3'non-coding region of
             the exotoxin A gene"

(ix) FEATURE:
         (A) NAME/KEY: misc_feature
         (B) LOCATION: 826..1911
         (D) OTHER INFORMATION: /note= "Exotoxin A gene coding
             region (coding for amino acids 252 to 613 of the
             mature exotoxin A)"

(xi) SEQUENCE DESCRIPTION: SEQ ID NO:13:

ATG AAA AAG ACA GCT ATC GCG ATT GCA GTG GCA CTG GCT GGT TTC GCT        48
Met Lys Lys Thr Ala Ile Ala Ile Ala Val Ala Leu Ala Gly Phe Ala
-31 -30                 -25                 -20

ACC GTT GCG CAA GCT GAC TAC AAG GAC GAC GAT GAC AAG CTA GCT TCT        96
Thr Val Ala Gln Ala Asp Tyr Lys Asp Asp Asp Asp Lys Leu Ala Ser
-15             -10                  -5                         1

CAG GTA CAA CTG CAG CAG TCT GGA CCT GAA CTG AAG AAG CCT GGA GAG       144
Gln Val Gln Leu Gln Gln Ser Gly Pro Glu Leu Lys Lys Pro Gly Glu
            5                  10                 15

ACA GTC AAG ATC TCC TGC AAG GCC TCT GGG TAT CCT TTC ACA AAC TAT       192
Thr Val Lys Ile Ser Cys Lys Ala Ser Gly Tyr Pro Phe Thr Asn Tyr
        20                  25                 30

GGA ATG AAC TGG GTG AAG CAG GCT CCA GGA CAG GGT TTA AAG TGG ATG       240
Gly Met Asn Trp Val Lys Gln Ala Pro Gly Gln Gly Leu Lys Trp Met
    35                  40                  45

GGC TGG ATT AAC ACC TCC ACT GGA GAG TCA ACA TTT GCT GAT GAC TTC       288
Gly Trp Ile Asn Thr Ser Thr Gly Glu Ser Thr Phe Ala Asp Asp Phe
50                  55                  60                  65

AAG GGA CGG TTT GAC TTC TCT TTG GAA ACC TCT GCC AAC ACT GCC TAT       336
Lys Gly Arg Phe Asp Phe Ser Leu Glu Thr Ser Ala Asn Thr Ala Tyr
                70                  75                  80

TTG CAG ATC AAC AAC CTC AAA AGT GAA GAC ATG GCT ACA TAT TTC TGT       384
Leu Gln Ile Asn Asn Leu Lys Ser Glu Asp Met Ala Thr Tyr Phe Cys
            85                  90                  95

GCA AGA TGG GAG GTT TAC CAC GGC TAC GTT CCT TAC TGG GGC CAA GGG       432
Ala Arg Trp Glu Val Tyr His Gly Tyr Val Pro Tyr Trp Gly Gln Gly
        100                 105                 110
```

```
ACC ACG GTC ACC GTT TCC TCT GGC GGT GGC GGT TCT GGT GGC GGT GGC      480
Thr Thr Val Thr Val Ser Ser Gly Gly Gly Gly Ser Gly Gly Gly Gly
    115                 120                 125

TCC GGC GGT GGC GGT TCT GAC ATC CAG CTG ACC CAG TCT CAC AAA TTC      528
Ser Gly Gly Gly Gly Ser Asp Ile Gln Leu Thr Gln Ser His Lys Phe
130                 135                 140                 145

CTG TCC ACT TCA GTA GGA GAC AGG GTC AGC ATC ACC TGC AAG GCC AGT      576
Leu Ser Thr Ser Val Gly Asp Arg Val Ser Ile Thr Cys Lys Ala Ser
                150                 155                 160

CAG GAT GTG TAT AAT GCT GTT GCC TGG TAT CAA CAG AAA CCA GGA CAA      624
Gln Asp Val Tyr Asn Ala Val Ala Trp Tyr Gln Gln Lys Pro Gly Gln
            165                 170                 175

TCT CCT AAA CTT CTG ATT TAC TCG GCA TCC TCC CGG TAC ACT GGA GTC      672
Ser Pro Lys Leu Leu Ile Tyr Ser Ala Ser Ser Arg Tyr Thr Gly Val
        180                 185                 190

CCT TCT CGC TTC ACT GGC AGT GGC TCT GGG CCG GAT TTC ACT TTC ACC      720
Pro Ser Arg Phe Thr Gly Ser Gly Ser Gly Pro Asp Phe Thr Phe Thr
    195                 200                 205

ATC AGC AGT GTG CAG GCT GAA GAC CTG GCA GTT TAT TTC TGT CAG CAA      768
Ile Ser Ser Val Gln Ala Glu Asp Leu Ala Val Tyr Phe Cys Gln Gln
210                 215                 220                 225

CAT TTT CGT ACT CCA TTC ACG TTC GGC TCG GGG ACA AAA TTG GAG ATC      816
His Phe Arg Thr Pro Phe Thr Phe Gly Ser Gly Thr Lys Leu Glu Ile
                230                 235                 240

AAA GCT CTA GAG GGC GGC AGC CTG GCC GCG CTG ACC GCG CAC CAG GCC      864
Lys Ala Leu Glu Gly Gly Ser Leu Ala Ala Leu Thr Ala His Gln Ala
            245                 250                 255

TGC CAC CTG CCG CTG GAG ACT TTC ACC CGT CAT CGC CAG CCG CGC GGC      912
Cys His Leu Pro Leu Glu Thr Phe Thr Arg His Arg Gln Pro Arg Gly
        260                 265                 270

TGG GAA CAA CTG GAG CAG TGC GGC TAT CCG GTG CAG CGG CTG GTC GCC      960
Trp Glu Gln Leu Glu Gln Cys Gly Tyr Pro Val Gln Arg Leu Val Ala
    275                 280                 285

CTC TAC CTG GCG GCG CGA CTG TCA TGG AAC CAG GTC GAC CAG GTG ATC     1008
Leu Tyr Leu Ala Ala Arg Leu Ser Trp Asn Gln Val Asp Gln Val Ile
290                 295                 300                 305

CGC AAC GCC CTG GCC AGC CCC GGC AGC GGC GGC GAC CTG GGC GAA GCG     1056
Arg Asn Ala Leu Ala Ser Pro Gly Ser Gly Gly Asp Leu Gly Glu Ala
                310                 315                 320

ATC CGC GAG CAG CCG GAG CAG GCC CGT CTG GCC CTG ACC CTG GCC GCC     1104
Ile Arg Glu Gln Pro Glu Gln Ala Arg Leu Ala Leu Thr Leu Ala Ala
            325                 330                 335

GCC GAG AGC GAG CGC TTC GTC CGG CAG GGC ACC GGC AAC GAC GAG GCC     1152
Ala Glu Ser Glu Arg Phe Val Arg Gln Gly Thr Gly Asn Asp Glu Ala
        340                 345                 350

GGC GCG GCC AAC GCC GAC GTG GTG AGC CTG ACC TGC CCG GTC GCC GCC     1200
Gly Ala Ala Asn Ala Asp Val Val Ser Leu Thr Cys Pro Val Ala Ala
    355                 360                 365

GGT GAA TGC GCG GGC CCG GCG GAC AGC GGC GAC GCC CTG CTG GAG CGC     1248
Gly Glu Cys Ala Gly Pro Ala Asp Ser Gly Asp Ala Leu Leu Glu Arg
370                 375                 380                 385

AAC TAT CCC ACT GGC GCG GAG TTC CTC GGC GAC GGC GGC GAC GTC AGC     1296
Asn Tyr Pro Thr Gly Ala Glu Phe Leu Gly Asp Gly Gly Asp Val Ser
                390                 395                 400

TTC AGC ACC CGC GGC ACG CAG AAC TGG ACG GTG GAG CGG CTG CTC CAG     1344
Phe Ser Thr Arg Gly Thr Gln Asn Trp Thr Val Glu Arg Leu Leu Gln
            405                 410                 415

GCG CAC CGC CAA CTG GAG GAG CGC GGC TAT GTG TTC GTC GGC TAC CAC     1392
Ala His Arg Gln Leu Glu Glu Arg Gly Tyr Val Phe Val Gly Tyr His
        420                 425                 430
```

```
GGC ACC TTC CTC GAA GCG GCG CAA AGC ATC GTC TTC GGC GGG GTG CGC        1440
Gly Thr Phe Leu Glu Ala Ala Gln Ser Ile Val Phe Gly Gly Val Arg
    435                 440                 445

GCG CGC AGC CAG GAC CTC GAC GCG ATC TGG CGC GGT TTC TAT ATC GCC        1488
Ala Arg Ser Gln Asp Leu Asp Ala Ile Trp Arg Gly Phe Tyr Ile Ala
450                 455                 460                 465

GGC GAT CCG GCG CTG GCC TAC GGC TAC GCC CAG GAC CAG GAA CCC GAC        1536
Gly Asp Pro Ala Leu Ala Tyr Gly Tyr Ala Gln Asp Gln Glu Pro Asp
                470                 475                 480

GCA CGC GGC CGG ATC CGC AAC GGT GCC CTG CTG CGG GTC TAT GTG CCG        1584
Ala Arg Gly Arg Ile Arg Asn Gly Ala Leu Leu Arg Val Tyr Val Pro
            485                 490                 495

CGC TCG AGC CTG CCG GGC TTC TAC CGC ACC AGC CTG ACC CTG GCC GCG        1632
Arg Ser Ser Leu Pro Gly Phe Tyr Arg Thr Ser Leu Thr Leu Ala Ala
        500                 505                 510

CCG GAG GCG GCG GGC GAG GTC GAA CGG CTG ATC GGC CAT CCG CTG CCG        1680
Pro Glu Ala Ala Gly Glu Val Glu Arg Leu Ile Gly His Pro Leu Pro
    515                 520                 525

CTG CGC CTG GAC GCC ATC ACC GGC CCC GAG GAG GAA GGC GGG CGC CTG        1728
Leu Arg Leu Asp Ala Ile Thr Gly Pro Glu Glu Glu Gly Gly Arg Leu
530                 535                 540                 545

GAG ACC ATT CTC GGC TGG CCG CTG GCC GAG CGC ACC GTG GTG ATT CCC        1776
Glu Thr Ile Leu Gly Trp Pro Leu Ala Glu Arg Thr Val Val Ile Pro
                550                 555                 560

TCG GCG ATC CCC ACC GAC CCG CGC AAC GTC GGC GGC GAC CTC GAC CCG        1824
Ser Ala Ile Pro Thr Asp Pro Arg Asn Val Gly Gly Asp Leu Asp Pro
            565                 570                 575

TCC AGC ATC CCC GAC AAG GAA CAG GCG ATC AGC GCC CTG CCG GAC TAC        1872
Ser Ser Ile Pro Asp Lys Glu Gln Ala Ile Ser Ala Leu Pro Asp Tyr
        580                 585                 590

GCC AGC CAG CCC GGC AAA CCG CCG CGC GAG GAC CTG AAG TAACTGCCGC         1921
Ala Ser Gln Pro Gly Lys Pro Pro Arg Glu Asp Leu Lys
    595                 600                 605

GACCGGCCGG CTCCCTTCGC AGGAGCCGGC CTTCTCGGGG CCTGGCCATA CATCAGGTTT      1981

TCCTGATGCC AGCCCAATCG AATATGAATT C                                     2012

(2) INFORMATION FOR SEQ ID NO:14:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO:14:

Met Lys Lys Thr Ala Ile Ala Ile Ala Val Ala Leu Ala Gly Phe Ala
-31 -30             -25                 -20

Thr Val Ala Gln Ala Asp Tyr Lys Asp Asp Asp Lys Leu Ala Ser
-15                 -10                 -5                  1

Gln Val Gln Leu Gln Gln Ser Gly Pro Glu Leu Lys Lys Pro Gly Glu
            5                   10                  15

Thr Val Lys Ile Ser Cys Lys Ala Ser Gly Tyr Pro Phe Thr Asn Tyr
        20                  25                  30

Gly Met Asn Trp Val Lys Gln Ala Pro Gly Gln Gly Leu Lys Trp Met
    35                  40                  45

Gly Trp Ile Asn Thr Ser Thr Gly Glu Ser Thr Phe Ala Asp Asp Phe
50                  55                  60                  65
```

-continued

```
Lys Gly Arg Phe Asp Phe Ser Leu Glu Thr Ser Ala Asn Thr Ala Tyr
             70                  75                  80

Leu Gln Ile Asn Asn Leu Lys Ser Glu Asp Met Ala Thr Tyr Phe Cys
         85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Ser Asp Ile Gln Leu Thr Gln Ser His Lys Phe
130                 135                 140                 145

Leu Ser Thr Ser Val Gly Asp Arg Val Ser Ile Thr Cys Lys Ala Ser
                150                 155                 160

Gln Asp Val Tyr Asn Ala Val Ala Trp Tyr Gln Gln Lys Pro Gly Gln
            165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
            195                 200                 205

Ile Ser Ser Val Gln Ala Glu Asp Leu Ala Val Tyr Phe Cys Gln Gln
210                 215                 220                 225

His Phe Arg Thr Pro Phe Thr Phe Gly Ser Gly Thr Lys Leu Glu Ile
                230                 235                 240

Lys Ala Leu Glu Gly Gly Ser Leu Ala Ala Leu Thr Ala His Gln Ala
                245                 250                 255

Cys His Leu Pro Leu Glu Thr Phe Thr Arg His Arg Gln Pro Arg Gly
            260                 265                 270

Trp Glu Gln Leu Glu Gln Cys Gly Tyr Pro Val Gln Arg Leu Val Ala
            275                 280                 285

Leu Tyr Leu Ala Ala Arg Leu Ser Trp Asn Gln Val Asp Gln Val Ile
290                 295                 300                 305

Arg Asn Ala Leu Ala Ser Pro Gly Ser Gly Gly Asp Leu Gly Glu Ala
                310                 315                 320

Ile Arg Glu Gln Pro Glu Gln Ala Arg Leu Ala Leu Thr Leu Ala Ala
            325                 330                 335

Ala Glu Ser Glu Arg Phe Val Arg Gln Gly Thr Gly Asn Asp Glu Ala
            340                 345                 350

Gly Ala Ala Asn Ala Asp Val Val Ser Leu Thr Cys Pro Val Ala Ala
        355                 360                 365

Gly Glu Cys Ala Gly Pro Ala Asp Ser Gly Asp Ala Leu Leu Glu Arg
370                 375                 380                 385

Asn Tyr Pro Thr Gly Ala Glu Phe Leu Gly Asp Gly Gly Asp Val Ser
                390                 395                 400

Phe Ser Thr Arg Gly Thr Gln Asn Trp Thr Val Glu Arg Leu Leu Gln
            405                 410                 415

Ala His Arg Gln Leu Glu Glu Arg Gly Tyr Val Phe Val Gly Tyr His
            420                 425                 430

Gly Thr Phe Leu Glu Ala Ala Gln Ser Ile Val Phe Gly Gly Val Arg
        435                 440                 445

Ala Arg Ser Gln Asp Leu Asp Ala Ile Trp Arg Gly Phe Tyr Ile Ala
450                 455                 460                 465

Gly Asp Pro Ala Leu Ala Tyr Gly Tyr Ala Gln Asp Gln Glu Pro Asp
            470                 475                 480

Ala Arg Gly Arg Ile Arg Asn Gly Ala Leu Leu Arg Val Tyr Val Pro
            485                 490                 495
```

```
Arg Ser Ser Leu Pro Gly Phe Tyr Arg Thr Ser Leu Thr Leu Ala Ala
        500                 505                 510

Pro Glu Ala Ala Gly Glu Val Glu Arg Leu Ile Gly His Pro Leu Pro
    515                 520                 525

Leu Arg Leu Asp Ala Ile Thr Gly Pro Glu Glu Gly Gly Arg Leu
530                 535                 540                 545

Glu Thr Ile Leu Gly Trp Pro Leu Ala Glu Arg Thr Val Val Ile Pro
                550                 555                 560

Ser Ala Ile Pro Thr Asp Pro Arg Asn Val Gly Gly Asp Leu Asp Pro
            565                 570                 575

Ser Ser Ile Pro Asp Lys Glu Gln Ala Ile Ser Ala Leu Pro Asp Tyr
        580                 585                 590

Ala Ser Gln Pro Gly Lys Pro Pro Arg Glu Asp Leu Lys
    595                 600                 605
```

(2) INFORMATION FOR SEQ ID NO:15:

(i) SEQUENCE CHARACTERISTICS:
        (A) LENGTH: 2012 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Mouse/Pseudomonas aeruginosa
        (C) INDIVIDUAL ISOLATE: E. coli (vii) IMMEDIATE SOURCE:
        (B) CLONE: pWW215-51

(ix) FEATURE:
        (A) NAME/KEY: CDS
        (B) LOCATION: 1..1911
        (D) OTHER INFORMATION: /note= "64-87 FLAG peptide and
            enterokinase cleavage site;97-456 FWP51 heavy
            chain variable domain;457-501 15 aa linker
            sequence;502-822 FWP51 light chain variable
            domain"

(ix) FEATURE:
        (A) NAME/KEY: sig_peptide
        (B) LOCATION: 1..63
        (D) OTHER INFORMATION: /note= "ompA signal peptide"

(ix) FEATURE:
        (A) NAME/KEY: mat_peptide
        (B) LOCATION: 94..1911

(ix) FEATURE:
        (A) NAME/KEY: 3'UTR
        (B) LOCATION: 1912..2012
        (D) OTHER INFORMATION: /function= "3' non-coding region of
            the exotoxin A gene"

(ix) FEATURE:
        (A) NAME/KEY: misc_feature
        (B) LOCATION: 826..1911
        (D) OTHER INFORMATION: /note= "Exotoxin A gene coding
            region (coding for amino acids 252 to 613 of the
            mature exotoxin A)"

(xi) SEQUENCE DESCRIPTION: SEQ ID NO:15:

```
ATG AAA AAG ACA GCT ATC GCG ATT GCA GTG GCA CTG GCT GGT TTC GCT        48
Met Lys Lys Thr Ala Ile Ala Ile Ala Val Ala Leu Ala Gly Phe Ala
-31 -30                 -25                 -20
```

```
ACC GTT GCG CAA GCT GAC TAC AAG GAC GAC GAT GAC AAG CTA GCT TCT      96
Thr Val Ala Gln Ala Asp Tyr Lys Asp Asp Asp Asp Lys Leu Ala Ser
-15             -10                 -5                          1

CAG GTA CAA CTG CAG CAG TCT GGG GCT GAG CTG GTG AGG CCT GGG ACT     144
Gln Val Gln Leu Gln Gln Ser Gly Ala Glu Leu Val Arg Pro Gly Thr
             5                  10                  15

TCA GTG AAG CTG TCC TGC AAG GCT TCT GAT TAC ACC TTC ACC AGC TAC     192
Ser Val Lys Leu Ser Cys Lys Ala Ser Asp Tyr Thr Phe Thr Ser Tyr
         20                  25                  30

TGG ATG AAC TGG GTG AAG CAG AGG CCT GGA CAA GGC CTT GAA TGG ATT     240
Trp Met Asn Trp Val Lys Gln Arg Pro Gly Gln Gly Leu Glu Trp Ile
             35                  40                  45

GGT ATG ATT GAT CCT TCA GAC AGT GAA ACT CAA TAC AAT CAA ATG TTC     288
Gly Met Ile Asp Pro Ser Asp Ser Glu Thr Gln Tyr Asn Gln Met Phe
50                  55                  60                  65

AAG GAC AAG GCC GCA TTG ACT GTA GAC AAG TCC TCC AAT ACA GCC TAC     336
Lys Asp Lys Ala Ala Leu Thr Val Asp Lys Ser Ser Asn Thr Ala Tyr
             70                  75                  80

ATG CAA CTC AGC AGC CTG ACA TCT GAG GAC TCT GCG GTC TAT TAC TGT     384
Met Gln Leu Ser Ser Leu Thr Ser Glu Asp Ser Ala Val Tyr Tyr Cys
             85                  90                  95

GCA AAA GGG GGG GCC TCT GGG GAC TGG TAC TTC GAT GTC TGG GGC CAA     432
Ala Lys Gly Gly Ala Ser Gly Asp Trp Tyr Phe Asp Val Trp Gly Gln
             100                 105                 110

GGG ACC ACG GTC ACC GTT TCC TCT GGC GGT GGC GGT TCT GGT GGC GGT     480
Gly Thr Thr Val Thr Val Ser Ser Gly Gly Gly Gly Ser Gly Gly Gly
             115                 120                 125

GGC TCC GGC GGT GGC GGT TCT GAC ATC CAG CTG ACC CAG TCT CCA TCC     528
Gly Ser Gly Gly Gly Gly Ser Asp Ile Gln Leu Thr Gln Ser Pro Ser
130             135                 140                 145

TCA CTG TCT GCA TCT CTG GGA GGC GAA GTC ACC ATC ACT TGC AAG GCA     576
Ser Leu Ser Ala Ser Leu Gly Gly Glu Val Thr Ile Thr Cys Lys Ala
             150                 155                 160

AGC CAA GAC ATT AAG AAG TAT ATA GCT TGG TAC CAA CAC AAG CCT GGA     624
Ser Gln Asp Ile Lys Lys Tyr Ile Ala Trp Tyr Gln His Lys Pro Gly
             165                 170                 175

AAA AGT CCT CGG CTA CTC ATA CAC TAC ACA TCT GTA TTA CAG CCA GGC     672
Lys Ser Pro Arg Leu Leu Ile His Tyr Thr Ser Val Leu Gln Pro Gly
             180                 185                 190

ATC CCA TCC AGG TTC AGT GGA AGT GGG TCT GGG AGA GAT TAT TCC TTC     720
Ile Pro Ser Arg Phe Ser Gly Ser Gly Ser Gly Arg Asp Tyr Ser Phe
             195                 200                 205

AGC ATC CAC AAC CTG GAG CCT GAA GAT ATT GCA ACT TAT TAT TGT CTA     768
Ser Ile His Asn Leu Glu Pro Glu Asp Ile Ala Thr Tyr Tyr Cys Leu
210                 215                 220                 225

CAT TAT GAT TAT CTG TAC ACG TTC GGA GGG GGC ACC AAG CTG GAG ATC     816
His Tyr Asp Tyr Leu Tyr Thr Phe Gly Gly Gly Thr Lys Leu Glu Ile
             230                 235                 240

AAA GCT CTA GAG GGC GGC AGC CTG GCC GCG CTG ACC GCG CAC CAG GCC     864
Lys Ala Leu Glu Gly Gly Ser Leu Ala Ala Leu Thr Ala His Gln Ala
             245                 250                 255

TGC CAC CTG CCG CTG GAG ACT TTC ACC CGT CAT CGC CAG CCG CGC GGC     912
Cys His Leu Pro Leu Glu Thr Phe Thr Arg His Arg Gln Pro Arg Gly
             260                 265                 270

TGG GAA CAA CTG GAG CAG TGC GGC TAT CCG GTG CAG CGG CTG GTC GCC     960
Trp Glu Gln Leu Glu Gln Cys Gly Tyr Pro Val Gln Arg Leu Val Ala
275                 280                 285

CTC TAC CTG GCG GCG CGA CTG TCA TGG AAC CAG GTC GAC CAG GTG ATC    1008
Leu Tyr Leu Ala Ala Arg Leu Ser Trp Asn Gln Val Asp Gln Val Ile
290                 295                 300                 305
```

-continued

| | |
|---|---|
| CGC AAC GCC CTG GCC AGC CCC GGC AGC GGC GGC GAC CTG GGC GAA GCG<br>Arg Asn Ala Leu Ala Ser Pro Gly Ser Gly Gly Asp Leu Gly Glu Ala<br>                            310                        315                          320 | 1056 |
| ATC CGC GAG CAG CCG GAG CAG GCC CGT CTG GCC CTG ACC CTG GCC GCC<br>Ile Arg Glu Gln Pro Glu Gln Ala Arg Leu Ala Leu Thr Leu Ala Ala<br>                   325                        330                       335 | 1104 |
| GCC GAG AGC GAG CGC TTC GTC CGG CAG GGC ACC GGC AAC GAC GAG GCC<br>Ala Glu Ser Glu Arg Phe Val Arg Gln Gly Thr Gly Asn Asp Glu Ala<br>            340                        345                       350 | 1152 |
| GGC GCG GCC AAC GCC GAC GTG GTG AGC CTG ACC TGC CCG GTC GCC GCC<br>Gly Ala Ala Asn Ala Asp Val Val Ser Leu Thr Cys Pro Val Ala Ala<br>     355                        360                       365 | 1200 |
| GGT GAA TGC GCG GGC CCG GCG GAC AGC GGC GAC GCC CTG CTG GAG CGC<br>Gly Glu Cys Ala Gly Pro Ala Asp Ser Gly Asp Ala Leu Leu Glu Arg<br>370                   375                       380                       385 | 1248 |
| AAC TAT CCC ACT GGC GCG GAG TTC CTC GGC GAC GGC GGC GAC GTC AGC<br>Asn Tyr Pro Thr Gly Ala Glu Phe Leu Gly Asp Gly Gly Asp Val Ser<br>                   390                       395                       400 | 1296 |
| TTC AGC ACC CGC GGC ACG CAG AAC TGG ACG GTG GAG CGG CTG CTC CAG<br>Phe Ser Thr Arg Gly Thr Gln Asn Trp Thr Val Glu Arg Leu Leu Gln<br>            405                        410                       415 | 1344 |
| GCG CAC CGC CAA CTG GAG GAG CGC GGC TAT GTG TTC GTC GGC TAC CAC<br>Ala His Arg Gln Leu Glu Glu Arg Gly Tyr Val Phe Val Gly Tyr His<br>                   420                       425                       430 | 1392 |
| GGC ACC TTC CTC GAA GCG GCG CAA AGC ATC GTC TTC GGC GGG GTG CGC<br>Gly Thr Phe Leu Glu Ala Ala Gln Ser Ile Val Phe Gly Gly Val Arg<br>     435                        440                       445 | 1440 |
| GCG CGC AGC CAG GAC CTC GAC GCG ATC TGG CGC GGT TTC TAT ATC GCC<br>Ala Arg Ser Gln Asp Leu Asp Ala Ile Trp Arg Gly Phe Tyr Ile Ala<br>450                   455                       460                       465 | 1488 |
| GGC GAT CCG GCG CTG GCC TAC GGC TAC GCC CAG GAC CAG GAA CCC GAC<br>Gly Asp Pro Ala Leu Ala Tyr Gly Tyr Ala Gln Asp Gln Glu Pro Asp<br>                   470                       475                       480 | 1536 |
| GCA CGC GGC CGG ATC CGC AAC GGT GCC CTG CTG CGG GTC TAT GTG CCG<br>Ala Arg Gly Arg Ile Arg Asn Gly Ala Leu Leu Arg Val Tyr Val Pro<br>            485                        490                       495 | 1584 |
| CGC TCG AGC CTG CCG GGC TTC TAC CGC ACC AGC CTG ACC CTG GCC GCG<br>Arg Ser Ser Leu Pro Gly Phe Tyr Arg Thr Ser Leu Thr Leu Ala Ala<br>     500                        505                       510 | 1632 |
| CCG GAG GCG GCG GGC GAG GTC GAA CGG CTG ATC GGC CAT CCG CTG CCG<br>Pro Glu Ala Ala Gly Glu Val Glu Arg Leu Ile Gly His Pro Leu Pro<br>515                   520                       525 | 1680 |
| CTG CGC CTG GAC GCC ATC ACC GGC CCC GAG GAG GAA GGC GGG CGC CTG<br>Leu Arg Leu Asp Ala Ile Thr Gly Pro Glu Glu Glu Gly Gly Arg Leu<br>530                   535                       540                       545 | 1728 |
| GAG ACC ATT CTC GGC TGG CCG CTG GCC GAG CGC ACC GTG GTG ATT CCC<br>Glu Thr Ile Leu Gly Trp Pro Leu Ala Glu Arg Thr Val Val Ile Pro<br>                   550                       555                       560 | 1776 |
| TCG GCG ATC CCC ACC GAC CCG CGC AAC GTC GGC GGC GAC CTC GAC CCG<br>Ser Ala Ile Pro Thr Asp Pro Arg Asn Val Gly Gly Asp Leu Asp Pro<br>            565                        570                       575 | 1824 |
| TCC AGC ATC CCC GAC AAG GAA CAG GCG ATC AGC GCC CTG CCG GAC TAC<br>Ser Ser Ile Pro Asp Lys Glu Gln Ala Ile Ser Ala Leu Pro Asp Tyr<br>                   580                       585                       590 | 1872 |
| GCC AGC CAG CCC GGC AAA CCG CCG CGC GAG GAC CTG AAG TAACTGCCGC<br>Ala Ser Gln Pro Gly Lys Pro Pro Arg Glu Asp Leu Lys<br>     595                        600                       605 | 1921 |
| GACCGGCCGG CTCCCTTCGC AGGAGCCGGC CTTCTCGGGG CCTGGCCATA CATCAGGTTT | 1981 |
| TCCTGATGCC AGCCCAATCG AATATGAATT C | 2012 |

(2) INFORMATION FOR SEQ ID NO:16:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Lys Thr Ala Ile Ala Ile Ala Val Ala Leu Ala Gly Phe Ala
-31 -30              -25              -20

Thr Val Ala Gln Ala Asp Tyr Lys Asp Asp Asp Lys Leu Ala Ser
-15              -10               -5                     1

Gln Val Gln Leu Gln Gln Ser Gly Ala Glu Leu Val Arg Pro Gly Thr
                 5                  10                 15

Ser Val Lys Leu Ser Cys Lys Ala Ser Asp Tyr Thr Phe Thr Ser Tyr
                20                  25                  30

Trp Met Asn Trp Val Lys Gln Arg Pro Gly Gln Gly Leu Glu Trp Ile
             35                  40                  45

Gly Met Ile Asp Pro Ser Asp Ser Glu Thr Gln Tyr Asn Gln Met Phe
         50                  55                  60

Lys Asp Lys Ala Ala Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                 85                  90                  95

Ala Lys Gly Gly Ala Ser Gly Asp Trp Tyr Phe Asp Val Trp Gly Gln
                100                 105                 110

Gly Thr Thr Val Thr Val Ser Ser Gly Gly Gly Ser Gly Gly Gly
             115                 120                 125

Gly Ser Gly Gly Gly Gly Ser Asp Ile Gln Leu Thr Gln Ser Pro Ser
        130                 135                 140

Ser Leu Ser Ala Ser Leu Gly Gly Glu Val Thr Ile Thr Cys Lys Ala
145                 150                 155                 160

Ser Gln Asp Ile Lys Lys Tyr Ile Ala Trp Tyr Gln His Lys Pro Gly
                165                 170                 175

Lys Ser Pro Arg Leu Leu Ile His Tyr Thr Ser Val Leu Gln Pro Gly
                180                 185                 190

Ile Pro Ser Arg Phe Ser Gly Ser Gly Ser Gly Arg Asp Tyr Ser Phe
                195                 200                 205

Ser Ile His Asn Leu Glu Pro Glu Asp Ile Ala Thr Tyr Tyr Cys Leu
210                 215                 220

His Tyr Asp Tyr Leu Tyr Thr Phe Gly Gly Gly Thr Lys Leu Glu Ile
225                 230                 235                 240

Lys Ala Leu Glu Gly Gly Ser Leu Ala Ala Leu Thr Ala His Gln Ala
                245                 250                 255

Cys His Leu Pro Leu Glu Thr Phe Thr Arg His Arg Gln Pro Arg Gly
                260                 265                 270

Trp Glu Gln Leu Glu Gln Cys Gly Tyr Pro Val Gln Arg Leu Val Ala
                275                 280                 285

Leu Tyr Leu Ala Ala Arg Leu Ser Trp Asn Gln Val Asp Gln Val Ile
                290                 295                 300

Arg Asn Ala Leu Ala Ser Pro Gly Ser Gly Gly Asp Leu Gly Glu Ala
305                 310                 315                 320
```

```
Ile Arg Glu Gln Pro Glu Gln Ala Arg Leu Ala Leu Thr Leu Ala Ala
            325                 330                 335

Ala Glu Ser Glu Arg Phe Val Arg Gln Gly Thr Gly Asn Asp Glu Ala
            340                 345                 350

Gly Ala Ala Asn Ala Asp Val Ser Leu Thr Cys Pro Val Ala Ala
            355                 360                 365

Gly Glu Cys Ala Gly Pro Ala Asp Ser Gly Asp Ala Leu Leu Glu Arg
370                 375                 380

Asn Tyr Pro Thr Gly Ala Glu Phe Leu Gly Asp Gly Asp Val Ser
385                 390                 395                 400

Phe Ser Thr Arg Gly Thr Gln Asn Trp Thr Val Glu Arg Leu Leu Gln
                405                 410                 415

Ala His Arg Gln Leu Glu Glu Arg Gly Tyr Val Phe Val Gly Tyr His
            420                 425                 430

Gly Thr Phe Leu Glu Ala Ala Gln Ser Ile Val Phe Gly Val Arg
            435                 440                 445

Ala Arg Ser Gln Asp Leu Asp Ala Ile Trp Arg Gly Phe Tyr Ile Ala
450                 455                 460

Gly Asp Pro Ala Leu Ala Tyr Gly Tyr Ala Gln Asp Gln Glu Pro Asp
465                 470                 475                 480

Ala Arg Gly Arg Ile Arg Asn Gly Ala Leu Leu Arg Val Tyr Val Pro
                485                 490                 495

Arg Ser Ser Leu Pro Gly Phe Tyr Arg Thr Ser Leu Thr Leu Ala Ala
            500                 505                 510

Pro Glu Ala Ala Gly Glu Val Glu Arg Leu Ile Gly His Pro Leu Pro
            515                 520                 525

Leu Arg Leu Asp Ala Ile Thr Gly Pro Glu Glu Gly Gly Arg Leu
            530                 535                 540

Glu Thr Ile Leu Gly Trp Pro Leu Ala Glu Arg Thr Val Val Ile Pro
545                 550                 555                 560

Ser Ala Ile Pro Thr Asp Pro Arg Asn Val Gly Gly Asp Leu Asp Pro
                565                 570                 575

Ser Ser Ile Pro Asp Lys Glu Gln Ala Ile Ser Ala Leu Pro Asp Tyr
            580                 585                 590

Ala Ser Gln Pro Gly Lys Pro Pro Arg Glu Asp Leu Lys
            595                 600                 605

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:17:

Gly Gly Gly Gly Ser Gly Gly Gly Ser Gly Gly Gly Ser
121                 125                 130                 135

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA
```

(iii) HYPOTHETICAL: NO (iv) ANTI-SENSE: NO (xi) SEQUENCE DESCRIPTION: SEQ ID NO:18:

TGAGGAGACG GTGACCGTGG TCCCTTGGCC CCAG                                34

(2) INFORMATION FOR SEQ ID NO:19:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:19:

TCACTGGATG GTGGGAAGAT GGA                                            23

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:20:

AGATCCAGGG GCCAGTGGAT AGA                                            23

(2) INFORMATION FOR SEQ ID NO:21:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:21:

AGGTSMARCT GCAGSAGTCW GG                                             22

(2) INFORMATION FOR SEQ ID NO:22:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO -continued (xi) SEQUENCE DESCRIPTION: SEQ ID NO:22:

GTTAGATCTC CAGCTTGGTS CS                                                     22

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:23:

GACATTCAGC TGACCCAGTC TCCA                                                   24

(2) INFORMATION FOR SEQ ID NO:24:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:24:

CAAGCTTCTC AGGTACAACT GCAGGAGGTC ACCGTTTCCT CTGGCGG                           47

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:25:

GAAACGGTGA CCTCCTGCAG TTGTACCTGA GAAGCTTGCA TG                               42

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:26:

TGGCGGTTCT GGTGGCGGTG GCTCCGGCGG TGGCGGTTCT GAC                              43

(2) INFORMATION FOR SEQ ID NO:27:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:27:

GCCACCGCCG GAGCCACCGC CACCAGAACC GCCACCGCCA GAG                43

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:28:

ATCCAGCTGG AGATCTAGCT GATCAAAGCT                               30

(2) INFORMATION FOR SEQ ID NO:29:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:29:

CTAGAGCTTT GATCAGCTAG ATCTCCAGCT GGATGTCAGA ACC                43

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:30:

GACATTCAGC TGACCCAG                                            18

(2) INFORMATION FOR SEQ ID NO:31:

(i) SEQUENCE CHARACTERISTICS:

```
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:31:

GCCCGTTAGA TCTCCAATTT TGTCCCCGAG                                    30

(2) INFORMATION FOR SEQ ID NO:32:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:32:

ACAAAATTGG AGATCAAAGC TCTAGA                                        26

(2) INFORMATION FOR SEQ ID NO:33:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:33:

CCCTCTAGAG CCTGTTCTGG AAAAC                                         25

(2) INFORMATION FOR SEQ ID NO:34:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:34:

CCCGAGCTCT GCCATTAAG                                                19
```